US012807589B2

(12) United States Patent
Olson et al.

(10) Patent No.: US 12,807,589 B2
(45) Date of Patent: Nov. 24, 2026

(54) ERGOLINE-LIKE COMPOUNDS FOR PROMOTING NEURAL PLASTICITY

(71) Applicants: The Regents of the University of California, Oakland, CA (US); Delix Therapeutics, Inc., Palo Alto, CA (US)

(72) Inventors: David E. Olson, Oakland, CA (US); Lee Dunlap, Oakland, CA (US); Florence Wagner, Palo Alto, CA (US); Milan Chytil, Palo Alto, CA (US); Noel Aaron Powell, Palo Alto, CA (US)

(73) Assignees: The Regents of the University of California, Oakland, CA (US); Delix Therapeutics, Inc., Palo Alto, CA (US)

( * ) Notice: Subject to any disclaimer, the term of this patent is extended or adjusted under 35 U.S.C. 154(b) by 1124 days.

(21) Appl. No.: 17/768,725

(22) PCT Filed: Oct. 14, 2020

(86) PCT No.: PCT/US2020/055507
§ 371 (c)(1),
(2) Date: Apr. 13, 2022

(87) PCT Pub. No.: WO2021/076572
PCT Pub. Date: Apr. 22, 2021

(65) Prior Publication Data

US 2023/0295106 A1 Sep. 21, 2023

Related U.S. Application Data

(60) Provisional application No. 62/914,807, filed on Oct. 14, 2019.

(51) Int. Cl.

| | |
|---|---|
| ***C07D 401/04*** | (2006.01) |
| ***A61P 25/28*** | (2006.01) |
| ***C07D 209/90*** | (2006.01) |
| ***C07D 211/78*** | (2006.01) |
| ***C07D 405/14*** | (2006.01) |
| ***C07D 471/06*** | (2006.01) |
| ***C07D 491/16*** | (2006.01) |

(52) U.S. Cl.
CPC ............ *C07D 401/04* (2013.01); *A61P 25/28* (2018.01); *C07D 209/90* (2013.01); *C07D 211/78* (2013.01); *C07D 405/14* (2013.01); *C07D 471/06* (2013.01); *C07D 491/16* (2013.01)

(58) Field of Classification Search
CPC .. C07D 401/04; C07D 209/90; C07D 211/78; C07D 405/14; C07D 471/06; C07D 491/16; C07D 403/04; C07D 491/048; C07D 491/06
See application file for complete search history.

(56) References Cited

U.S. PATENT DOCUMENTS

| | | | |
|---|---|---|---|
| 3,525,750 | A | 8/1970 | Renner |
| 3,553,232 | A | 1/1971 | Hester |
| 3,637,744 | A | 1/1972 | Yardley et al. |
| 3,652,588 | A | 3/1972 | Hester |
| 4,478,750 | A | 10/1984 | Gadient |
| 4,581,354 | A | 4/1986 | Bell |
| 4,841,056 | A | 6/1989 | Hunter |
| 4,902,691 | A | 2/1990 | Cohen et al. |
| 5,068,234 | A | 11/1991 | D et al. |
| 5,219,859 | A | 6/1993 | Festal et al. |
| 5,494,928 | A | 2/1996 | Boes |
| 5,627,077 | A | 5/1997 | Dyllick-Brenzinger et al. |
| 5,814,642 | A | 9/1998 | Goto et al. |
| 5,843,682 | A | 12/1998 | Sigler et al. |
| 5,852,046 | A | 12/1998 | Lang et al. |
| 6,017,945 | A | 1/2000 | Rawson et al. |
| 6,380,238 | B1 | 4/2002 | Adams et al. |
| 6,380,242 | B1 | 4/2002 | Arora et al. |
| 6,407,092 | B1 | 6/2002 | Hester et al. |
| 6,468,999 | B1 | 10/2002 | Jacobsen et al. |
| 6,548,493 | B1 | 4/2003 | Robichaud et al. |
| 6,552,017 | B1 | 4/2003 | Robichaud et al. |
| 6,635,639 | B2 | 10/2003 | Arora et al. |
| 6,828,314 | B2 | 12/2004 | Frank et al. |
| 6,903,090 | B2 | 6/2005 | Frank et al. |
| 8,338,447 | B2 | 12/2012 | Hung et al. |
| 8,367,655 | B2 | 2/2013 | Rajagopalan |
| 9,481,676 | B2 | 11/2016 | Hung et al. |
| 10,583,123 | B2 | 3/2020 | Yang et al. |
| 11,254,640 | B2 | 2/2022 | Olson et al. |
| 11,414,423 | B1 | 8/2022 | Olson et al. |
| 11,697,651 | B2 | 7/2023 | Muratore et al. |
| 2002/0022616 | A1 | 2/2002 | Fu |
| 2002/0169322 | A1 | 11/2002 | Arora et al. |
| 2002/0173503 | A1 | 11/2002 | Robichaud et al. |
| 2003/0199491 | A1 | 10/2003 | Hennequin |
| 2003/0212055 | A1 | 11/2003 | Hennequin |
| 2003/0220321 | A1 | 11/2003 | Frank et al. |
| 2003/0225058 | A1 | 12/2003 | Frank et al. |
| 2003/0232828 | A1 | 12/2003 | Bernotas et al. |

(Continued)

FOREIGN PATENT DOCUMENTS

| | | | |
|---|---|---|---|
| AU | 614343 | B2 | 8/1991 |
| CA | 2715282 | A1 | 8/2009 |

(Continued)

OTHER PUBLICATIONS

PubChem CID 3039341, National Center for Biotechnology Information. PubChem Compound Summary for CID 3039341, Ergoline-8-beta-carboxamide, 9,10-didehydro-N, N-diethyl-12-methoxy-6-methyl-. https://pubchem.ncbi.nlm.nih.gov/ compound/3039341. Accessed Feb. 26, 2025, create date Aug. 9, 2005. (Year: 2005).*

(Continued)

*Primary Examiner* — Laura L Stockton
(74) *Attorney, Agent, or Firm* — Mintz Levin Cohn Ferris Glovsky and Popeo, P.C.

(57) ABSTRACT

Provided herein are ergoline-derived heterocyclic compounds which can be useful for methods of treating a disease or for increasing neural plasticity. The compounds can also be useful for increasing dendritic spine density.

5 Claims, 6 Drawing Sheets

(56) References Cited

U.S. PATENT DOCUMENTS

| | | | |
|---|---|---|---|
| 2003/0236278 | A1 | 12/2003 | Bernotas et al. |
| 2004/0023947 | A1 | 2/2004 | Martin et al. |
| 2004/0092502 | A1 | 5/2004 | Fevig et al. |
| 2004/0242884 | A1 | 12/2004 | Larsen et al. |
| 2005/0070558 | A1 | 3/2005 | Vidal et al. |
| 2005/0250767 | A1 | 11/2005 | Weiner et al. |
| 2006/0105030 | A1 | 5/2006 | Windt-hanke et al. |
| 2006/0148808 | A1 | 7/2006 | Robichaud et al. |
| 2006/0199829 | A1 | 9/2006 | Anandan et al. |
| 2006/0247228 | A1 | 11/2006 | Umeda et al. |
| 2007/0197603 | A1 | 8/2007 | Consonni et al. |
| 2007/0213359 | A1 | 9/2007 | Burstein et al. |
| 2007/0254875 | A1 | 11/2007 | Zhi et al. |
| 2009/0318446 | A1 | 12/2009 | Fischer et al. |
| 2010/0022580 | A1 | 1/2010 | Hung et al. |
| 2010/0152163 | A1 | 6/2010 | Hung et al. |
| 2010/0317863 | A1 | 12/2010 | Kuzmich et al. |
| 2011/0003793 | A1 | 1/2011 | Guzzo et al. |
| 2011/0003836 | A1 | 1/2011 | Mcknight et al. |
| 2011/0003840 | A1 | 1/2011 | Rajagopalan |
| 2011/0229555 | A1 | 9/2011 | Helson et al. |
| 2011/0245222 | A1 | 10/2011 | Payan et al. |
| 2012/0245161 | A1 | 9/2012 | Choi-Sledeski et al. |
| 2012/0296569 | A1 | 11/2012 | Shahaf et al. |
| 2013/0040977 | A1 | 2/2013 | Mcknight et al. |
| 2013/0178618 | A1 | 7/2013 | Boulanger |
| 2013/0190293 | A1 | 7/2013 | Chakravarty et al. |
| 2013/0195866 | A1 | 8/2013 | Bacskai et al. |
| 2013/0217675 | A1 | 8/2013 | Chakravarty et al. |
| 2013/0225558 | A1 | 8/2013 | Chakravarty et al. |
| 2014/0155384 | A1 | 6/2014 | Protter et al. |
| 2014/0206711 | A1 | 7/2014 | Chakravarty et al. |
| 2014/0228353 | A1 | 8/2014 | Protter et al. |
| 2014/0275531 | A1 | 9/2014 | Bollu et al. |
| 2014/0275548 | A1 | 9/2014 | Basinger et al. |
| 2014/0296209 | A1 | 10/2014 | Protter et al. |
| 2014/0303144 | A1 | 10/2014 | Protter et al. |
| 2014/0343018 | A1 | 11/2014 | Mcknight et al. |
| 2015/0057301 | A1 | 2/2015 | Mcknight et al. |
| 2015/0141345 | A1 | 5/2015 | Gozes et al. |
| 2015/0266884 | A1 | 9/2015 | Protter et al. |
| 2016/0002237 | A1 | 1/2016 | Rajagopalan |
| 2018/0263964 | A1 | 9/2018 | Bamdad et al. |
| 2020/0030309 | A1 | 1/2020 | Olson |
| 2020/0087305 | A1 | 3/2020 | Tomesch et al. |
| 2020/0375967 | A1 | 12/2020 | Stamets |
| 2021/0115042 | A1 | 4/2021 | Armer et al. |
| 2022/0251040 | A1 | 8/2022 | Olson et al. |
| 2022/0304980 | A1 | 9/2022 | Arnold et al. |
| 2023/0117791 | A1 | 4/2023 | Olson et al. |
| 2023/0150963 | A1 | 5/2023 | Baggot et al. |
| 2023/0202965 | A1 | 6/2023 | Short et al. |
| 2024/0124456 | A1 | 4/2024 | Cheng et al. |
| 2024/0208973 | A1 | 6/2024 | Olson et al. |
| 2025/0057822 | A1 | 2/2025 | Olson et al. |
| 2025/0122164 | A1 | 4/2025 | Olson et al. |

FOREIGN PATENT DOCUMENTS

| | | | | |
|---|---|---|---|---|
| CN | 102977091 | A | 3/2013 | |
| CN | 102977092 | A | 3/2013 | |
| EP | 0473550 | A1 | 3/1992 | |
| GB | 2550110 | A | 11/2017 | |
| JP | 2017031088 | A | 2/2017 | |
| NL | 6515701 | A | 6/1966 | |
| WO | 9423720 | A1 | 10/1994 | |
| WO | 95024200 | A1 | 9/1995 | |
| WO | 9840102 | A1 | 9/1998 | |
| WO | 0038677 | A1 | 7/2000 | |
| WO | 0064899 | A1 | 11/2000 | |
| WO | 0170223 | A1 | 9/2001 | |
| WO | 2004005389 | A1 | 1/2004 | |
| WO | 2004064738 | A2 | 8/2004 | |
| WO | WO-2005051488 | A1 * | 6/2005 | ................ A61P 9/12 |
| WO | 2007118314 | A1 | 10/2007 | |
| WO | 2008117935 | A1 | 10/2008 | |
| WO | 2008157845 | A1 | 12/2008 | |
| WO | 2009035473 | A2 | 3/2009 | |
| WO | 2009036996 | A2 | 3/2009 | |
| WO | 2009103022 | A1 | 8/2009 | |
| WO | 2011103433 | A1 | 8/2011 | |
| WO | 2012112966 | A1 | 8/2012 | |
| WO | 2012154261 | A1 | 11/2012 | |
| WO | 2013007698 | A1 | 1/2013 | |
| WO | 2017216279 | A1 | 12/2017 | |
| WO | 2018045178 | A1 | 3/2018 | |
| WO | 2018064465 | A1 | 4/2018 | |
| WO | 2018209341 | A1 | 11/2018 | |
| WO | 2019099402 | A1 | 5/2019 | |
| WO | 2020169851 | A1 | 8/2020 | |
| WO | 2020176597 | A1 | 9/2020 | |
| WO | 2020176599 | A1 | 9/2020 | |
| WO | 2020181050 | A1 | 9/2020 | |
| WO | 2020181194 | A1 | 9/2020 | |
| WO | 2020186027 | A1 | 9/2020 | |
| WO | 2021178691 | A1 | 9/2021 | |
| WO | 2022020352 | A1 | 1/2022 | |
| WO | 2022067165 | A1 | 1/2022 | |
| WO | 2022051670 | A1 | 3/2022 | |
| WO | 2022081631 | A1 | 4/2022 | |
| WO | 2022120181 | A1 | 6/2022 | |
| WO | 2022120475 | A1 | 6/2022 | |
| WO | 2022170268 | A1 | 8/2022 | |
| WO | 2022221415 | A1 | 10/2022 | |
| WO | 2022246554 | A1 | 12/2022 | |
| WO | 2023283364 | A1 | 1/2023 | |
| WO | 2023018480 | A1 | 2/2023 | |
| WO | 2023018864 | A1 | 2/2023 | |
| WO | 2023023298 | A1 | 2/2023 | |
| WO | 2023059546 | A1 | 4/2023 | |
| WO | 2023073423 | A1 | 5/2023 | |
| WO | 2023077127 | A2 | 5/2023 | |
| WO | 2023081306 | A1 | 5/2023 | |
| WO | 2023081753 | A1 | 5/2023 | |
| WO | 2023092195 | A1 | 6/2023 | |
| WO | 2023108164 | A2 | 6/2023 | |
| WO | 2023108165 | A2 | 6/2023 | |
| WO | 2023108174 | A1 | 6/2023 | |
| WO | 2023114472 | A1 | 6/2023 | |
| WO | 2023115006 | A1 | 6/2023 | |
| WO | 2023115060 | A1 | 6/2023 | |
| WO | 2023115165 | A1 | 6/2023 | |
| WO | 2023115166 | A1 | 6/2023 | |
| WO | 2023122135 | A1 | 6/2023 | |
| WO | 2024059495 | A1 | 3/2024 | |
| WO | 2025014719 | A3 | 4/2025 | |
| WO | 2025080608 | A1 | 4/2025 | |
| WO | 2025080609 | A1 | 4/2025 | |
| WO | 2025137596 | A1 | 6/2025 | |

OTHER PUBLICATIONS

PubChem CID 124303351, National Center for Biotechnology Information. PubChem Compound Summary for CID 124303351, (10R)-N, N-dipropyl-1-azatricyclo[6.3.1.04, 12]dodeca-2,4(12),5,7-tetraen-10-amine. https://pubchem.ncbi.nlm.nih.gov/compound/124303351. Accessed Sep. 10, 2025, create date Apr. 10, 2017. (Year: 2017).*

Chemical Abstracts Registry No. 1347137-88-5, indexed in the Registry file on STN CAS Online Dec. 1, 2011. (Year: 2011).*

(2018) Depression, The National Institute of Mental Health: www.nimh.nih.gov, 13 Pages.

European Search Report for EP Application 17857489.3, mailed on Apr. 8, 2020, 6 pages.

International Search Report and Written Opinion for PCT/US2022/024626, mailed Jul. 1, 2022, 9 pages.

International Search Report and Written Opinion received for International Application No. PCT/US20/19858, mailed on Jul. 15, 2020, 12 pages.

International Search Report and Written Opinion received for International Application No. PCT/US2020/055507, mailed on Mar. 1, 2021, 12 pages.

(56) References Cited

OTHER PUBLICATIONS

International Search Report and Written Opinion received for PCT Application No. PCT/US2017/054277, mailed on Dec. 14, 2017, 10 pages.
International Search Report and Written Opinion received for PCT Application No. PCT/US2020/019856, mailed on Jun. 26, 2020, 11 pages.
Third Party Observations received for European Application No. 17857489.3, mailed on Feb. 15, 2022, 2 pages.
Anderson et al. (Sep. 2003) "The Process of Structure-based Drug Design", Chemistry and Biology, 10(9):787-797.
Antonaci et al. (2016) "Recent Advances in Migraine Therapy", SpringerPlus, 5:1-14.
Borovac Josip A. (Mar. 24, 2016) "Side effects of a dopamine agonist therapy for Parkinson's disease: a mini-review of clinical pharmacology", Yale Journal of Biology and Medicine, 89(1):37-47.
Cameron et al. (Jan. 21, 2021) "A Non-hallucinogenic Psychedelic Analogue with Therapuetic Potential", Nature, 589:474-479 (24 pages).
Cameron et al. (Jul. 2019) "Chronic, Intermittent Microdoses of the Psychedelic N,N-Dimethyltryptamine (DMT) Produce Positive Effects on Mood and Anxiety in Rodents", ACS Chemical Neuroscience, 10(7):3261-3270.
Cameron et al. (Oct. 2018) "Dark Classics in Chemical Neuroscience: N,N-Dimethyltryptamine (DMT)", ACS Chemical Neuroscience, 9(10):2344-2357.
Cameron et al. (Jul. 2018) "Effects of N,N-Dimethyltryptamine on Rat Behaviors Relevant to Anxiety and Depression", ACS Chemical Neuroscience, 9(7):1582-1590 (22 pages).
Cameron et al. (Apr.-Jun. 2020) "Psychedelic Microdosing: Prevalence and Subjective Effects", Jounal of Psychoactive Drugs, 52(2):113-122.
Chang-Fong et al. (Jan. 21, 2002) "Evaluation of Isotryptamine Derivatives at 5-HT2 Serotonin Receptors", Bioorganic & Medicinal Chemistry Letters, 12(2):155-158.
Chiba et al. (Aug. 2010), "Cabergoline, a Dopamine Receptor Agaonist, has an Antidepressant-like Property and Enhances Brain-derived Neurotrophic Factor Signaling", Psychpharmacology, 211(3):291-301 (23 pages).
Dunlap et al., (Jan. 2020) "Identification of Psychoplastogenic N,N-Dimethylaminoisotryptamine (isoDMT) Analogues through Structure—Activity Relationship Studies", Journal of Medicinal Chemistry, 63(3):1142-1155 (36 pages).
Glennon et al. (2000) "Binding of Beta-Carbolines and Related Agents at Serotonin (5-HT(2) and 5-HT(1A)), Dopamine (D(2)) and Benzodiazepine Receptors", Drug & Alcohol Dependence, 60(2):121-132.
Glennon et al. (1983) "DOM-stimulus Generalization to LSD and other Hallucinogenic Indolealkylamines", European Journal of Pharmacology, 86:453-459.
Glennon et al. (1984) "Sythesis and Evaluation of a Novel Series of N ,N-Dimethylisotryptamines", 27(1):41-45.
Goadsby et al., (Nov. 11, 2005) "Comparative Efficacy of Eletriptan and Sumatriptan in Reducing Headache Recurrence in High-Risk Migraine Patients", Journal of the Neurological Sciences, 1533, 1 page.
Golda et al. (Jun. 1987) "Animal Model of Depression: Drug Induced Changes Independent of Changes in Exploratory Activity", Activitas Nervosa superior, 29(2):114-115.
Golda et al. (Mar. 1986) "Animal Model of Depression: Imipramine, Bromocriptine and Lisuride Alleviate Motor Depression", Activitas Nervosa Superior, 28(1):26-27(4 pages).
Golda et al. (1984) "Reactivity to the Electric Shocks and Motor Depression as a Consequence of Inescapable Shocking: The Effect of Acute Lisuride Treatment", Sb Ved Pr Lek Fak Karlovy Univerzity Hradci Kralove, 27(4):377-392.
Harris et al. (Nov.-Dec. 2012) "Cabergoline Associated with First Episode Mania", Psychosomatics, 53(6):595-600 (10 pages).
Hester et al. (Jan. 1, 1968), "Azepinoindoles. I. Hexahydroazepino[4,5-b]indoles", Journal of Medicinal Chemistry, 11:101-106.
Hougaku et al. (Jan. 1994) "Therapeutic Effect of Lisuride maleate on Post-stroke Depression", Japanese Journal of Geriatrics, 31:52-59.
Izumi et al. (Dec. 2000) "Open Pergolide Treatment of Tricyclic and Heterocyclic Antidepressant-Resistant Depression", Journal of Affective Disorders, 61:127-132.
Konopaske et al. (Dec. 2014) "Prefrontal Cortical Dendritic Spine Pathology in Schizophrenia and Bipolar disorder", JAMA Psychiatry, 71(12):1323-1331.
Lieberman et al. (Nov. 1981) "Use of Lisuride in Advanced Parkinson's Disease. Potent Dopamine and Serotonin Agonist", New York State Journal of Medicine, 81(12):1751-1755.
Luquin et al. (1987) "Parenteral Administration of Lisuride in Parkinson's Disease", Advances in Neurology, 45:561-568.
Ly et al. (Jun. 12, 2018) "Psychedelics Promote Structural and Functional Neural Plasticity", Cell Reports, 23(11):3170-3182.
Meintzschel et al. (Oct. 12, 2005) "Modification of Practice-dependent Plasticity in Human Motor Cortex by Neuromodulators", Cerebral Cortex, 16(8):1106-1115.
Meyer et al. (Jan. 2001) "The Effect of Paroxetine on 5-HT 2A Receptors in Depression: An [18F]Setoperone PET Imaging Study", The American Journal of Psychiatry, 158(1):78-85.
Halford, Bethany (Dec. 9, 2020) "Ibogaine Inspires Potential Neuropsychiatric Treatment", C&E News, 3 pages.
Moyer et al. (2015) "Dendritic Spine Alterations in Schizophrenia", Neuroscience Letters, 601:46-53 (18 pages).
Nakamura et al. (1989) "Effects in Animal Models of Depression of Lisuride Along and Upon Co-Administration With Antidepressants", Folia Pharmacologia Japonica, 94(1):81-89.
Odaka et al. (Jun. 2014) "Cabergoline, Dopamine D2 REceptor Agonist, Prevents Neuronal Cell Death under Oxidative Stress via Reducing Excitotoxicity", PLoS One, 9(6):12 pages.
Penzes et al. (Mar. 2011) "Dendritic Spine Pathology in Neuropsychiatric Disorders", Nature Neuroscience Review, 14(3):285-293.
Pfizer Canana, Inc. (Jul. 23, 2013) "Product Monograph", Pfizer Canada Inc., 2 pages.
PUBCHEM (Oct. 20, 2014) "1,2,3,4-Tetrahydropyrrolo[2,3-b]Indole", PubChem CID 82415753, 8 Pages.
PUBCHEM (Jun. 16, 2016) "3,4-Trimethylen-inden", PubChem SID 314981250, 5 pages.
PUBCHEM (Aug. 8, 2005) "Carbazole, 9-(1-methyl-2-piperidyl)methyl-", PubChem CID 43403, 10 Pages.
Pumphrey et al. (Jun. 11, 2012) "RhII2-Catalyzed Synthesis of α-, β-, or δ-Carbolines from Aryl Azides", Angewandte Chemie International Edition, 51(24): 5920-5923 (10 pages).
Sharma et al. (Dec. 2009) "Intranasal Cabergoline: Pharmacokinetic and Pharmacodynamic Studies", AAPS PharmSciTech, 10(4):1321-1330.
Thiel Karl A. (May 2004) "Structure-Aided Drug Design's Next Generation", Nature Biology, 22(5):513-519.
Tittarelli et al. (2015) "Recreational Use, Analysis and Toxicity of Tryptamines", Current Neuropharmacology, 13(1):26-46.
Vargas et al. (Oct. 2021) "Psychedelics and Other Psychoplastogens for Treating Mental Illness", Frontiers in Psychiatry, 12:1-19.
Zetler et al. (Jan. 1968) Die Wirkung von 11 Indol-Alkaloiden auf das Meerschweinchen-Herz in vivo und in vitro, verglichen mit 2 synthetischen Azepinoindolen, Chinidin und Quindonium, Naunyn-Schmiedebergs Archiv für Pharmakologie und experimentelle Pathologie, 260:26-49.
Zetler et al. (1970) "Inhibition of Cardiac Effects of Noradrenaline by Eleven Indole Alkaloids, Two Azepinoindoles, Quinidine, Quindonium, and Propranolol", Pharmacology, 4(3):129-142.
Zetler et al. (1972) "Refractory Period and Strophanthin Actions, as Influenced by Four Indole Alkaloids and Two Synthetic Azepinoindoles", Pharmacology, 8:235-243.
Nov. 16, 1984) "Database Registry, Chemical Abstracts Services, CAS Registry No. 7546-76-1", CAS.
2016) PUBCHEM-SID-274223890, 5 pages.
Abate et al. (2005) "Interaction of Chiral MS-245 Analogs at h5-HT6 Receptors", Bioorganic & medicinal chemistry letters, 15(15):3510-3513.

(56) References Cited

OTHER PUBLICATIONS

Church et al. (2013) "Ecstasy' Enhances Noise-induced Hear", Hearing Research, 302:96-106.
Dong et al. (May 2021) "Psychedelic-Inspired Drug Discovery Using an Engineered Biosensor", Cell, 184(10):2779-2792.
Eiter et al. (1952) "Zur Konstitution des Folicanthins: II. Mitteilung uber Folicanthin, ein neues Alkaloid aus den Blattern des Calycanthus floridus L", Monastshefte Fur Chemies—Chemical Monthly, 83(6):1453-1476.
Fitzgerald et al. (1999) "High-Affinity Agonist Binding Correlates with Efficacy (Intrinsic Activity) at the Human Serotonin 5-HT2A and 5-HT2C Receptors: Evidence Favoring the Ternary Complex and Two-State Models of Agonist Action", Journal of Neurochemistry, 72(5):2127-2134.
Huang et al. (2005) "Comparison of the Use of Aqueous and Nonaqueous Buffers in Association with Cyclodextrin for the Chiral Separation of 3,4-methylenedioxymethamphetamine and Related Compounds", Electrophoresis, 26(20):3904-3909.
Lacivita et al. (2006) "Selective Agents for Serotonin (2C) (5-HT2C) Receptor", Current Topics in Medicinal Chemistry, 6(18):1927-1970.
Masuda et al. (2000) "The Effect of Globopentaosylceramide on a Depression Model, Mouse Forced Swimming", The Tohoku Journal of Experimental Medicine, 191(1):47-54.
Pieroni et al. (2015) "Rational Design and Synthesis of Thioridazine Analogues as Enhancers of the Antituberculosis Therapy", Journal of medicinal chemistry, 58(15):5842-5853(43 pages).
Sanches et al. (2016) "Antidepressant Effects of a Single Dose of Ayahuasca in Patients with Recurrent Depression: A SPECT Study", Journal of Clinical Psychopharmacology, 36(1):77-81.
Teruya (1967) "Studies on 2-benzimidazolethiol derivatives. V. Structure-activity Relationship On Analgesic Action of 1-(dialkylamino-alkyl)-2-(p-ethoxyphenylthio)benzimidazole", Journal of the Pharmaceutical Society of Japan, 87(3):301-309.
Whitehouse et al. (2019) "Development of Inhibitors against *Mycobacterium* Abscessus tRNA (m1G37) Methyltransferase (TrmD) Using Fragment-Based Approaches", Journal of medicinal chemistry, 62(15):7210-7232.
Zubenko et al. (Apr. 17, 2019) "Pyridine-Azepine Structural Modification of 3,4-Dihydro-nor-isoharmine", Russian Journal of Organic Chemistry, 55(1):74-82.
(Nov. 16, 1984) "CAS Registry No. 7546-73-8, Chemical Abstracts Services", 2 pages.
(Nov. 16, 1984) "CAS Registry No. 7546-75-0, Chemical Abstracts Services", 2 pages.
(Nov. 16, 1984) "CAS Registry No. 7546-72-7, Chemical Abstracts Services", 2 pages.
(Nov. 27, 2012) "CAS Registry No. 1407483-64-0, Chemical Abstracts Services", 2 pages.
(Jan. 10, 2013) "CAS Registry No. 1416330-38-5, Chemical Abstracts Services", 2 pages.
(Apr. 16, 2002) "CAS Registry No. 405312-66-5, Chemical Abstracts Services", 2 pages.
(Nov. 16, 1984) "CAS Registry No. 7546-69-2, Chemical Abstracts Services", 2 pages.
(Dec. 26, 2004) CAS Registry No. 802581-10-8, Chemical Abstracts Services, 2 pages.
International Search Report and Written Opinion for PCT/US2022/079217 mailed on Feb. 1, 2023, 9 pages.
Supplementary European Search Report and Search Opinion for PCT/US2020/019858 mailed on Mar. 11, 2022, 10 pages.
International Search Report and Written Opinion for PCT/US2022/081927 mailed on Apr. 17, 2023, 11 pages.
Chen, et al. (Apr. 2022) "Iboga-type Alkaloids with Indolizidino[8,7-b]Indole Scaffold and Bisindole Alkaloids from Tabernaemontana Bufalina Lour", Phytochemistry, 196:113089.
International Search Report and Written Opinion for PCT/US2023/073837, mailed on Jan. 26, 2024, 9 pages.
International Search Report and Written Opinion for PCT/US2024/050417, mailed Jan. 16, 2025, 11 pages.
International Search Report and Written Opinion received for PCT/US2024/050418, Feb. 5, 2025, 12 pages.
Third Party Observations received for European Application No. 17857489.3, Jan. 10, 2024, 7 pages.
Blair et al. (2000) "Effect of Ring Fluorination on the Pharmacology of Hallucinogenic Tryptamines", Journal of Medicinal Chemistry, 43(24):4701-4710.
Carman et al. (1976) "Negative Effects of Melatonin on Depression", The American Journal of Psychiatry, 133(10):1181-1186.
Colley Claire, "This is What it Feels Like to Treat Depression with Magic Mushrooms", https://www.vice.com/en/article/8gk5wz/microdosing-psilocybin-depression-184, Sep. 7, 2015, 10 pages.
Database Registry, "CAS Registry No. 1347326-94-6", Chemical Abstracts Services, Dec. 2, 2011, 1 page.
Database Registry, "CAS Registry No. 1499823-45-8", Chemical Abstracts Services, Dec. 20, 2013, 2 pages.
Database Registry, "CAS Registry No. 1501213-32-6", Chemical Abstracts Services, Dec. 23, 2013, 2 pages.
Database Registry, "CAS Registry No. 1502739-86-7", Chemical Abstracts Services, Dec. 24, 2013, 2 pages.
Database Registry, "CAS Registry No. 1503723-45-2", Chemical Abstracts Services, Dec. 25, 2013, 2 pages.
Database Registry, "CAS Registry No. 1505385-98-7", Chemical Abstracts Services, Dec. 27, 2013, 2 pages.
Database Registry, "CAS Registry No. 1509251-72-2", Chemical Abstracts Services, Jan. 2, 2014, 2 pages.
Database Registry, "CAS Registry No. 1513834-45-1", Chemical Abstracts Services, Jan. 7, 2014, 2 pages.
Database Registry, "CAS Registry No. 1513937-46-6", Chemical Abstracts Services, Jan. 8, 2014, 2 pages.
Database Registry, "CAS Registry No. 1514378-08-5", Chemical Abstracts Services, Jan. 2014, 2 pages.
Database Registry, "CAS Registry No. 1515073-46-7", Chemical Abstracts Services, Jan. 9, 2014, 2 pages.
Database Registry, "CAS Registry No. 1515565-33-9", Chemical Abstracts Services, Jan. 9, 2014, 2 pages.
Database Registry,"CAS Registry No. 1516490-69-9", Chemical Abstracts Services, Jan. 10, 2014, 2 pages.
Database Registry, "CAS Registry No. 1519408-31-1", Chemical Abstracts Services, Jan. 14, 2014, 2 pages.
Database Registry, "CAS Registry No. 1521620-08-5", Chemical Abstracts Services, Jan. 16, 2014, 2 pages.
Database Registry, "CAS Registry No. 1523634-22-1", Chemical Abstracts Services, Jan. 19, 2014, 2 pages.
Database Registry, "CAS Registry No. 1524903-93-2", Chemical Abstracts Services, Jan. 20, 2014, 2 pages.
Database Registry, "CAS Registry No. 1525468-14-7", Chemical Abstracts Services, Jan. 20, 2014, 2 pages.
Database Registry, "CAS Registry No. 1533723-14-6", Chemical Abstracts Services, Jan. 30, 2014, 2 pages.
Database Registry, "CAS Registry No. 1533998-25-2", Chemical Abstracts Services, Jan. 30, 2014, 2 pages.
Database Registry, "CAS Registry No. 1540077-46-0", Chemical Abstracts Services, Feb. 9, 2014, 2 pages.
Database Registry, "CAS Registry No. 1540652-24-1", Chemical Abstracts Services, Feb. 10, 2014, 2 pages.
Database Registry, "CAS Registry No. 15918-67-9", Chemical Abstracts Services, Nov. 16, 1984, 2 pages.
Database Registry, "CAS Registry No. 15918-68-0", Chemical Abstracts Services, Nov. 16, 1984, 2 pages.
Database Registry, "CAS Registry No. 15918-91-9", Chemical Abstracts Services, Nov. 16, 1984, 2 pages.
Database Registry, "CAS Registry No. 15923-19-0", Chemical Abstracts Services, Nov. 16, 1984, 2 pages.
Database Registry, "CAS Registry No. 1779925-03-9", Chemical Abstracts Services, Jun. 14, 2015, 2 pages.
Database Registry, "CAS Registry No. 1781710-62-0", Chemical Abstracts Services, Jun. 17, 2015, 2 pages.
Database Registry, "CAS Registry No. 1781798-70-6", Chemical Abstracts Services, Jun. 17, 2015, 2 pages.
Database Registry, "CAS Registry No. 1781904-21-9", Chemical Abstracts Services, Jun. 17, 2015, 2 pages.

(56) References Cited

OTHER PUBLICATIONS

Database Registry, "CAS Registry No. 1781908-34-6", Chemical Abstracts Services, Jun. 17, 2015, 2 pages.
Database Registry, "CAS Registry No. 1782881-47-3", Chemical Abstracts Services, Jun. 17, 2015, 2 pages.
Database Registry, "CAS Registry No. 1784120-59-7", Chemical Abstracts Services, Jun. 19, 2015, 2 pages.
Database Registry, "CAS Registry No. 1785609-23-5", Chemical Abstracts Services, Jun. 21, 2015, 2 pages.
Database Registry, "CAS Registry No. 2072109-20-5", Chemical Abstracts Services, Feb. 17, 2017, 2 pages.
Database Registry, "CAS Registry No. 2072109-30-7", Chemical Abstracts Services, Feb. 17, 2017, 2 pages.
Database Registry, "CAS Registry No. 405305-92-2", Chemical Abstracts Services, Apr. 16, 2002, 2 pages.
Database Registry, "CAS Registry No. 405305-95-5", Chemical Abstracts Services, Apr. 16, 2002, 2 pages.
Database Registry, "CAS Registry No. 405311-77-5", Chemical Abstracts Services, Apr. 16, 2002, 2 pages.
Database Registry, "CAS Registry No. 685503-57-5", Chemical Abstracts Services, May 24, 2004, 2 pages.
Database Registry, "CAS Registry No. 736129-10-5", Chemical Abstracts Services, Aug. 31, 2004, 2 pages.
Database Registry, "CAS Registry No. 755746-20-4", Chemical Abstracts Services, Oct. 1, 2004, 2 pages.
Database Registry, "CAS Registry No. 757934-75-1", Chemical Abstracts Services, Oct. 7, 2004, 2 pages.
Database Registry, "CAS Registry No. 770702-18-6", Chemical Abstracts Services, Oct. 28, 2004, 2 pages.
Database Registry, "CAS Registry No. 778568-40-4", Chemical Abstracts Services, Nov. 11, 2004, 2 pages.
Database Registry, "CAS Registry No. 780030-99-1", Chemical Abstracts Services, Nov. 14, 2004, 2 pages.
Loach et al. (2014) "C7-Derivatization of C3-alkylindoles Including Tryptophans and Tryptamines", The Journal of Organic Chemistry, 79:11254-11263.
Mantegani et al. (1998) "5 (10→ 9) Abeo-ergoline Derivatives: Synthesis, 5-HT1A-receptor Affinity and Selectivity", European Journal of Medicinal Chemistry, 33(4), 279-292.
Marek et al. (1989) "Evidence for Involvement of 5-Hydroxytryptaminei Receptors in Antidepressant-Like Drug Effects on Differential-Reinforcement-of-Low-Rate 72-Second Behavior", The Journal of Pharmacology and Experimental Therapeutics, 250(1):60-71.
Nichols Davide. (2018) "Dark Classics in Chemical Neuroscience: Lysergic Acid Diethylamide (LSD)", ACS chemical neuroscience, 9(10):2331-2343.
Pubchem, (2021) "5-Bromo-6-chloro-N,Ndiethylnicotinamide", SID-441175770, 5 pages.
Pubchem, (2018) "SID-368776104", 5 pages.
Ray Thomas S. (2010) "Psychedelics and the Human Receptorome", PLOS One, 5(2):1-17.
Turton et al. (2014) "A Qualitative Report on the Subjective Experience of Intravenous Psilocybin Administered in an fMRI Environment", Current Drug Abuse Reviews, 7(2):117-127.
Unknown, (2005) "Chapter 11: Serotonin and Histamine. In Shao Fuyuan and Wang Yuhui (Eds.)", Molecular Neuropharmacology, Shanghai Science and Technology Press, 4th ed., pp. 261-263.
Unknown, (2015) "Chapter 5: Pathogenesis of Alzheimer's disease and progress in drug research", In Wang X. (Ed.), Practical Molecular Pharmacology, Peking Union Medical College Press, ISBN 978-7-5679-0411-8., 2nd ed., pp. 127.
Ward et al. (1988) "Ergolines as Selective 5-HT1 Agonists", J Med Chem., 31(8):1512-1519.
Supplementary European Search Report and Search Opinion for PCT/US2022024626, mailed Aug. 4, 2025, 6 pages.

* cited by examiner

PATH B

Leonardo C.(1966). "The reduction of tosylhydrazones and of acyl tosylhydrazides". Tetrahedron. 22 (2): 487–493.

ERGOLINE-LIKE COMPOUNDS FOR PROMOTING NEURAL PLASTICITY

CROSS-REFERENCES TO RELATED APPLICATIONS

This application claims priority to U.S. Provisional Application No. 62/914,807 filed Oct. 14, 2019, which is incorporated herein in its entirety for all purposes.

STATEMENT AS TO RIGHTS TO INVENTIONS MADE UNDER FEDERALLY SPONSORED RESEARCH AND DEVELOPMENT

This invention was made with Government support under Grant No. R01GM128997 awarded by the National Institutes of Health. The Government has certain rights in this invention.

BACKGROUND

Altered synaptic connectivity and plasticity has been observed in the brains of individuals with neurological diseases and disorders. Psychoplastogens promote neuronal growth and improve neuronal architecture through mechanisms involving the activation of the serotonin 5-$HT_{2A}$ and 5-$HT_{2C}$ receptors. Modulators of these biological targets, such as, for example, N,N-dimethyltryptamine (DMT), ibogaine, and lysergic acid diethylamide (LSD) have demonstrated psychoplastogenic properties. For example, LSD and other analogs of the ergoline scaffold are capable of rectifying deleterious changes in neuronal structure that are associated with neurological diseases and disorders. Such structural alterations include, for example, the loss of dendritic spines and synapses in the prefrontal cortex (PFC) as well as reductions in dendritic arbor complexity. Furthermore, pyramidal neurons in the PFC exhibit top-down control over areas of the brain controlling motivation, fear, and reward. Psychedelic psychoplastogens have demonstrated antidepressant, anxiolytic, and anti-addictive effects in the clinic.

Provided herein are compounds with clinically relevant therapeutic efficacy that are easier to synthesize, have improved physicochemical properties, and possess reduced hallucinogenic (e.g., non-hallucinogenic) properties as compared to their hallucinogenic (e.g., ergoline) counterparts.

BRIEF SUMMARY OF THE INVENTION

In one embodiment, provided herein is a compound, or a pharmaceutically acceptable salt thereof, having a structure of Formula (Ia) or Formula (Ib):

(Ia)

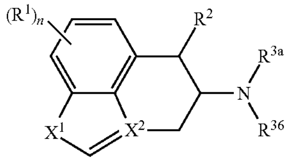

(Ib)

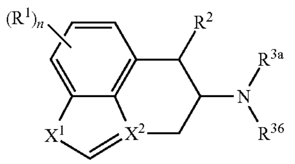

wherein: $X^1$ and $X^2$ are each independently C, CH, $CH_2$, N, or NH; each $R^1$ is independently hydrogen, $C_{1-6}$ alkyl, $C_{2-6}$ alkenyl, $C_{2-6}$ alkynyl, $C_{1-6}$ alkoxy, $C_{1-6}$ alkoxyalkyl, halogen, $C_{1-6}$ haloalkyl, $C_{1-6}$ haloalkoxy, —$NO_2$, or —CN; alternatively, two $R^1$ groups on adjacent ring atoms are combined to form a 4 to 8 membered heterocycloalkyl having 1 to 2 heteroatoms, each independently N, O, or S; $R^2$ is hydrogen or =O; $R^{3a}$ and $R^{3b}$ are each independently hydrogen, $C_{1-6}$ alkyl, or $C_{1-6}$ haloalkyl; alternatively, $R^{3a}$ is combined with $R^{3b}$ and the atom to which they are attached to form a 3 to 8 membered heterocycloalkyl having 1 to 2 heteroatoms, each independently N, O, or S; alternatively, $R^2$ is combined with $R^{3a}$ and the atoms to which they are attached to form a 5 to 8 membered heterocycloalkyl having 1 to 2 heteroatoms, each independently N, O, or S, wherein the heterocycloalkyl is substituted with —C(O)N($R^{2a}$)($R^{2b}$); $R^{2a}$ and $R^{2b}$ are each independently hydrogen or $C_{1-6}$ alkyl; and subscript n is 0 to 3, wherein the compound is other than the following structures:

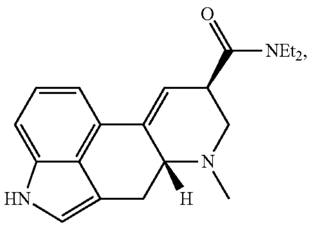

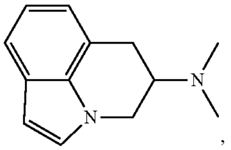

,

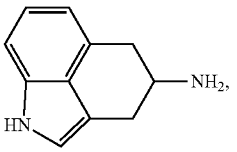

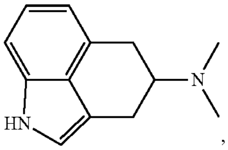

, and

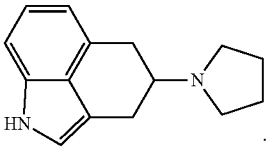

.

In another embodiment, provided herein is a compound, or a pharmaceutically acceptable salt thereof, having a structure of Formula (II):

(III)

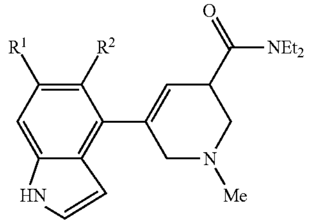

wherein: $R^1$ and $R^2$ are independently hydrogen, $C_{1-6}$ alkyl, $C_{2-6}$ alkenyl, $C_{2-6}$ alkynyl, $C_{1-6}$ alkoxy, $C_{1-6}$ alkoxyalkyl, halogen, $C_{1-6}$ haloalkyl, $C_{1-6}$ haloalkoxy, —$NO_2$, or —CN; alternatively, $R^1$ and $R^2$ are combined to form a 4 to 8 membered heterocycloalkyl having 1 to 2 heteroatoms, each independently N, O, or S.

In another embodiment, provided herein is a compound, or a pharmaceutically acceptable salt thereof, having a structure of Formula (IIIa) or Formula (IIIb):

(IIIa)

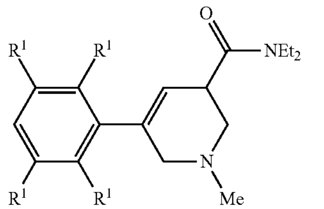

(IIIb)

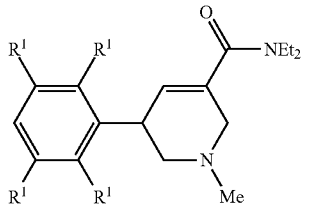

wherein: each $R^1$ is independently hydrogen, $C_{1-6}$ alkyl, $C_{2-6}$ alkenyl, $C_{2-6}$ alkynyl, $C_{1-6}$ alkoxy, $C_{1-6}$ alkoxyalkyl, halogen, $C_{1-6}$ haloalkyl, $C_{1-6}$ haloalkoxy, —$NO_2$, or —CN.

In another embodiment, provided herein is a pharmaceutical composition, comprising a therapeutically effective amount of a compound of the present invention, or a pharmaceutically acceptable salt thereof.

In another embodiment, provided herein is a method of treating a disease, comprising administering to a subject in need thereof, a therapeutically effective amount of a compound of the present invention, or a pharmaceutically acceptable salt thereof, thereby treating the disease.

In another embodiment, provided herein is a method for increasing neural plasticity, the method comprising contacting a neuronal cell with a compound of the present invention, or a pharmaceutically acceptable salt thereof, in an amount sufficient to increase neural plasticity of the neuronal cell, wherein the compound produces a maximum number of dendritic crossings with an increase of greater than 1.0 fold by a Sholl Analysis.

In another embodiment, provided herein is a method for increasing neural plasticity and increasing dendritic spine density, the method comprising contacting a neuronal cell with a compound of the present invention, or a pharmaceutically acceptable salt thereof, in an amount sufficient to increase neural plasticity and increase dendritic spine density of the neuronal cell.

DETAILED DESCRIPTION OF THE INVENTION

I. General

Figure 1:
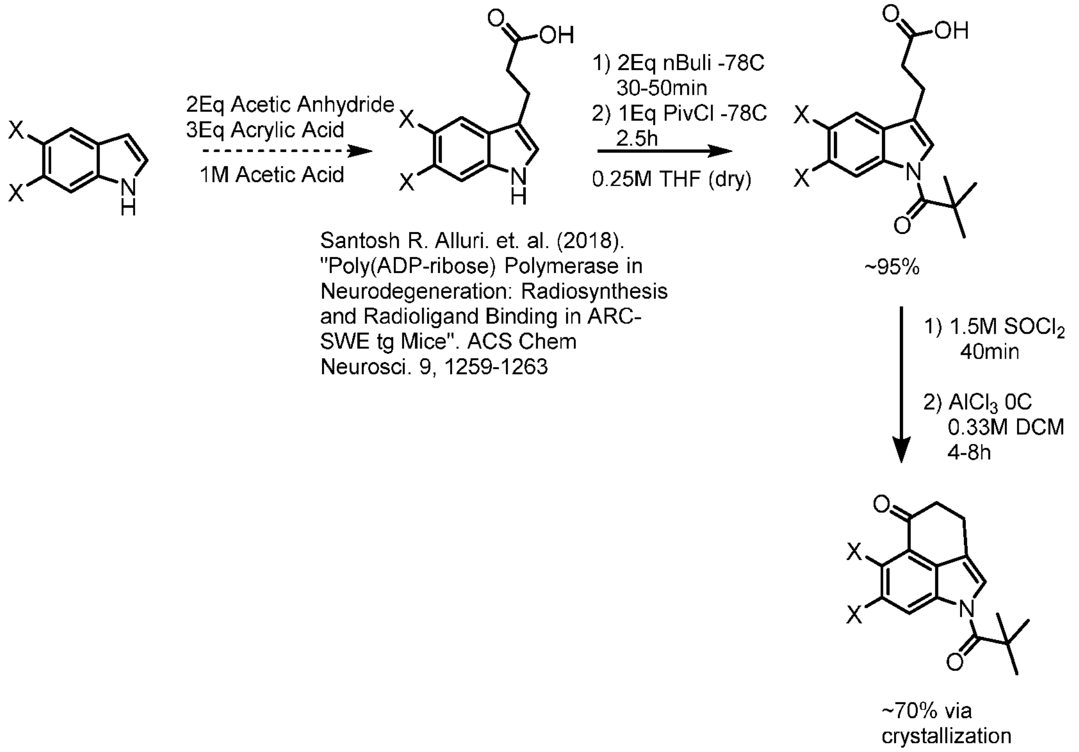
FIG. 1 shows synthetic path 1, to synthesize an intermediate final product. The intermediate final product can be used to synthesize compounds of Formula (Ia).
Figure 2:
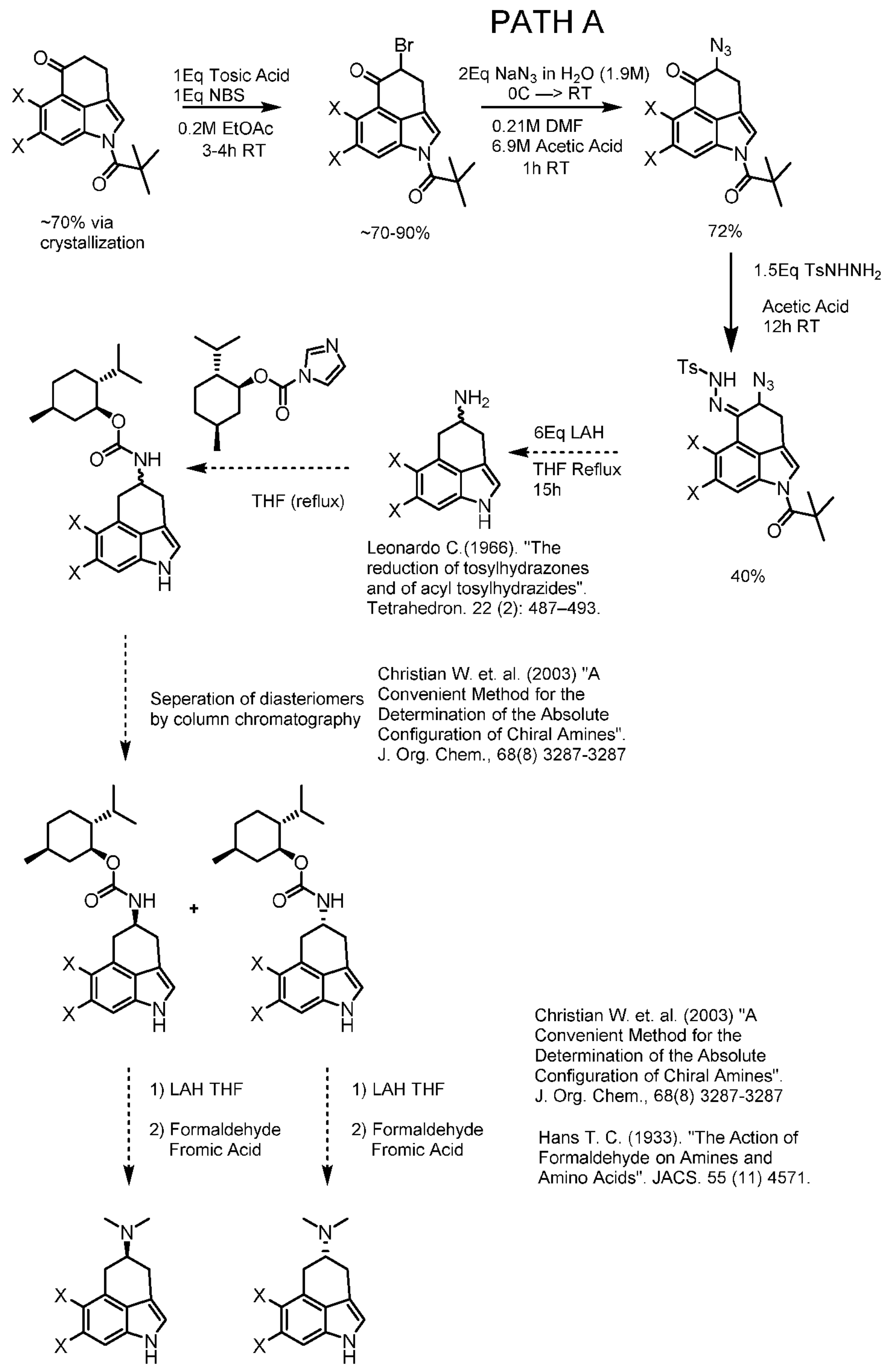
FIG. 2 shows synthetic path A, which is one synthetic route using the product from path 1 in FIG. 1 to synthesize a compound of Formula (Ia).
Figure 3:
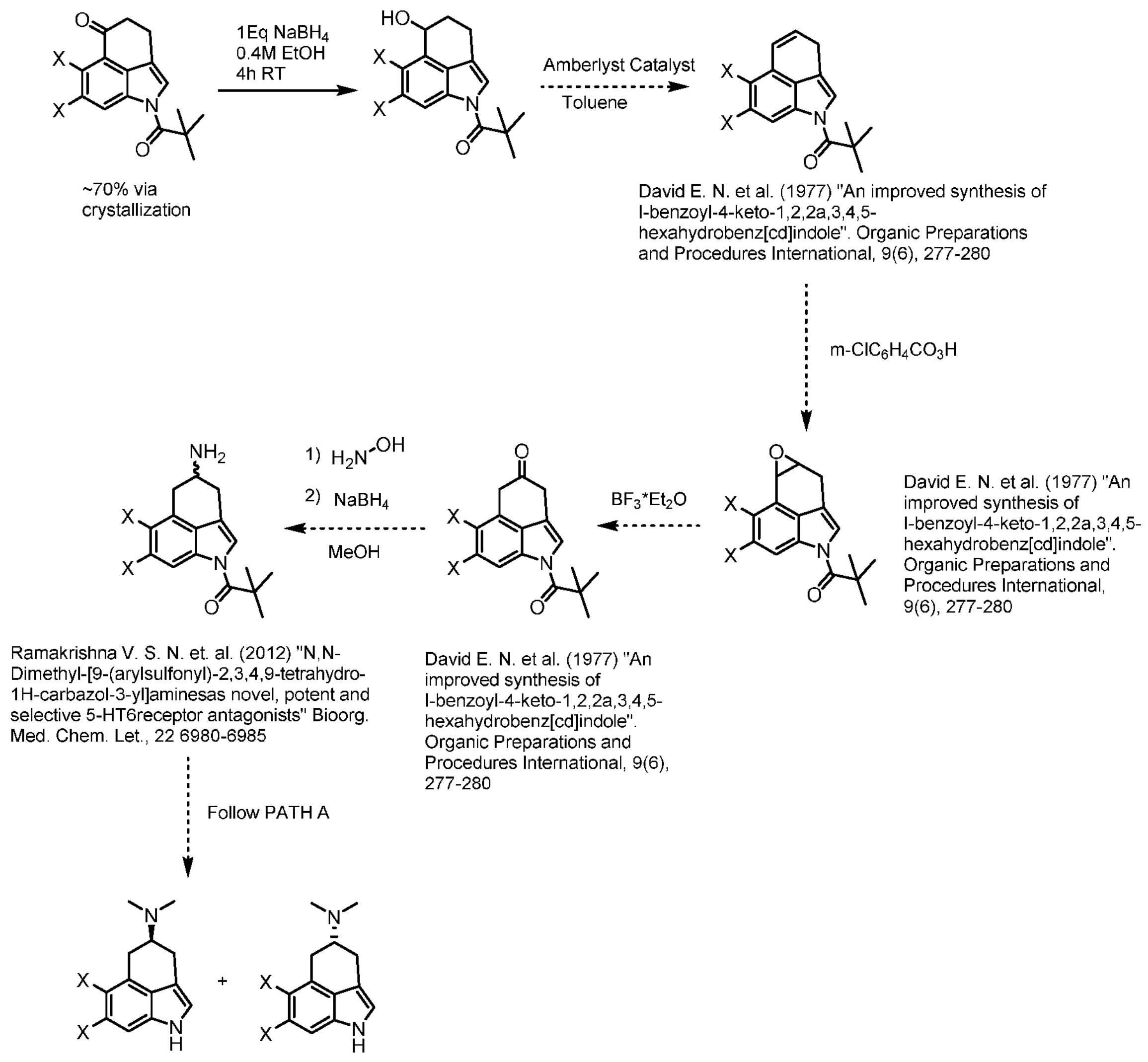
FIG. 3 shows synthetic path B, which is another synthetic route using the product from path 1 in FIG. 1 to synthesize a compound of Formula (Ia).
Figure 4:
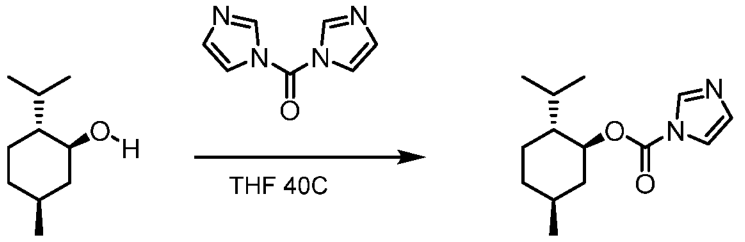
FIG. 4 shows the synthesis of an intermediate used in path A.
Figure 5:
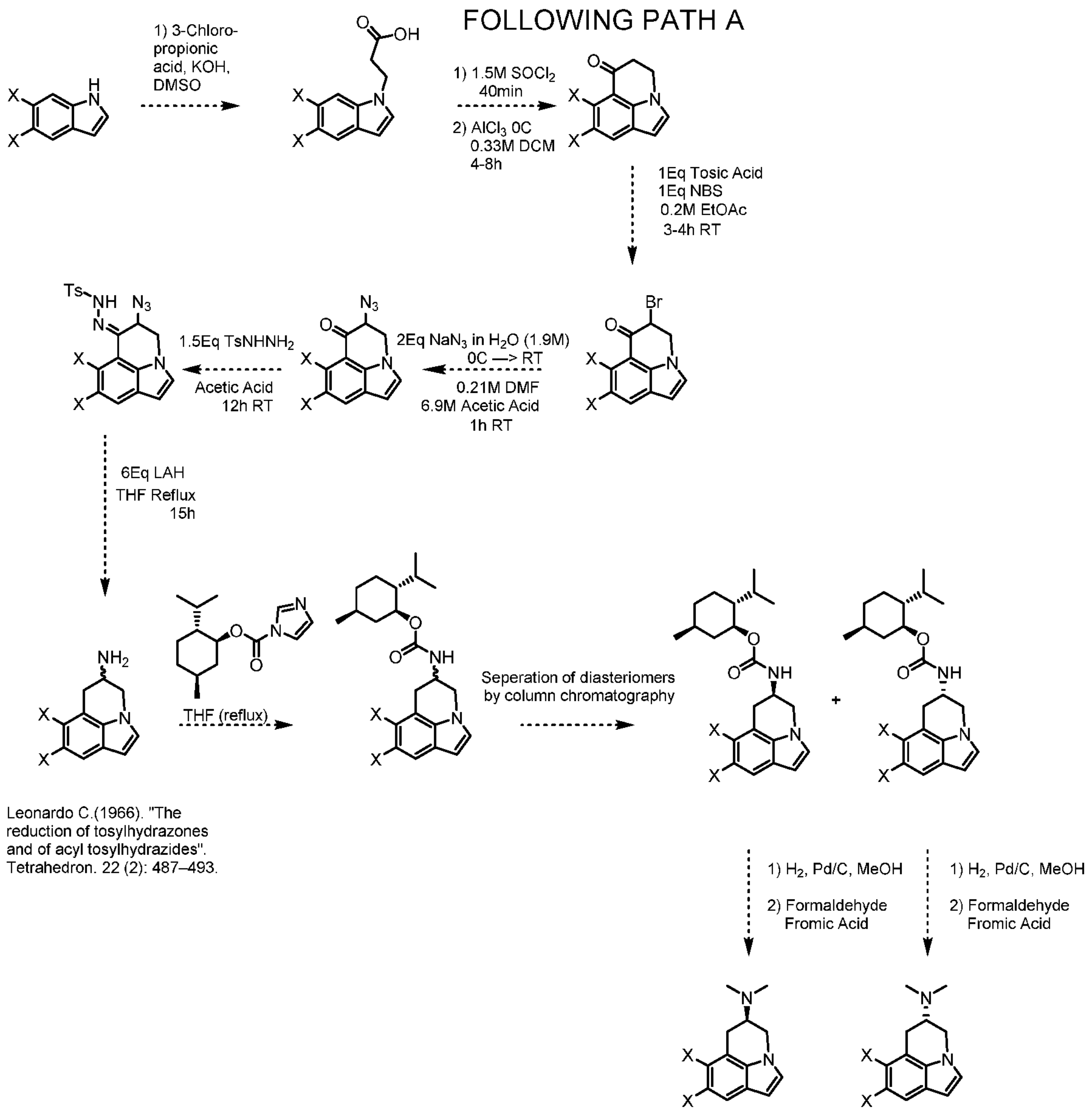
FIG. 5 shows synthetic path 2, which is one synthetic route for synthesizing compounds of Formula (Ib).
Figure 6A:
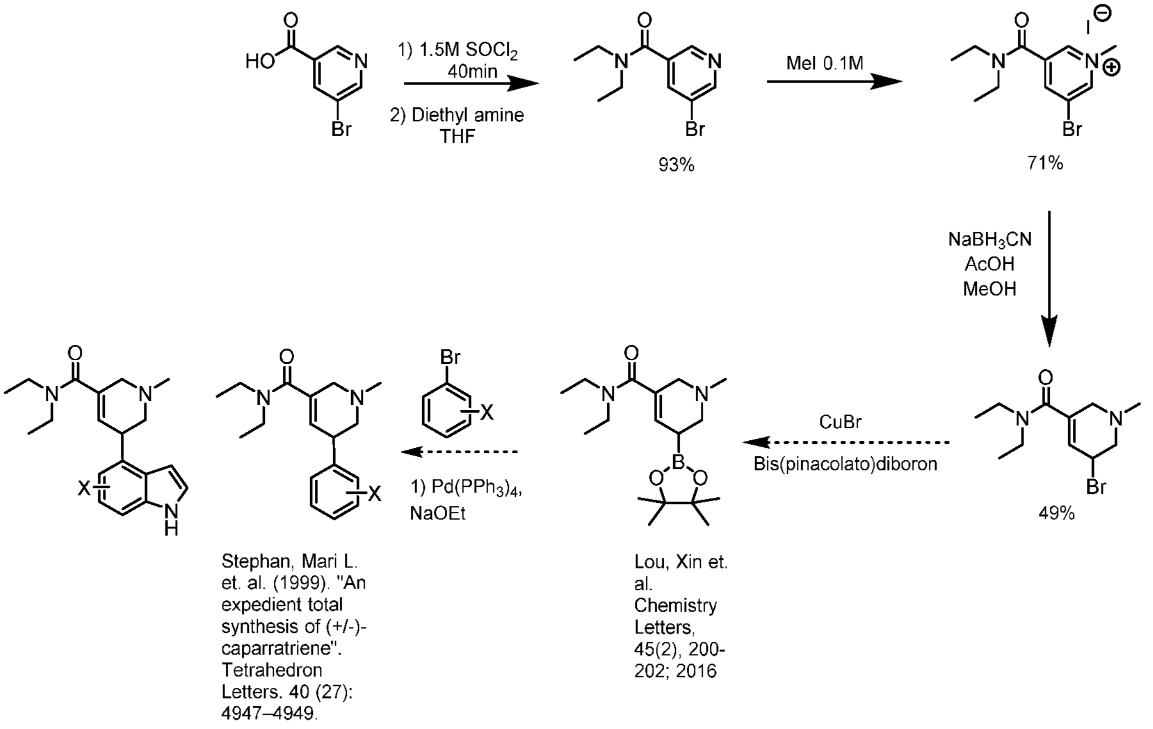
FIG. 6A shows synthetic path 3, which is one synthetic route for synthesizing compounds of Formula (IIb).
Figure 6B:
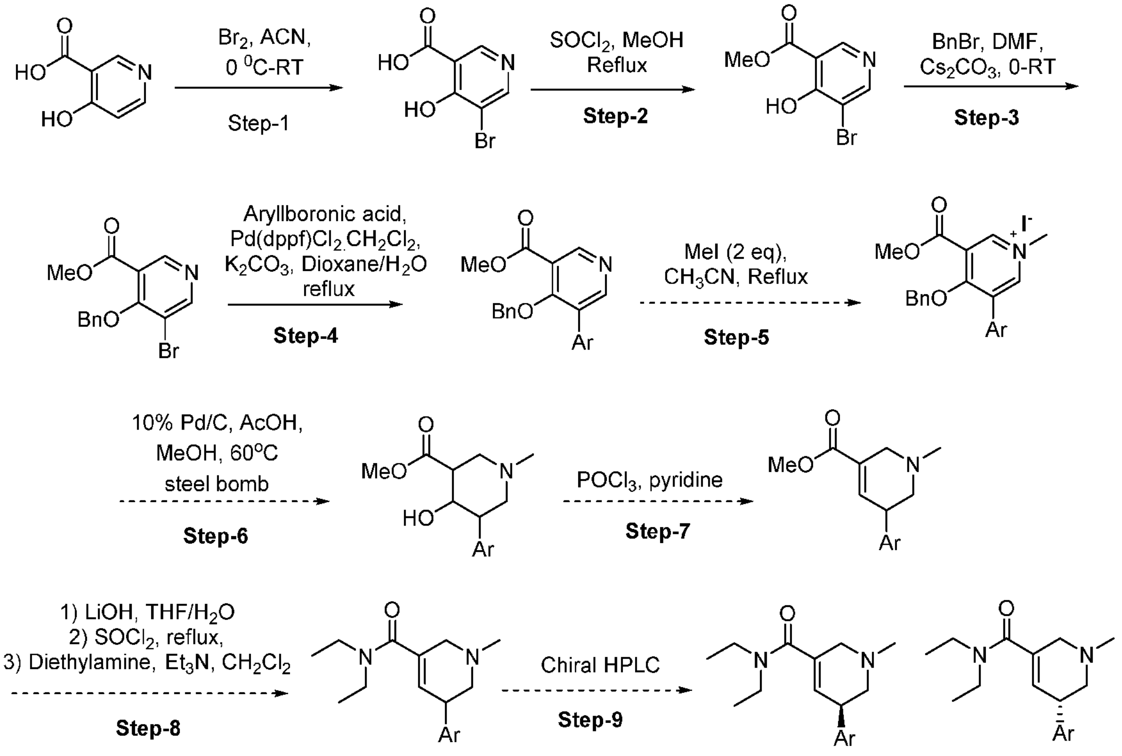
FIG. 6B shows synthetic path 4, which is another synthetic route for synthesizing compounds of Formula (IIb).
Figure 7:
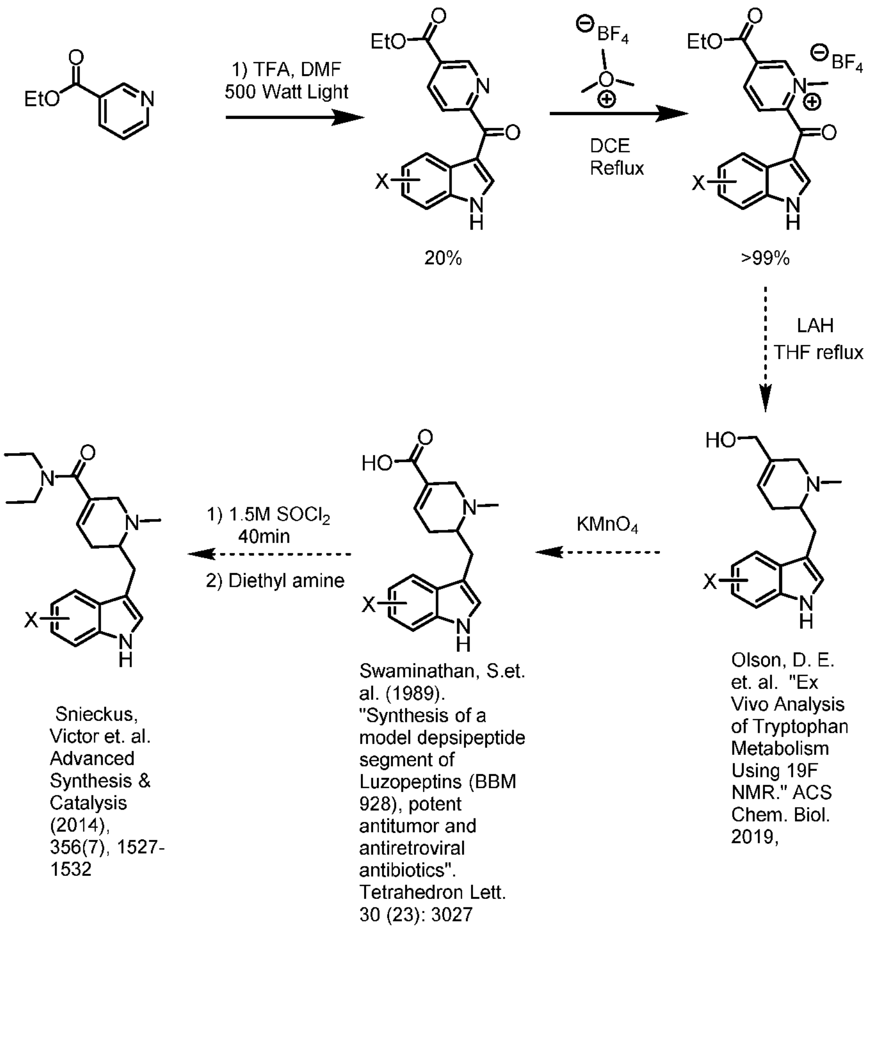
FIG. 7 shows synthetic path 5, which is one synthetic route for synthesizing compounds of Formula (Ig).

Provided herein is ergoline-derived heterocyclic compounds. The compounds of the present invention are useful for treatment of diseases, such as brain disorders and other neurological diseases. The compounds of the present invention are also useful for increasing neural plasticity, increasing dendritic spine density, or both.

II. Definitions

Unless specifically indicated otherwise, all technical and scientific terms used herein have the same meaning as commonly understood by those of ordinary skill in the art to which this invention belongs. In addition, any method or material similar or equivalent to a method or material described herein can be used in the practice of the present invention. For purposes of the present invention, the following terms are defined.

"A," "an," or "the" not only include aspects with one member, but also include aspects with more than one member. For instance, the singular forms "a," "an," and "the" include plural referents unless the context clearly dictates otherwise. Thus, for example, reference to "a cell" includes a plurality of such cells and reference to "the agent" includes reference to one or more agents known to those skilled in the art, and so forth.

"Alkyl" refers to a straight or branched, saturated, aliphatic radical having the number of carbon atoms indicated. Disclosures provided herein of an "alkyl" are intended to include independent recitations of a saturated alkyl, unless otherwise stated. Alkyl groups described herein are generally monovalent, but may also be divalent which may also be described herein as "alkylene" or "alkylenyl" groups. Alkyl can include any number of carbons, such as $C_{1-2}$, $C_{1-3}$, $C_{1-4}$, $C_{1-5}$, $C_{1-6}$, $C_{1-7}$, $C_{1-8}$, $C_{1-9}$, $C_{1-10}$, $C_{2-3}$, $C_{2-4}$, $C_{2-5}$, $C_{2-6}$, $C_{3-4}$, $C_{3-5}$, $C_{3-6}$, $C_{4-5}$, $C_{4-6}$ and $C_{5-6}$. For example, $C_{1-6}$ alkyl includes, but is not limited to, methyl, ethyl, propyl, isopropyl, butyl, isobutyl, sec-butyl, tert-butyl, pentyl, isopentyl, hexyl, etc. Alkyl can also refer to alkyl groups having up to 20 carbons atoms, such as, but not limited to heptyl, octyl, nonyl, decyl, etc. Alkyl groups can be substituted or unsubstituted.

"Alkenyl" refers to a straight chain or branched hydrocarbon having at least 2 carbon atoms and at least one double bond. Alkenyl can include any number of carbons, such as $C_2$, $C_{2-3}$, $C_{2-4}$, $C_{2-5}$, $C_{2-6}$, $C_{2-7}$, $C_{2-8}$, $C_{2-9}$, $C_{2-10}$, $C_3$, $C_{3-4}$, $C_{3-5}$, $C_{3-6}$, $C_4$, $C_{4-5}$, $C_{4-6}$, $C_5$, $C_{5-6}$, and $C_6$. Alkenyl groups can have any suitable number of double bonds, including, but not limited to, 1, 2, 3, 4, 5 or more. Examples of alkenyl groups include, but are not limited to, vinyl (ethenyl), propenyl, isopropenyl, 1-butenyl, 2-butenyl, isobutenyl, butadienyl, 1-pentenyl, 2-pentenyl, isopentenyl, 1,3-pentadienyl, 1,4-pentadienyl, 1-hexenyl, 2-hexenyl, 3-hexenyl, 1,3-hexadienyl, 1,4-hexadienyl, 1,5-hexadienyl, 2,4-hexadienyl, or 1,3,5-hexatrienyl. Alkenyl groups can be substituted or unsubstituted.

"Alkynyl" refers to either a straight chain or branched hydrocarbon having at least 2 carbon atoms and at least one triple bond. Alkynyl can include any number of carbons, such as $C_2$, $C_{2-3}$, $C_{2-4}$, $C_{2-5}$, $C_{2-6}$, $C_{2-7}$, $C_{2-8}$, $C_{2-9}$, $C_{2-10}$, $C_3$, $C_{3-4}$, $C_{3-5}$, $C_{3-6}$, $C_4$, $C_{4-5}$, $C_{4-6}$, $C_5$, $C_{5-6}$, and $C_6$. Examples of alkynyl groups include, but are not limited to, acetylenyl, propynyl, 1-butynyl, 2-butynyl, butadiynyl, 1-pentynyl, 2-pentynyl, isopentynyl, 1,3-pentadiynyl, 1,4-pentadiynyl, 1-hexynyl, 2-hexynyl, 3-hexynyl, 1,3-hexadiynyl, 1,4-hexadiynyl, 1,5-hexadiynyl, 2,4-hexadiynyl, or 1,3,5-hexatriynyl. Alkynyl groups can be substituted or unsubstituted.

"Alkoxy" refers to an alkyl group having an oxygen atom that connects the alkyl group to the point of attachment: alkyl-O—. As for alkyl group, alkoxy groups can have any suitable number of carbon atoms, such as $C_{1-6}$. Alkoxy groups include, for example, methoxy, ethoxy, propoxy, iso-propoxy, butoxy, 2-butoxy, iso-butoxy, sec-butoxy, tert-butoxy, pentoxy, hexoxy, etc. The alkoxy groups can be further substituted with a variety of substituents described within. Alkoxy groups can be substituted or unsubstituted.

"Alkoxyalkyl" refers to a radical having an alkyl component and an alkoxy component, where the alkyl component links the alkoxy component to the point of attachment. The alkyl component is as defined above, except that the alkyl component is at least divalent, an alkylene, to link to the alkoxy component and to the point of attachment. The alkyl component can include any number of carbons, such as $C_{0-6}$, $C_{1-2}$, $C_{1-3}$, $C_{1-4}$, $C_{1-5}$, $C_{1-6}$, $C_{2-3}$, $C_{2-4}$, $C_{2-5}$, $C_{2-6}$, $C_{3-4}$, $C_{3-5}$, $C_{3-6}$, $C_{4-5}$, $C_{4-6}$ and $C_{5-6}$. In some instances, the alkyl component can be absent. The alkoxy component is as defined above. Examples of the alkoxyalkyl group include, but are not limited to, 2-ethoxy-ethyl and methoxymethyl.

"Halogen" refers to fluorine, chlorine, bromine and iodine.

"Haloalkyl" refers to alkyl, as defined above, where some or all of the hydrogen atoms are replaced with halogen atoms. As for alkyl group, haloalkyl groups can have any suitable number of carbon atoms, such as $C_{1-6}$. For example, haloalkyl includes trifluoromethyl, fluoromethyl, etc. In some instances, the term "perfluoro" can be used to define a compound or radical where all the hydrogens are replaced with fluorine. For example, perfluoromethyl refers to 1,1,1-trifluoromethyl.

"Haloalkoxy" refers to an alkoxy group where some or all of the hydrogen atoms are substituted with halogen atoms. As for an alkyl group, haloalkoxy groups can have any suitable number of carbon atoms, such as $C_{1-6}$. The alkoxy groups can be substituted with 1, 2, 3, or more halogens. When all the hydrogens are replaced with a halogen, for example by fluorine, the compounds are per-substituted, for example, perfluorinated. Haloalkoxy includes, but is not limited to, trifluoromethoxy, 2,2,2,-trifluoroethoxy, perfluoroethoxy, etc.

"Cycloalkyl" refers to a saturated or partially unsaturated, monocyclic, fused bicyclic or bridged polycyclic ring assembly containing from 3 to 12 ring atoms, or the number of atoms indicated. Cycloalkyl can include any number of carbons, such as $C_{3-6}$, $C_{4-6}$, $C_{5-6}$, $C_{3-8}$, $C_{4-8}$, $C_{5-8}$, $C_{6-8}$, $C_{3-9}$, $C_{3-10}$, $C_{3-11}$, and $C_{3-12}$. In some embodiments, cycloalkyls are spirocyclic or bridged compounds. In some embodiments, cycloalkyls are optionally fused with an aromatic ring, and the point of attachment is at a carbon that is not an aromatic ring carbon atom. Saturated monocyclic cycloalkyl rings include, for example, cyclopropyl, cyclobutyl, cyclopentyl, cyclohexyl, and cyclooctyl. Saturated bicyclic and polycyclic cycloalkyl rings include, for example, norbornane, [2.2.2] bicyclooctane, decahydronaphthalene and adamantane. Cycloalkyl groups can also be partially unsaturated, having one or more double or triple bonds in the ring. Representative cycloalkyl groups that are partially unsaturated include, but are not limited to, cyclobutene, cyclopentene, cyclohexene, cyclohexadiene (1,3- and 1,4-isomers), cycloheptene, cycloheptadiene, cyclooctene, cyclooctadiene (1,3-, 1,4- and 1,5-isomers), norbornene, and norbornadiene. When cycloalkyl is a saturated monocyclic $C_{3-8}$ cycloalkyl, exemplary groups include, but are not limited to cyclopropyl, cyclobutyl, cyclopentyl, cyclohexyl, cycloheptyl and cyclooctyl. When cycloalkyl is a saturated monocyclic $C_{3-6}$ cycloalkyl, exemplary groups include, but are not limited to cyclopropyl, cyclobutyl, cyclopentyl, and cyclohexyl. Cycloalkyl groups can be substituted or unsubstituted. Cycloalkyl groups can contain one or more double bonds in the ring.

"Heterocycloalkyl" refers to a saturated ring system having from 3 to 12 ring members and from 1 to 4 heteroatoms of N, O and S. The heteroatoms can also be oxidized, such as, but not limited to, —S(O)— and —$S(O)_2$—. Heterocycloalkyl groups can include any number of ring atoms, such as, 3 to 6, 4 to 6, 5 to 6, 3 to 8, 4 to 8, 5 to 8, 6 to 8, 3 to 9, 3 to 10, 3 to 11, or 3 to 12 ring members. Any suitable number of heteroatoms can be included in the heterocycloalkyl groups, such as 1, 2, 3, or 4, or 1 to 2, 1 to 3, 1 to 4, 2 to 3, 2 to 4, or 3 to 4. In some embodiments, heterocycloalkyls are spirocyclic or bridged compounds. In some embodiments, heterocycloalkyls are optionally fused with an aromatic ring, and the point of attachment is at a carbon or heteroatom (e.g., nitrogen atom) that is not an aromatic ring carbon atom. The heterocycloalkyl group can include groups such as aziridine, azetidine, pyrrolidine, piperidine, azepane, azocane, quinuclidine, pyrazolidine, imidazolidine, piperazine (1,2-, 1,3- and 1,4-isomers), oxirane, oxetane, tetrahydrofuran, oxane (tetrahydropyran), oxepane, thiirane, thietane, thiolane (tetrahydrothiophene), thiane (tetrahydrothiopyran), oxazolidine, isoxazolidine, thiazolidine, isothiazolidine, dioxolane, dithiolane, morpholine, thiomorpholine, dioxane, or dithiane. The heterocycloalkyl groups can also be fused to aromatic or non-aromatic ring systems to form members including, but not limited to, indoline. Heterocycloalkyl groups can be unsubstituted or substituted. For example, heterocycloalkyl groups can be substituted with $C_{1-6}$ alkyl or oxo (=O), among many others.

The heterocycloalkyl groups can be linked via any position on the ring. For example, aziridine can be 1- or 2-aziridine, azetidine can be 1- or 2-azetidine, pyrrolidine can be 1-, 2- or 3-pyrrolidine, piperidine can be 1-, 2-, 3- or 4-piperidine, pyrazolidine can be 1-, 2-, 3-, or 4-pyrazolidine, imidazolidine can be 1-, 2-, 3- or 4-imidazolidine, piperazine can be 1-, 2-, 3- or 4-piperazine, tetrahydrofuran can be 1- or 2-tetrahydrofuran, oxazolidine can be 2-, 3-, 4- or 5-oxazolidine, isoxazolidine can be 2-, 3-, 4- or 5-isoxazolidine, thiazolidine can be 2-, 3-, 4- or 5-thiazolidine, isothiazolidine can be 2-, 3-, 4- or 5-isothiazolidine, and morpholine can be 2-, 3- or 4-morpholine.

When heterocycloalkyl includes 3 to 8 ring members and 1 to 3 heteroatoms, representative members include, but are not limited to, pyrrolidine, piperidine, tetrahydrofuran, oxane, tetrahydrothiophene, thiane, pyrazolidine, imidazolidine, piperazine, oxazolidine, isoxzoalidine, thiazolidine, isothiazolidine, morpholine, thiomorpholine, dioxane and dithiane. Heterocycloalkyl can also form a ring having 5 to 6 ring members and 1 to 2 heteroatoms, with representative members including, but not limited to, pyrrolidine, piperidine, tetrahydrofuran, tetrahydrothiophene, pyrazolidine, imidazolidine, piperazine, oxazolidine, isoxazolidine, thiazolidine, isothiazolidine, and morpholine.

"Heterocycle" or "heterocyclic" refers to heteroaromatic rings (also known as heteroaryls) and heterocycloalkyl rings (also known as heteroalicyclic groups) containing one to four heteroatoms in the ring(s), where each heteroatom in the ring(s) is selected from 0, S and N, wherein each heterocyclic group has from 3 to 10 atoms in its ring system, and with the proviso that any ring does not contain two adjacent O or S atoms. Unless stated otherwise specifically in the specification, the heterocyclyl radical is a monocyclic, bicyclic, tricyclic or tetracyclic ring system, which optionally includes fused or bridged ring systems. The heteroatoms in the heterocyclyl radical are optionally oxidized. One or more nitrogen atoms, if present, are optionally quaternized. The heterocyclyl radical is partially or fully saturated. The heterocyclyl is attached to the rest of the molecule through any atom of the ring(s). Non-aromatic heterocyclic groups (also known as heterocycloalkyls) include rings having 3 to 10 atoms in its ring system and aromatic heterocyclic groups include rings having 5 to 10 atoms in its ring system. The heterocyclic groups include benzo-fused ring systems. Examples of non-aromatic heterocyclic groups are pyrrolidinyl, tetrahydrofuranyl, dihydrofuranyl, tetrahydrothienyl, oxazolidinonyl, tetrahydropyranyl, dihydropyranyl, tetrahydrothiopyranyl, piperidinyl, morpholinyl, thiomorpholinyl, thioxanyl, piperazinyl, aziridinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, pyrrolin-2-yl, pyrrolin-3-yl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3.1.0]hexanyl, 3-azabicyclo[4.1.0]heptanyl, 3H-indolyl, indolin-2-onyl, isoindolin-1-onyl, isoindoline-1,3-dionyl, 3,4-dihydroisoquinolin-1(2H)-onyl, 3,4-dihydroquinolin-2(1H)-onyl, isoindoline-1,3-dithionyl, benzo[d]oxazol-2(3H)-onyl, 1H-benzo[d]imidazol-2(3H)-onyl, benzo[d]thiazol-2(3H)-onyl, and quinolizinyl. Examples of aromatic heterocyclic groups are pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. The foregoing groups are either C-attached (or C-linked) or N-attached where such is possible. For instance, a group derived from pyrrole includes both pyrrol-1-yl (N-attached) or pyrrol-3-yl (C-attached). Further, a group derived from imidazole includes imidazol-1-yl or imidazol-3-yl (both N-attached) or imidazol-2-yl, imidazol-4-yl or imidazol-5-yl (all C-attached). The heterocyclic groups include benzo-fused ring systems. Non-aromatic heterocycles are optionally substituted with one or two oxo (=O) moieties, such as pyrrolidin-2-one. In some embodiments, at least one of the two rings of a bicyclic heterocycle is aromatic. In some embodiments, both rings of a bicyclic heterocycle are aromatic. Unless stated otherwise specifically in the specification, the term "heterocyclyl" is meant to include heterocyclyl radicals as defined above that are optionally substituted by one or more substituents selected from alkyl, alkenyl, alkynyl, halo, fluoroalkyl, oxo, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, $-R^y-OR^x$, $-R^y-OC(O)-R^x$, $-R^y-OC(O)-OR^x$, $-R^y-OC(O)-N(R^x)_2$, $-R^y-N(R^x)_2$, $-R^y-C(O)R^x$, $-R^y-C(O)OR^x$, $-R^y-C(O)N(R^x)_2$, $-R^y-O-R^z-C(O)N(R^x)_2$, $-R^y-N(R^x)C(O)OR^x$, $-R^y-N(R^x)C(O)R^x$, $-R^y-N(R^x)S(O)_tR^x$ (where t is 1 or 2), $-R^y-S(O)_tR^x$ (where t is 1 or 2), $-R^y-S(O)_tOR^x$ (where t is 1 or 2) and $-R^y-S(O)_tN(R^x)_2$ (where t is 1 or 2), where each $R^x$ is independently hydrogen, alkyl (optionally substituted with halogen, hydroxy, methoxy, or trifluoromethyl), fluoroalkyl, cycloalkyl (optionally substituted with halogen, hydroxy, methoxy, or trifluoromethyl), cycloalkylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl), each $R^y$ is independently a direct bond or a straight or branched alkylene or alkenylene chain, and $R^z$ is a straight or branched alkylene or alkenylene chain, and where each of the above substituents is unsubstituted unless otherwise indicated.

"Salt" refers to acid or base salts of the compounds used in the methods of the present invention. Illustrative examples of pharmaceutically acceptable salts are mineral acid (hydrochloric acid, hydrobromic acid, phosphoric acid, and the like) salts, organic acid (acetic acid, propionic acid, glutamic acid, citric acid and the like) salts, quaternary ammonium (methyl iodide, ethyl iodide, and the like) salts. It is understood that the pharmaceutically acceptable salts are non-toxic. Additional information on suitable pharmaceutically acceptable salts can be found in Remington's Pharmaceutical Sciences, 17th ed., Mack Publishing Company, Easton, Pa., 1985, which is incorporated herein by reference.

Pharmaceutically acceptable salts of the acidic compounds of the present invention are salts formed with bases, namely cationic salts such as alkali and alkaline earth metal salts, such as sodium, lithium, potassium, calcium, magnesium, as well as ammonium salts, such as ammonium, trimethyl-ammonium, diethylammonium, and tris-(hydroxymethyl)-methyl-ammonium salts.

Similarly acid addition salts, such as of mineral acids, organic carboxylic and organic sulfonic acids, e.g., hydrochloric acid, methanesulfonic acid, maleic acid, are also possible provided a basic group, such as pyridyl, constitutes part of the structure.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

"Therapeutically effective amount or dose" or "therapeutically sufficient amount or dose" or "effective or sufficient amount or dose" refer to a dose that produces therapeutic effects for which it is administered. The exact dose will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, Dosage Calculations (1999); and *Remington: The Science and Practice of Pharmacy,* 20th Edition, 2003, Gennaro, Ed., Lippincott, Williams & Wilkins). In sensitized cells, the therapeutically effective dose can often be lower than the conventional therapeutically effective dose for non-sensitized cells.

"Treat", "treating" and "treatment" refers to any indicia of success in the treatment or amelioration of an injury, pathology, condition, or symptom (e.g., pain), including any objective or subjective parameter such as abatement; remission; diminishing of symptoms or making the symptom, injury, pathology or condition more tolerable to the patient; decreasing the frequency or duration of the symptom or condition; or, in some situations, preventing the onset of the symptom. The treatment or amelioration of symptoms can be based on any objective or subjective parameter; including, e.g., the result of a physical examination.

"Disease" refers abnormal cellular function in an organism, which is not due to a direct result of a physical or external injury. Diseases can refer to any condition that causes distress, dysfunction, disabilities, disorders, infections, pain, or even death. Diseases include, but are not limited to hereditary diseases such as genetic and non-genetic diseases, infectious diseases, non-infectious diseases such as cancer, deficiency diseases, neurological diseases, and physiological diseases.

"Administering" refers to oral administration, administration as a suppository, topical contact, parenteral, intravenous, intraperitoneal, intramuscular, intralesional, intranasal or subcutaneous administration, intrathecal administration, or the implantation of a slow-release device e.g., a mini-osmotic pump, to the subject.

"Subject" refers to animals such as mammals, including, but not limited to, primates (e.g., humans), cows, sheep, goats, horses, dogs, cats, rabbits, rats, mice and the like. In certain embodiments, the subject is a human.

"Neural plasticity" refers to the ability of the brain to change its structure and/or function continuously throughout a subject's life. Examples of the changes to the brain include, but are not limited to, the ability to adapt or respond to internal and/or external stimuli, such as due to an injury, and the ability to produce new neurites, dendritic spines, and synapses.

"Dendritic crossing" refers to dendritic branches which overlap each other or form a cluster. Dendritic crossing can be measured by Sholl Analysis.

"Dendritic spine" refers to the small membrane protruding from a dendrite which can receive electric signal from an axon at the synapse. Dendritic spines are useful for transmitting electric signals to the neuron's cell body. Dendrites of a single neuron can comprise hundreds to thousands of spines. Dendritic spine density refers to the number of spines within the length of a dendrite. As an illustrative example, a dendritic spine density of 5 $\mu m^{-1}$ indicates 5 spines per 1 μm stretch of a dendrite.

"Modulate" or "modulating" or "modulation" refers to an increase or decrease in the amount, quality, or effect of a particular activity, function or molecule. By way of illustration and not limitation, agonists, partial agonists, antagonists, and allosteric modulators (e.g., a positive allosteric modulator) of a G protein-coupled receptor (e.g., $5HT_{2A}$ or $5HT_{2C}$) are modulators of the receptor.

"Agonism" refers to the activation of a receptor or enzyme by a modulator, or agonist, to produce a biological response.

"Agonist" refers to a modulator that binds to a receptor or enzyme and activates the receptor to produce a biological response. By way of example only, "$5HT_{2A}$ agonist" can be used to refer to a compound that exhibits an $EC_{50}$ with respect to $5HT_{2A}$ activity of no more than about 100 μM. In some embodiments, the term "agonist" includes full agonists or partial agonists. "Full agonist" refers to a modulator that binds to and activates a receptor with the maximum response that an agonist can elicit at the receptor. "Partial agonist" refers to a modulator that binds to and activates a given receptor, but has partial efficacy, that is, less than the maximal response, at the receptor relative to a full agonist.

"Positive allosteric modulator" refers to a modulator that binds to a site distinct from the orthosteric binding site and enhances or amplifies the effect of an agonist.

"Antagonism" refers to the inactivation of a receptor or enzyme by a modulator, or antagonist. Antagonism of a receptor, for example, is when a molecule binds to the receptor and does not allow activity to occur.

"Antagonist" or "neutral antagonist" refers to a modulator that binds to a receptor or enzyme and blocks a biological response. An antagonist has no activity in the absence of an agonist or inverse agonist but can block the activity of either, causing no change in the biological response.

III. Compounds

The present invention provides ergoline non-hallucinogenic compounds useful for the treatment of a variety of neurological diseases and disorders as well as increasing neuronal plasticity.

Psychedelic compounds promote structural and functional neural plasticity in key circuits, elicit therapeutic responses in multiple neuropsychiatric disorders, and produce beneficial neurological effects that can last for months following a single administration. Compounds capable of modifying neural circuits that control motivation, anxiety, and drug-seeking behavior have potential for treating neurological diseases and disorders that are mediated by the loss of synaptic connectivity and/or plasticity. Moreover, such compounds are likely to produce sustained therapeutic effects because, for example, of the potential to treat the underlying pathological changes in circuitry.

$5\text{-}HT_{2A}$ antagonists abrogate the neuritogenesis and spinogenesis effects of hallucinogenic compounds with 5-HT2A agonist activity, e.g., DMT, LSD, and DOI, demonstrating the correlation of 5-HT2A agonism and the promotion of neural plasticity (Ly et al., 2018; Dunlap et al., 2020). However, the hallucinogenic and dissociative potential of such compounds has limited the use of these compounds in the clinic for neurological diseases, such as, for example, neuropsychiatric diseases. (Ly et al., 2018).

In addition, non-hallucinogenic analogs of psychedelic compounds, such as, for example, lisuride and sumatriptan, have been examined as treatments for various neurological diseases and disorders, such as, but not limited to, neurodegenerative diseases (e.g., Alzheimer's disease and Parkinson's disease) and headaches (e.g., migraines).

Provided herein are novel non-hallucinogenic ergoline compounds that promote neuronal growth and/or improve neuronal structure.

In some embodiments, compounds provided herein possess comparable affinity for serotonin receptors (e.g., $5HT_{2A}$ and/or $5HT_{2C}$) as compared to their hallucinogenic counterparts. In some embodiments, the compounds provided herein have improved physiochemical properties as a result of the loss of a hydrogen bond donor, decreasing total polar surface area and improving central nervous system multi-parameter optimization (MPO) scores. Described herein in some embodiments are non-hallucinogenic compounds that demonstrate similar therapeutic potential as hallucinogenic 5-HT modulators (e.g., $5HT_{2A}$ and/or $5HT_{2C}$ modulators). In some embodiments, the non-hallucinogenic compounds described herein provide better therapeutic potential than hallucinogenic 5-HT modulators (e.g., $5HT_{2A}$ and/or $5HT_{2C}$ modulators) for neurological diseases.

Provided herein is a heterocyclic compound useful for the treatment of a variety of diseases such as brain disorders and other conditions. In some embodiments, the heterocyclic compounds provided herein are $5\text{-}HT_{2A}$ modulators and promote neural plasticity (e.g., cortical structural plasticity).

In some embodiments, provided herein is a compound, or a pharmaceutically acceptable salt thereof, having a structure of Formula (Ia) or Formula (Ib):

(Ia)

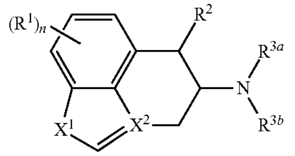

(Ib)

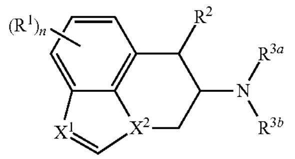

wherein: $X^1$ and $X^2$ are each independently C, CH, $CH_2$, N, or NH; each $R^1$ is independently $C_{1-6}$ alkyl, $C_{2-6}$ alkenyl, $C_{2-6}$ alkynyl, $C_{1-6}$ alkoxy, $C_{1-6}$ alkoxyalkyl, halogen, $C_{1-6}$ haloalkyl, $C_{1-6}$ haloalkoxy, —$NO_2$, or —CN; alternatively, two $R^1$ groups on adjacent ring atoms are combined to form a 4 to 8 membered heterocycloalkyl having 1 to 2 heteroatoms, each independently N, O, or S; $R^2$ is hydrogen or =O; $R^{3a}$ and $R^{3b}$ are each independently hydrogen, $C_{1-6}$ alkyl, or $C_{1-6}$ haloalkyl; alternatively, $R^{3a}$ is combined with $R^{3b}$ and the atom to which they are attached to form a 3 to 8 membered heterocycloalkyl having 1 to 2 heteroatoms, each independently N, O, or S; alternatively, $R^2$ is combined with $R^{3a}$ and the atoms to which they are attached to form a 5 to 8 membered heterocycloalkyl having 1 to 2 heteroatoms, each independently N, O, or S, wherein the heterocycloalkyl is substituted with —C(O)N($R^{2a}$)($R^{2b}$); $R^{2a}$ and $R^{2b}$ are each independently hydrogen or $C_{1-6}$ alkyl; and subscript n is 0 to 3.

In some embodiments, provided herein is a compound, or a pharmaceutically acceptable salt thereof, having a structure of Formula (Ia) or Formula (Ib):

(Ia)

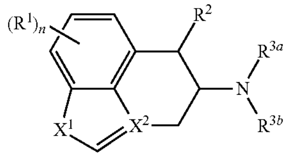

(Ib)

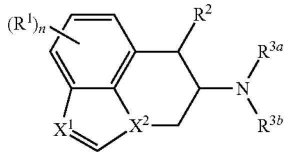

wherein: $X^1$ and $X^2$ are each independently C, CH, $CH_2$, N, or NH; each $R^1$ is independently hydrogen, $C_{1-6}$ alkyl, $C_{2-6}$ alkenyl, $C_{2-6}$ alkynyl, $C_{1-6}$ alkoxy, $C_{1-6}$ alkoxyalkyl, halogen, $C_{1-6}$ haloalkyl, $C_{1-6}$ haloalkoxy, —$NO_2$, or —CN; alternatively, two $R^1$ groups on adjacent ring atoms are combined to form a 4 to 8 membered heterocycloalkyl having 1 to 2 heteroatoms, each independently N, O, or S; $R^2$ is hydrogen or =O; $R^{3a}$ and $R^{3b}$ are each independently hydrogen, $C_{1-6}$ alkyl, or $C_{1-6}$ haloalkyl; alternatively, $R^{3a}$ is combined with $R^{3b}$ and the atom to which they are attached to form a 3 to 8 membered heterocycloalkyl having 1 to 2 heteroatoms, each independently N, O, or S; alternatively, $R^2$ is combined with $R^{3a}$ and the atoms to which they are attached to form a 5 to 8 membered heterocycloalkyl having 1 to 2 heteroatoms, each independently N, O, or S, wherein the heterocycloalkyl is substituted with —C(O)N($R^{2a}$)($R^{2b}$); $R^{2a}$ and $R^{2b}$ are each independently hydrogen or $C_{1-6}$ alkyl; and subscript n is 0 to 3, wherein the compound is other than the following structures:

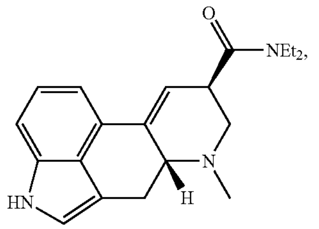

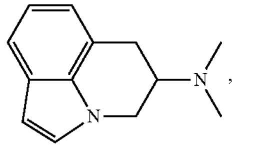

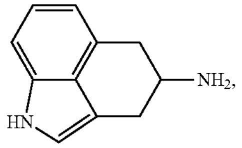

-continued

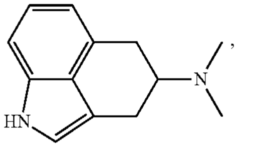

and

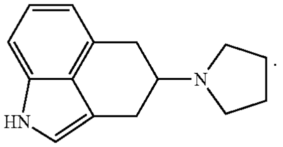

In some embodiments, when the compound has a structure of Formula (Ia), and $X^1$ is NH, $X^2$ is C, $R^2$ is hydrogen, and $R^{3a}$ and $R^{3b}$ are each independently methyl, then subscript n is 1 to 3 and at least one $R^1$ is $C_{1-6}$ alkyl, $C_{2-6}$ alkenyl, $C_{2-6}$ alkynyl, $C_{1-6}$ alkoxy, $C_{1-6}$ alkoxyalkyl, halogen, $C_{1-6}$ haloalkyl, $C_{1-6}$ haloalkoxy, —$NO_2$, or —CN; alternatively, two $R^1$ groups on adjacent ring atoms are combined to form a 4 to 8 membered heterocycloalkyl having 1 to 2 heteroatoms, each independently N, O, or S. In some embodiments, when the compound has a structure of Formula (Ia), and $X^1$ is NH, $X^2$ is C, $R^2$ is hydrogen, and $R^{3a}$ and $R^{3b}$ are each independently hydrogen, then subscript n is 1 to 3 and at least one $R^1$ is $C_{1-6}$ alkyl, $C_{2-6}$ alkenyl, $C_{2-6}$ alkynyl, $C_{1-6}$ alkoxy, $C_{1-6}$ alkoxyalkyl, halogen, $C_{1-6}$ haloalkyl, $C_{1-6}$ haloalkoxy, —$NO_2$, or —CN; alternatively, two $R^1$ groups on adjacent ring atoms are combined to form a 4 to 8 membered heterocycloalkyl having 1 to 2 heteroatoms, each independently N, O, or S. In some embodiments, when the compound has a structure of Formula (Ia), and $X^1$ is NH, $X^2$ is C, $R^2$ is hydrogen, and $R^{3a}$ and $R^{3b}$ are combined to form a pyrrolidinyl ring, then subscript n is 1 to 3 and at least one $R^1$ is $C_{1-6}$ alkyl, $C_{2-6}$ alkenyl, $C_{2-6}$ alkynyl, $C_{1-6}$ alkoxy, $C_{1-6}$ alkoxyalkyl, halogen, $C_{1-6}$ haloalkyl, $C_{1-6}$ haloalkoxy, —$NO_2$, or —CN; alternatively, two $R^1$ groups on adjacent ring atoms are combined to form a 4 to 8 membered heterocycloalkyl having 1 to 2 heteroatoms, each independently N, O, or S.

In some embodiments, when the compound has a structure of Formula (Ib) and $X^1$ is CH, $X^2$ is N, $R^2$ is hydrogen, and $R^{3a}$ and $R^{3b}$ are each independently methyl, then subscript n is 1 to 3 and at least one $R^1$ is $C_{1-6}$ alkyl, $C_{2-6}$ alkenyl, $C_{2-6}$ alkynyl, $C_{1-6}$ alkoxy, $C_{1-6}$ alkoxyalkyl, halogen, $C_{1-6}$ haloalkyl, $C_{1-6}$ haloalkoxy, —$NO_2$, or —CN; alternatively, two $R^1$ groups on adjacent ring atoms are combined to form a 4 to 8 membered heterocycloalkyl having 1 to 2 heteroatoms, each independently N, O, or S.

In some embodiments, provided herein is a compound, or a pharmaceutically acceptable salt thereof, having is structure of Formula (Ia-3):

(Ia-3)

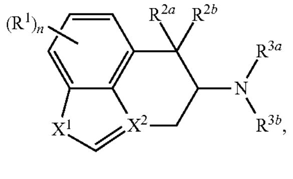

wherein: $X^1$ is NH; $X^2$ is C; each $R^1$ is independently alkyl, alkoxy, alkoxyalkyl, halogen, haloalkyl, haloalkoxy, —$NO_2$, or —CN; alternatively, two $R^1$ groups on adjacent ring atoms are combined to form a 4 to 8 membered heterocycloalkyl having 1 to 2 heteroatoms, each heteroatom independently selected from the group consisting of N, O, and S; $R^{2a}$ and $R^{2b}$ are each hydrogen or $R^{2a}$ and $R^{2b}$ are taken together with the atoms to which they are attached to form =O; $R^{3a}$ and $R^{3b}$ are each independently hydrogen, alkyl, or haloalkyl; alternatively $R^{3a}$ and $R^{3b}$ are taken together with the atoms to which they are attached to form a 3 to 8 membered heterocycloalkyl having 1 to 2 heteroatoms, each heteroatom independently selected from the group consisting of N, O, and S; alternatively, $R^{2a}$ is combined with $R^{3a}$ and the atoms to which they are attached to form a 5 to 8 membered heterocycloalkyl having 1 to 2 heteroatoms, each heteroatom independently selected from the group consisting of N, O, and S, wherein the heterocycloalkyl is substituted with —C(O)N($R^{4a}$)($R^{4b}$); $R^{4a}$ and $R^{4b}$ are each independently hydrogen or alkyl; and subscript n is 0 to 3. In some embodiments, the compound of Formula (Ia-3), or a pharmaceutically acceptable salt thereof, is the compound wherein $R^{2a}$ and $R^{2b}$ are each hydrogen. In some embodiments, the compound of Formula (Ia-3), or a pharmaceutically acceptable salt thereof, is the compound wherein $R^{2a}$ and $R^{2b}$ are taken together with the atoms to which they are attached to form =O.

In some embodiments, the compound is other than the following structures:

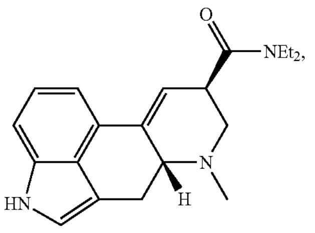

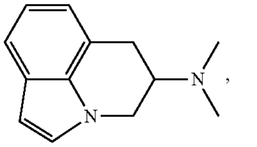

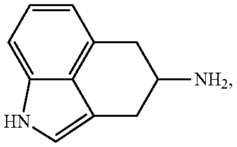

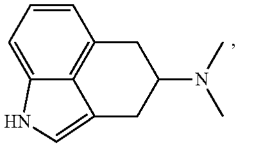

and

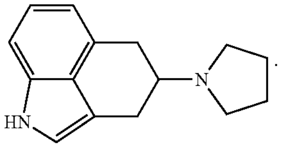

In some embodiments, the compound is other than the following structures:

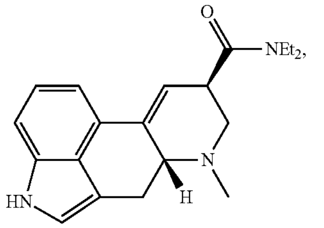

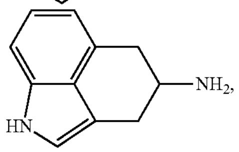

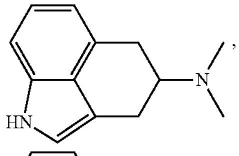

and

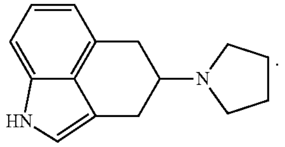

In some embodiments, provided herein is a compound, or a pharmaceutically acceptable salt thereof, having is structure of Formula (Ib-3):

(Ib-3)

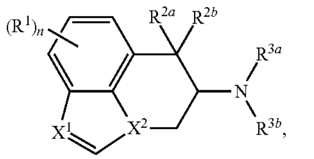

wherein: $X^1$ is CH; $X^2$ is N; each $R^1$ is independently alkyl, alkoxy, alkoxyalkyl, halogen, haloalkyl, haloalkoxy, —$NO_2$, or —CN; alternatively, two $R^1$ groups on adjacent ring atoms are combined to form a 4 to 8 membered heterocycloalkyl having 1 to 2 heteroatoms, each heteroatom independently selected from the group consisting of N, O, and S; $R^{2a}$ and $R^{2b}$ are each hydrogen or $R^{2a}$ and $R^{2b}$ are taken together with the atoms to which they are attached to form ═O; $R^{3a}$ and $R^{3b}$ are each independently hydrogen, alkyl, or haloalkyl; alternatively $R^{3a}$ and $R^{3b}$ are taken together with the atoms to which they are attached to form a 3 to 8 membered heterocycloalkyl having 1 to 2 heteroatoms, each heteroatom independently selected from the group consisting of N, O, and S; alternatively, $R^{2a}$ is combined with $R^{3a}$ and the atoms to which they are attached to form a 5 to 8 membered heterocycloalkyl having 1 to 2 heteroatoms, each heteroatom independently selected from the group consisting of N, O, and S, wherein the heterocycloalkyl is substituted with —C(O)N($R^{4a}$)($R^{4b}$); $R^{4a}$ and $R^{4b}$ are each independently hydrogen or alkyl; and subscript n is 0 to 3. In some embodiments, the compound of Formula (Ib-3), or a pharmaceutically acceptable salt thereof, is the compound wherein $R^{2a}$ and $R^{2b}$ are each hydrogen. In some embodiments, the compound of Formula (Ib-3), or a pharmaceutically acceptable salt thereof, is the compound wherein $R^{2a}$ and $R^{2b}$ are taken together with the atoms to which they are attached to form ═O.

In some embodiments, the compound is other than the following structure:

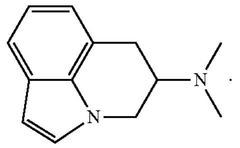

In some embodiments, provided herein is a compound of Formula (Ia), or Formula (Ib), or a pharmaceutically acceptable salt thereof, (Ia)

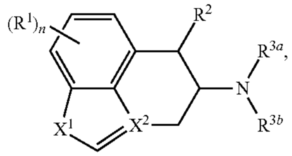

(Ib)

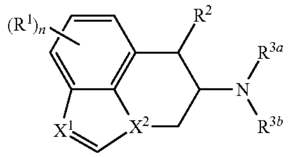

wherein: $X^1$ and $X^2$ are each independently C, CH, $CH_2$, N, or NH; each $R^1$ is independently hydrogen, $C_{1-6}$ alkyl, $C_{2-6}$ alkenyl, $C_{2-6}$ alkynyl, $C_{1-6}$ alkoxy, halogen, $C_{1-6}$ haloalkyl, $C_{1-6}$ haloalkoxy, —$NO_2$, or —CN; alternatively, two $R^1$ groups on adjacent ring atoms are combined to form a 4 to 8 membered heterocycloalkyl having 1 to 2 heteroatoms, each independently N, O, or S; $R^2$ is hydrogen or ═O; $R^{3a}$ and $R^{3b}$ are each independently hydrogen or $C_{1-6}$ alkyl; alternatively, $R^{3a}$ is combined with $R^{3b}$ and the atom to which they are attached to form a 3 to 8 membered heterocycloalkyl having 1 to 2 heteroatoms, each independently N, O, or S; alternatively, $R^2$ is combined with $R^{3a}$ and the atoms to which they are attached to form a 5 to 8 membered heterocycloalkyl having 1 to 2 heteroatoms, each independently N, O, or S, wherein the heterocycloalkyl is substituted with —C(O)N($R^{2a}$)($R^{2b}$); $R^{2a}$ and $R^{2b}$ are each independently hydrogen or $C_{1-6}$ alkyl; and subscript n is 0 to 3, wherein the compound is other than the following structure:

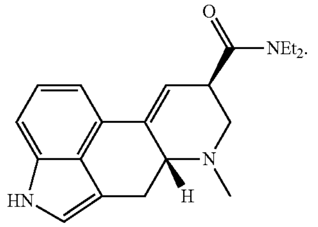

$X^1$ and $X^2$ can be any suitable atom. In some embodiments, $X^1$ and $X^2$ are each independently C, CH, $CH_2$, N, or NH. In some embodiments, the compound of Formula (Ia) or (Ib), or a pharmaceutically acceptable salt thereof, is the compound wherein one of $X^1$ and $X^2$ is N or NH. In some embodiments, the compound of Formula (Ia) or (Ib), or a pharmaceutically acceptable salt thereof, is the compound wherein one of $X^1$ and $X^2$ is C, CH, or $CH_2$. In some embodiments, the compound of Formula (Ia), or a pharmaceutically acceptable salt thereof, is the compound wherein $X^1$ is NH and $X^2$ is C. In some embodiments, the compound of Formula (Ib), or a pharmaceutically acceptable salt thereof, is the compound wherein $X^1$ is CH and $X^2$ is N.

In some embodiments, the compound of Formula (Ia) or (Ib), or a pharmaceutically acceptable salt thereof, is the compound having a structure of Formula (Ia-1), Formula (Ia-2), Formula (Ib-1), or Formula (Ib-2):

(Ia-1)

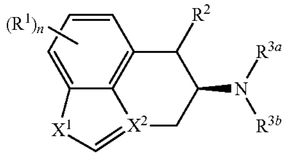

(Ia-2)

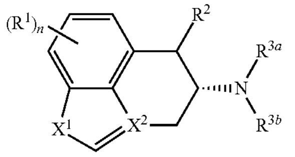

(Ib-1)

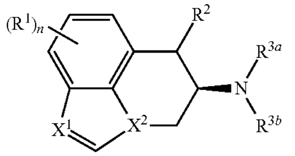

(Ib-2)

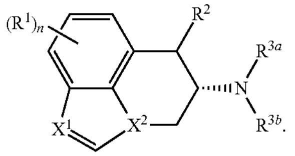

In some embodiments, provided herein is a compound having a structure of Formula (Ia-1) or Formula (Ia-2):

(Ia-1)

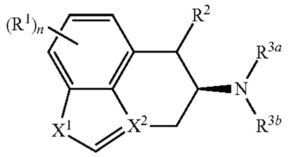

(Ia-2)

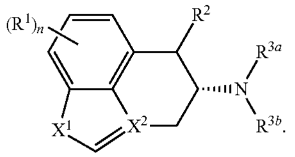

In some embodiments, provided herein is a compound having a structure of Formula (Ia-1):

(Ia-1)

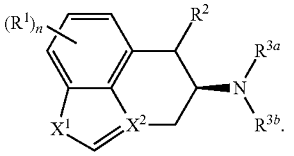

In some embodiments, provided herein is a compound having a structure of Formula (Ia-2):

(Ia-2)

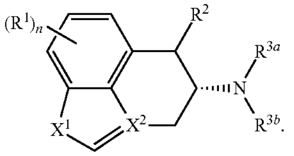

In some embodiments, provided herein is a compound having a structure of Formula (Ib-1) or Formula (Ib-2):

(Ib-1)

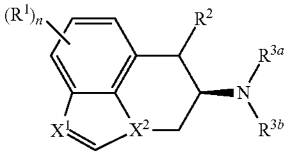

(Ib-2)

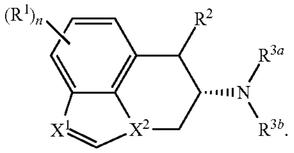

In some embodiments, provided herein is a compound having a structure of Formula (Ib-1):

(Ib-1)

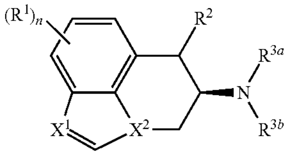

In some embodiments, provided herein is a compound having a structure of Formula (Ib-2):

(Ib-2)

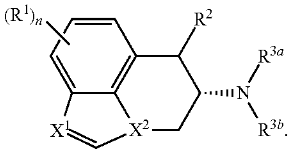

In some embodiments, the compound of Formula (Ib), (Ib-1), or (Ib-2), or a pharmaceutically acceptable salt thereof, is the compound wherein $X^1$ is CH and $X^2$ is N. In some embodiments, the compound of Formula (Ib), or a pharmaceutically acceptable salt thereof, is the compound having a structure of Formula (Ic):

(Ic)

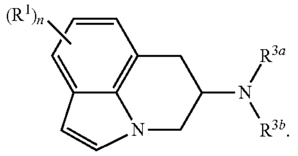

In some embodiments, the compound of Formula (Ib), (Ib-1), (Ib-2), or (Ic), or a pharmaceutically acceptable salt thereof, is the compound having a structure of Formula (Ic-1) or Formula (Ic-2):

(Ic-1)

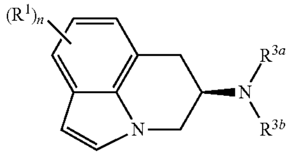

(Ic-2)

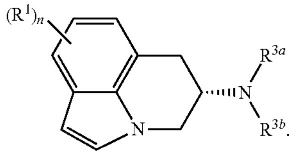

In some embodiments, the compound of Formula (Ia), (Ia-1), or (Ia-2), or a pharmaceutically acceptable salt thereof, is the compound wherein $X^1$ is NH and $X^2$ is C. In some embodiments, the compound of Formula (Ia), or a pharmaceutically acceptable salt thereof, is the compound having a structure of Formula (Id):

(Id)

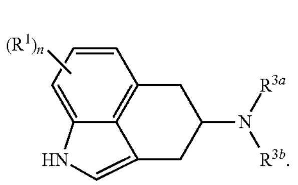

In some embodiments, the compound of Formula (Ia), (Ia-1), (Ia-2), or (Id), or a pharmaceutically acceptable salt thereof, is the compound having a structure of Formula (Id-1) or Formula (Id-2):

(Id-1)

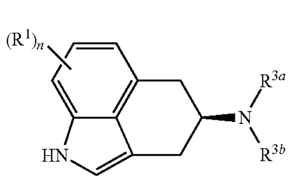

-continued (Id-2)

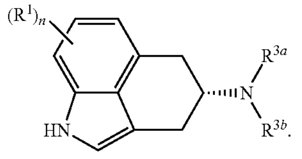

Each $R^1$ can be any suitable functional group. In some embodiments, the compound of Formula (Ia), (Ia-1), (Ia-2), (Ib), (Ib-1), (Ib-2), (Ic), (Ic-1), (Ic-2), (Id), (Id-1), or (Id-2), or a pharmaceutically acceptable salt thereof, is the compound wherein each $R^1$ is independently hydrogen, alkyl, alkenyl, alkynyl, alkoxy, alkoxyalkyl, halogen, haloalkyl, haloalkoxy, —$NO_2$, or —CN. In some embodiments, two adjacent $R^1$ groups are taken together with the atoms to which they are attached to form an 5- to 6-membered heterocycloalkyl having 1 to 2 heteroatoms, each heteroatom independently selected from the group consisting of N, O, and S. In some embodiments, one or more $R^1$ is alkyl, alkenyl, alkynyl, alkoxy, alkoxyalkyl, halogen, haloalkyl, haloalkoxy, —$NO_2$, —CN or two adjacent $R^1$ are taken together with the atoms to which they are attached to form an 5- to 6-membered heterocycloalkyl having 1 to 2 heteroatoms, each heteroatom independently selected from the group consisting of N, O, and S. In some embodiments, one or more $R^1$ is alkyl, alkenyl, alkynyl, alkoxy, alkoxyalkyl, halogen, haloalkyl, haloalkoxy, —$NO_2$, or —CN. In some embodiments, two adjacent $R^1$ are taken together with the atoms to which they are attached to form a 5- to 6-membered heterocycloalkyl, having 1 to 2 heteroatoms, each heteroatom independently selected from the group consisting of N, O, and S.

In some embodiments, the compound of Formula (Ia), (Ia-1), (Ia-2), (Ib), (Ib-1), (Ib-2), (Ic), (Ic-1), (Ic-2), (Id), (Id-1), or (Id-2), or a pharmaceutically acceptable salt thereof, is the compound wherein each $R^1$ is independently hydrogen, $C_{1-6}$ alkyl, $C_{2-6}$ alkenyl, $C_{2-6}$ alkynyl, $C_{1-6}$ alkoxy, $C_{1-6}$ alkoxyalkyl, halogen, $C_{1-6}$ haloalkyl, $C_{1-6}$ haloalkoxy, —$NO_2$, or —CN, wherein at least one $R^1$ is $C_{1-6}$ alkyl, $C_{2-6}$ alkenyl, $C_{2-6}$ alkynyl, $C_{1-6}$ alkoxy, $C_{1-6}$ alkoxyalkyl, halogen, $C_{1-6}$ haloalkyl, $C_{1-6}$ haloalkoxy, —$NO_2$, or —CN; alternatively, two $R^1$ groups on adjacent ring atoms are combined to form a 4 to 8 membered heterocycloalkyl having 1 to 2 heteroatoms, each independently N, O, or S. In some embodiments, the compound of Formula (Ia), (Ia-1), (Ia-2), (Ib), (Ib-1), (Ib-2), (Ic), (Ic-1), (Ic-2), (Id), (Id-1), or (Id-2), or a pharmaceutically acceptable salt thereof, is the compound wherein each $R^1$ is independently hydrogen, $C_{1-6}$ alkyl, $C_{2-6}$ alkenyl, $C_{2-6}$ alkynyl, $C_{1-6}$ alkoxy, halogen, $C_{1-6}$ haloalkyl, $C_{1-6}$ haloalkoxy, —$NO_2$, or —CN; alternatively, two $R^1$ groups on adjacent ring atoms are combined to form a 4 to 8 membered heterocycloalkyl having 1 to 2 heteroatoms, each independently N, O, or S.

In some embodiments, the compound of Formula (Ia), (Ia-1), (Ia-2), (Ib), (Ib-1), (Ib-2), (Ic), (Ic-1), (Ic-2), (Id), (Id-1), or (Id-2), or a pharmaceutically acceptable salt thereof, is the compound wherein each $R^1$ is independently hydrogen, $C_{1-6}$ alkyl, $C_{2-6}$ alkenyl, $C_{2-6}$ alkynyl, $C_{1-6}$ alkoxy, $C_{1-6}$ alkoxyalkyl, halogen, $C_{1-6}$ haloalkyl, $C_{1-6}$ haloalkoxy, —$NO_2$, or —CN, wherein at least one $R^1$ is $C_{1-6}$ alkyl, $C_{2-6}$ alkenyl, $C_{2-6}$ alkynyl, $C_{1-6}$ alkoxy, $C_{1-6}$ alkoxyalkyl, halogen, $C_{1-6}$ haloalkyl, $C_{1-6}$ haloalkoxy, —$NO_2$, or —CN; alternatively, two $R^1$ groups on adjacent ring atoms are combined to form a 4 to 8 membered heterocycloalkyl having 1 to 2 heteroatoms, each independently N, O, or S. In some embodiments, the compound of Formula (Ia), (Ia-1), (Ia-2), (Ib), (Ib-1), (Ib-2), (Ic), (Ic-1), (Ic-2), (Id), (Id-1), or (Id-2), or a pharmaceutically acceptable salt thereof, is the compound wherein each $R^1$ is independently hydrogen, $C_{1-6}$ alkyl, $C_{2-6}$ alkenyl, $C_{2-6}$ alkynyl, $C_{1-6}$ alkoxy, halogen, $C_{1-6}$ haloalkyl, $C_{1-6}$ haloalkoxy, —$NO_2$, or —CN; alternatively, two $R^1$ groups on adjacent ring atoms are combined to form a 4 to 8 membered heterocycloalkyl having 1 to 2 heteroatoms, each independently N, O, or S.

In some embodiments, the compound of Formula (Ia), (Ia-1), (Ia-2), (Ib), (Ib-1), (Ib-2), (Ic), (Ic-1), (Ic-2), (Id), (Id-1), or (Id-2), or a pharmaceutically acceptable salt thereof, is the compound wherein each $R^1$ is independently hydrogen, $C_{1-6}$ alkyl, $C_{2-6}$ alkenyl, $C_{2-6}$ alkynyl, $C_{1-6}$ alkoxy, $C_{1-6}$ alkoxyalkyl, halogen, $C_{1-6}$ haloalkyl, $C_{1-6}$ haloalkoxy, —$NO_2$, or —CN, wherein at least one $R^1$ is $C_{1-6}$ alkyl, $C_{2-6}$ alkenyl, $C_{2-6}$ alkynyl, $C_{1-6}$ alkoxy, $C_{1-6}$ alkoxyalkyl, halogen, $C_{1-6}$ haloalkyl, $C_{1-6}$ haloalkoxy, —$NO_2$, or —CN.

In some embodiments, the compound of Formula (Ia), (Ia-1), (Ia-2), (Ib), (Ib-1), (Ib-2), (Ic), (Ic-1), (Ic-2), (Id), (Id-1), or (Id-2), or a pharmaceutically acceptable salt thereof, is the compound wherein each $R^1$ is independently hydrogen, $C_{1-6}$ alkyl, $C_{1-6}$ alkoxy, halogen, or $C_{1-6}$ haloalkyl. In some embodiments, the compound of Formula (Ia), (Ia-1), (Ia-2), (Ib), (Ib-1), (Ib-2), (Ic), (Ic-1), (Ic-2), (Id), (Id-1), or (Id-2), or a pharmaceutically acceptable salt thereof, is the compound wherein each $R^1$ is independently hydrogen, methyl, ethyl, n-propyl, isopropyl, n-butyl, sec-butyl, iso-butyl, tert-butyl, —OMe, —OEt, —$OCH_2CH_2CH_3$, —$OCH_2CH_2CH_2CH_3$, —F, —Cl, —$CF_3$, —$CCl_3$, —$CBr_3$ or —$CI_3$. In some embodiments, the compound of Formula (Ia), (Ia-1), (Ia-2), (Ib), (Ib-1), (Ib-2), (Ic), (Ic-1), (Ic-2), (Id), (Id-1), or (Id-2), or a pharmaceutically acceptable salt thereof, is the compound wherein each $R^1$ is independently hydrogen, methyl, ethyl, n-propyl, isopropyl, n-butyl, sec-butyl, iso-butyl, tert-butyl, —OMe, —OEt, —$OCH_2CH_2CH_3$, —$OCH_2CH_2CH_2CH_3$, —F, —Cl, or —$CF_3$. In some embodiments, the compound of Formula (Ia), (Ia-1), (Ia-2), (Ib), (Ib-1), (Ib-2), (Ic), (Ic-1), (Ic-2), (Id), (Id-1), or (Id-2), or a pharmaceutically acceptable salt thereof, is the compound wherein each $R^1$ is independently hydrogen, methyl, —OMe, —F, —Cl, or —$CF_3$.

In some embodiments, the compound of Formula (Ia), (Ia-1), (Ia-2), (Ib), (Ib-1), (Ib-2), (Ic), (Ic-1), (Ic-2), (Id), (Id-1), or (Id-2), or a pharmaceutically acceptable salt thereof, is the compound wherein two $R^1$ groups on adjacent ring atoms are combined to form a 4 to 8 membered heterocycloalkyl having 1 to 2 heteroatoms, each independently N, O, or S. In some embodiments, two $R^1$ groups on adjacent ring atoms are combined to form a 5 to 6 membered heterocycloalkyl having 1 to 2 heteroatoms, each independently N, O, or S. In some embodiments, the compound of Formula (Ia), or a pharmaceutically acceptable salt thereof, is the compound having a structure of Formula (Ie):

(Ie)

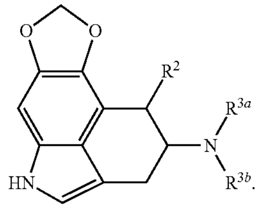

$R^2$ can be any suitable functional group. In some embodiments, $R^2$ is hydrogen or =O. In some embodiments, $R^2$ is hydrogen (e.g., $R^2$ and the atom to which $R^2$ is attached forms: —$CH_2$—). In some embodiments, $R^2$ is =O (e.g., $R^2$ and the atom to which $R^2$ is attached forms: —C=O). Unless stated specifically otherwise, the carbon atom to which $R^2$ is attached has a full octet (e.g., the carbon atom achieves a full outer energy level by forming four covalent bonds (e.g., four single bonds or two single bonds and a double bond)).

In some embodiments, the compound of Formula (Ia), or (Ie), or a pharmaceutically acceptable salt thereof, is the compound wherein $R^2$ is hydrogen or =O. In some embodiments, the compound of Formula (Ia), or (Ie), or a pharmaceutically acceptable salt thereof, is the compound wherein $R^2$ is hydrogen. In some embodiments, the compound of Formula (Ia), or (Ie), or a pharmaceutically acceptable salt thereof, is the compound wherein $R^2$ is =O.

In some embodiments, $R^2$ is combined with $R^{3a}$ and the atoms to which they are attached to form a heterocycloalkyl. In some embodiments, $R^2$ is combined with $R^{3a}$ and the atoms to which they are attached to form a 5 to 8 membered heterocycloalkyl having 1 to 2 heteroatoms, each heteroatom independently selected from the group consisting of N, O, and S. In some embodiments, the 5 to 8 membered heterocycloalkyl is substituted with —$C(O)N(R^{4a})(R^{4b})$, wherein $R^{4a}$ and $R^{4b}$ are each independently hydrogen or alkyl. In some embodiments, $R^2$ is combined with $R^{3a}$ and the atoms to which they are attached to form a 5 to 8 membered heterocycloalkenyl (e.g., containing one or more double bond within the ring). In some embodiments, the compound of Formula (Ia), or (Ie), or a pharmaceutically acceptable salt thereof, is the compound wherein $R^2$ is combined with $R^{3a}$ and the atoms to which they are attached to form a 1,2,3,6-tetrahydropyridinyl substituted with —$C(O)N(R^{4a})(R^{4b})$, wherein $R^{4a}$ and $R^{4b}$ are each independently hydrogen or alkyl.

In some embodiments, the compound of Formula (Ia), or (Ie), or a pharmaceutically acceptable salt thereof, is the compound wherein $R^2$ is combined with $R^{3a}$ and the atoms to which they are attached to form a 5 to 8 membered heterocycloalkyl having 1 to 2 heteroatoms, each independently N, O, or S, wherein the heterocycloalkyl is substituted with —$C(O)N(R^{2a})(R^{2b})$.

$R^{3a}$ and $R^{3b}$ of the present invention can be any suitable functional group. In some embodiments, $R^{3a}$ and $R^{3b}$ are each independently hydrogen, alkyl, or haloalkyl. In some embodiments, $R^{3a}$ and $R^{3b}$ are taken together with the atoms to which they are attached to form a 3 to 8 membered heterocycloalkyl having 1 to 2 heteroatoms, each heteroatom independently selected from the group consisting of N, O, and S. In some embodiments, the compound of Formula (Ia), (Ia-1), (Ia-2), (Ib), (Ib-1), (Ib-2), (Ic), (Ic-1), (Ic-2), (Id), (Id-1), (Id-2), or (Ie), or a pharmaceutically acceptable salt thereof, is the compound wherein $R^{3a}$ and $R^{3b}$ are each independently hydrogen, $C_{1-6}$ alkyl, or $C_{1-6}$ haloalkyl; alternatively, $R^{3a}$ is combined with $R^{3b}$ and the atom to which they are attached to form a 3 to 8 membered heterocycloalkyl having 1 to 2 heteroatoms, each independently N, O, or S.

In some embodiments, $R^{3a}$ and $R^{3b}$ are each independently hydrogen or $C_{1-6}$ alkyl. In some embodiments, $R^{3a}$ and $R^{3b}$ are each independently hydrogen or $C_{1-6}$ haloalkyl. In some embodiments, the compound of Formula (Ia), (Ia-1), (Ia-2), (Ib), (Ib-1), (Ib-2), (Ic), (Ic-1), (Ic-2), (Id), (Id-1), (Id-2), or (Ie), or a pharmaceutically acceptable salt thereof, is the compound wherein $R^{3a}$ and $R^{3b}$ are each independently hydrogen, methyl, ethyl, n-propyl, isopropyl, n-butyl, sec-butyl, iso-butyl, tert-butyl, or —$CF_3$. In some embodiments, the compound of Formula (Ia), (Ia-1), (Ia-2), (Ib), (Ib-1), (Ib-2), (Ic), (Ic-1), (Ic-2), (Id), (Id-1), (Id-2), or (Ie), or a pharmaceutically acceptable salt thereof, is the compound wherein $R^{3a}$ and $R^{3b}$ are each independently methyl, ethyl, n-propyl, isopropyl, n-butyl, sec-butyl, iso-butyl, or tert-butyl. In some embodiments, the compound of Formula (Ia), (Ia-1), (Ia-2), (Ib), (Ib-1), (Ib-2), (Ic), (Ic-1), (Ic-2), (Id), (Id-1), (Id-2), or (Ie), or a pharmaceutically acceptable salt thereof, is the compound wherein $R^{3a}$ and $R^{3b}$ are each independently hydrogen, methyl, ethyl, isopropyl, or —$CF_3$. In some embodiments, the compound of Formula (Ia), (Ia-1), (Ia-2), (Ib), (Ib-1), (Ib-2), (Ic), (Ic-1), (Ic-2), (Id), (Id-1), (Id-2), or (Ie), or a pharmaceutically acceptable salt thereof, is the compound wherein $R^{3a}$ and $R^{3b}$ are each independently methyl.

In some embodiments, the compound of Formula (Ia), (Ia-1), (Ia-2), (Ib), (Ib-1), (Ib-2), (Ic), (Ic-1), (Ic-2), (Id), (Id-1), (Id-2), or (Ie), or a pharmaceutically acceptable salt thereof, is the compound wherein $R^{3a}$ and $R^{3b}$ are each trifluoromethyl. In some embodiments, the compound of Formula (Ia), (Ia-1), (Ia-2), (Ib), (Ib-1), (Ib-2), (Ic), (Ic-1), (Ic-2), (Id), (Id-1), (Id-2), or (Ie), or a pharmaceutically acceptable salt thereof, is the compound wherein $R^{3a}$ and $R^{3b}$ are each independently hydrogen and methyl. In some embodiments, the compound compound of Formula (Ia), (Ia-1), (Ia-2), (Ib), (Ib-1), (Ib-2), (Ic), (Ic-1), (Ic-2), (Id), (Id-1), (Id-2), or (Ie), or a pharmaceutically acceptable salt thereof, is the compound wherein $R^{3a}$ and $R^{3b}$ are each independently hydrogen and trifluoromethyl.

In some embodiments, $R^{3a}$ is combined with $R^{3b}$ and the atoms to which they are attached to form a 3 to 8 membered heterocycloalkyl having 1 to 2 heteroatoms, each heteroatom independently selected from the group consisting of N, O, and S. In some embodiments, the compound of Formula (Ia), (Ia-1), (Ia-2), (Ib), (Ib-1), (Ib-2), (Ic), (Ic-1), (Ic-2), (Id), (Id-1), (Id-2), or (Ie), or a pharmaceutically acceptable salt thereof, is the compound wherein $R^{3a}$ is combined with $R^{3b}$ and the atom to which they are attached to form a 3 to 8 membered heterocycloalkyl having 1 to 2 heteroatoms, each independently N, O, or S. In some embodiments, the compound of Formula (Ia), (Ia-1), (Ia-2), (Ib), (Ib-1), (Ib-2), (Ic), (Ic-1), (Ic-2), (Id), (Id-1), (Id-2), or (Ie), or a pharmaceutically acceptable salt thereof, is the compound wherein $R^{3a}$ is combined with $R^{3b}$ and the atom to which they are attached to form a 4 to 6 membered heterocycloalkyl having 1 to 2 heteroatoms, each independently N, O, or S. In some embodiments, the compound of Formula (Ia), (Ia-1), (Ia-2), (Ib), (Ib-1), (Ib-2), (Ic), (Ic-1), (Ic-2), (Id), (Id-1), (Id-2), or (Ie), or a pharmaceutically acceptable salt thereof, is the compound wherein $R^{3a}$ is combined with $R^{3b}$ and the atom to which they are attached combine to form an aziridine, azetidine, pyrrolidine, or a piperidine. In some embodiments, the compound of Formula (Ia), (Ia-1), (Ia-2), (Ib), (Ib-1), (Ib-2), (Ic), (Ic-1), (Ic-2), (Id), (Id-1), (Id-2), or (Ie), or a pharmaceutically acceptable salt thereof, is the compound wherein $R^{3a}$ is combined with $R^{3b}$ and the atom to which they are attached combine to form a pyrrolidine.

In some embodiments, the compound of Formula (Ia), (Ia-1), (Ia-2), (Ib), (Ib-1), or (Ib-2), or a pharmaceutically acceptable salt thereof, is the compound wherein one of $X^1$ and $X^2$ is N or NH; one of $X^1$ and $X^2$ is C, CH, or $CH_2$; each $R^1$ is independently hydrogen, methyl, ethyl, n-propyl, isopropyl, n-butyl, sec-butyl, iso-butyl, tert-butyl, —OMe, —OEt, —$OCH_2CH_2CH_3$, —$OCH_2CH_2CH_2CH_3$, —F, —Cl, —$CF_3$, —$CCl_3$, —$CBr_3$ or —$CI_3$; alternatively, two $R^1$ groups on adjacent ring atoms are combined to form a 5 to 6 membered heterocycloalkyl having 2 heteroatoms, each independently O; $R^2$ is hydrogen; $R^{3a}$ and $R^{3b}$ are each independently hydrogen, methyl, ethyl, n-propyl, isopropyl, n-butyl, sec-butyl, iso-butyl, tert-butyl, or —$CF_3$; alternatively, $R^{3a}$ is combined with $R^{3b}$ and the atom to which they are attached to form pyrrolidine or piperidine; and n is 0 to 2.

In some embodiments, the compound of Formula (Ia), (Ia-1), (Ia-2), (Ib), (Ib-1), or (Ib-2), or a pharmaceutically acceptable salt thereof, is the compound wherein one of $X^1$ and $X^2$ is N or NH; one of $X^1$ and $X^2$ is C, CH, or $CH_2$; each $R^1$ is independently hydrogen, methyl, —OMe, —F, —Cl, or —$CF_3$; alternatively, two $R^1$ groups on adjacent ring atoms are combined to form a 5 membered heterocycloalkyl having 2 heteroatoms, each independently O; $R^2$ is hydrogen; $R^{3a}$ and $R^{3b}$ are each independently hydrogen, methyl, ethyl, isopropyl, or —$CF_3$; alternatively, $R^{3a}$ is combined with $R^{3b}$ and the atom to which they are attached to form a pyrrolidine; and n is 1 or 2.

In some embodiments, the compound of Formula (Ia), (Ia-1), (Ia-2), or a pharmaceutically acceptable salt thereof, is the compound wherein $X^1$ is NH and $X^2$ is C; each $R^1$ is independently hydrogen, methyl, —OMe, —F, —Cl, or —$CF_3$; alternatively, two $R^1$ groups on adjacent ring atoms are combined to form a 5 membered heterocycloalkyl having 2 heteroatoms, each independently O; $R^2$ is hydrogen; $R^{3a}$ and $R^{3b}$ are each independently hydrogen, methyl, ethyl, isopropyl, or —$CF_3$; alternatively, $R^{3a}$ is combined with $R^{3b}$ and the atom to which they are attached to form a pyrrolidine; and n is 1 or 2. In some embodiments, each $R^1$ is independently hydrogen, methyl, —OMe, —F, —Cl, or —$CF_3$ or two $R^1$ groups on adjacent ring atoms are combined to form a 5 membered heterocycloalkyl having 2 heteroatoms, each independently O. In some embodiments, each $R^1$ is independently hydrogen, methyl, —OMe, —F, —Cl, or —$CF_3$ and n is 1. In some embodiments, each $R^1$ is independently hydrogen, methyl, —OMe, —F, —Cl, or —$CF_3$ and n is 2. In some embodiments, $R^{3a}$ and $R^{3b}$ are each independently hydrogen, methyl, ethyl, isopropyl, or —$CF_3$ or $R^{3a}$ is combined with $R^{3b}$ and the atom to which they are attached to form a pyrrolidine.

In some embodiments, the compound of Formula (Ib), (Ib-1), or (Ib-2), or a pharmaceutically acceptable salt thereof, is the compound wherein $X^1$ is CH and $X^2$ is N; each $R^1$ is independently hydrogen, methyl, —OMe, —F, —Cl, or —$CF_3$; alternatively, two $R^1$ groups on adjacent ring atoms are combined to form a 5 membered heterocycloalkyl having 2 heteroatoms, each independently O; $R^2$ is hydrogen; $R^{3a}$ and $R^{3b}$ are each independently hydrogen, methyl, ethyl, isopropyl, or —$CF_3$; alternatively, $R^{3a}$ is combined with $R^{3b}$ and the atom to which they are attached to form a pyrrolidine; and n is 1 or 2. In some embodiments, each $R^1$ is independently hydrogen, methyl, —OMe, —F, —Cl, or —$CF_3$ or two $R^1$ groups on adjacent ring atoms are combined to form a 5 membered heterocycloalkyl having 2 heteroatoms, each independently O. In some embodiments, each $R^1$ is independently hydrogen, methyl, —OMe, —F, —Cl, or —$CF_3$ and n is 1. In some embodiments, each $R^1$ is independently hydrogen, methyl, —OMe, —F, —Cl, or —$CF_3$ and n is 2. In some embodiments, $R^{3a}$ and $R^{3b}$ are each independently hydrogen, methyl, ethyl, isopropyl, or —$CF_3$ or $R^{3a}$ is combined with $R^{3b}$ and the atom to which they are attached to form a pyrrolidine.

In some embodiments, provided herein is a compound having a structure that is:

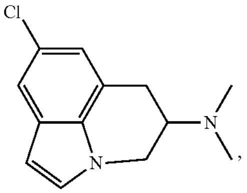,
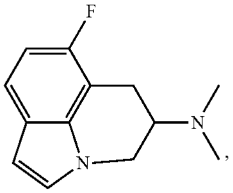,
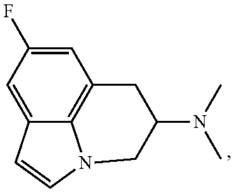,
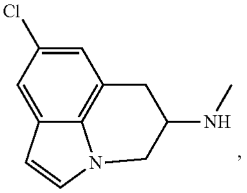,
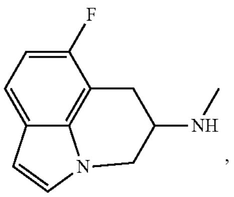,
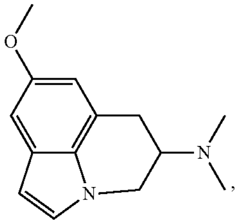,
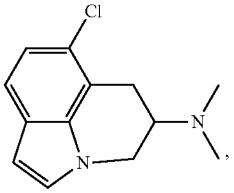,
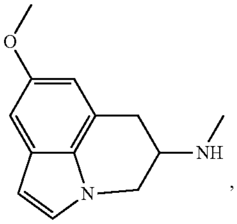,
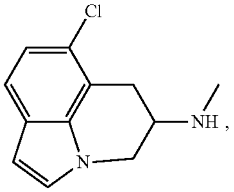,
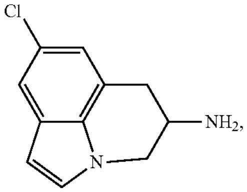,
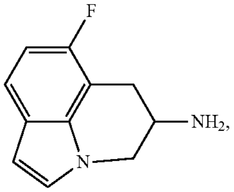,
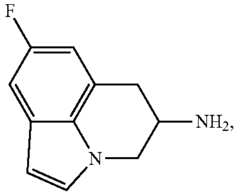,
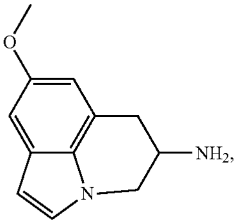,
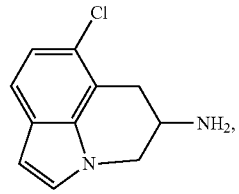,
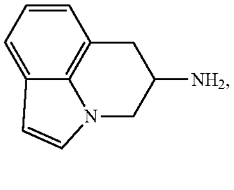,
-continued
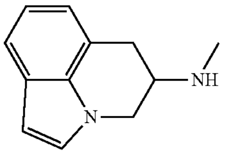,
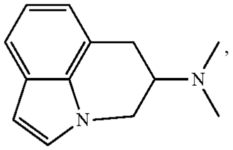,
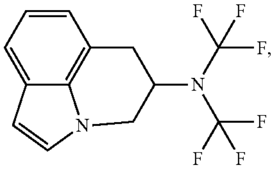,
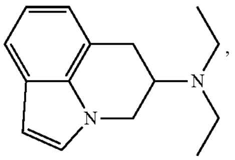,
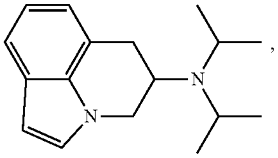,
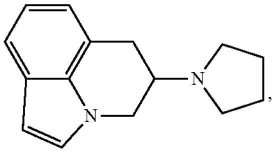, or
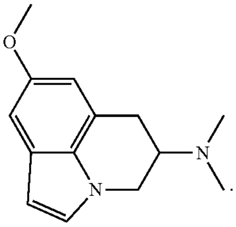.
In some embodiments, the compound of Formula (Ib), or (Ic), or a pharmaceutically acceptable salt thereof, is the compound having a structure that is:
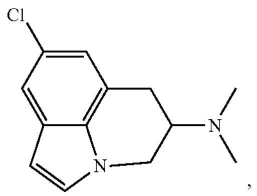,
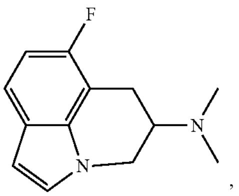,
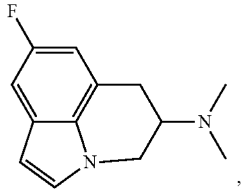,
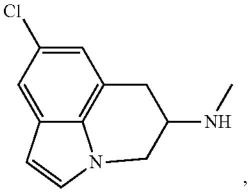,
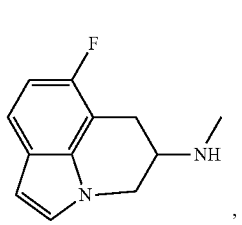,
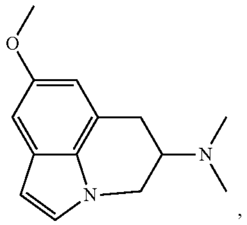, -continued
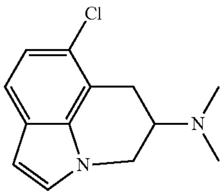
,
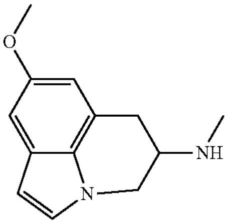
,
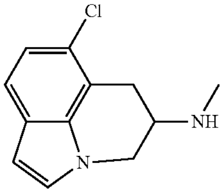
,
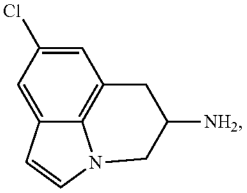
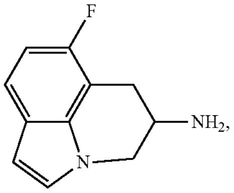
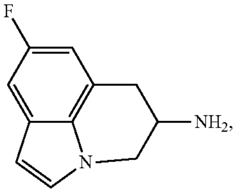
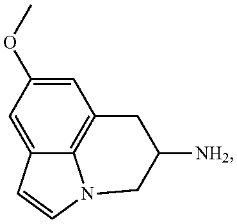
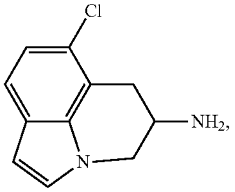
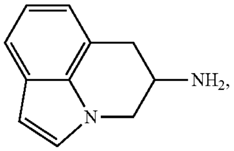
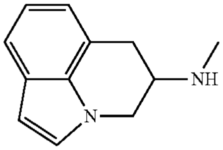
,
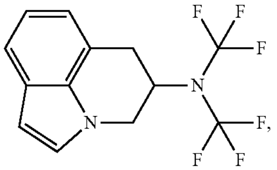
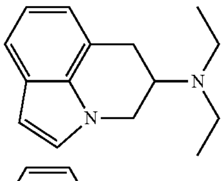
,
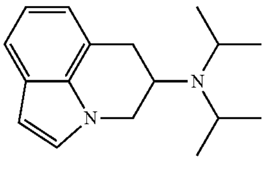
,
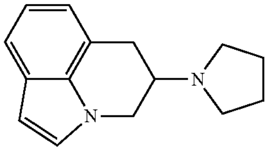
, or
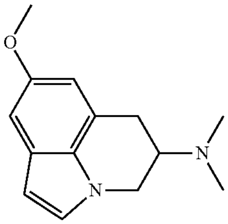
.
In some embodiments, the compound of Formula (Ib), or (Ic), or a pharmaceutically acceptable salt thereof, is the compound having a structure that is:
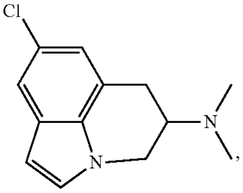
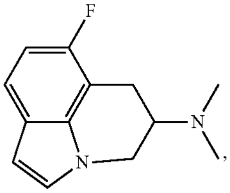
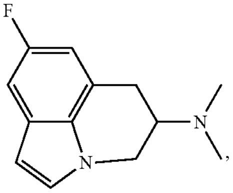
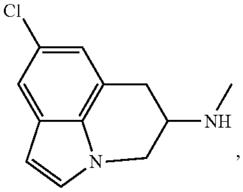
,
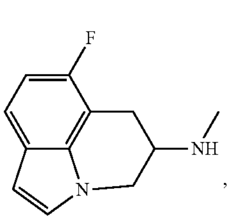
,
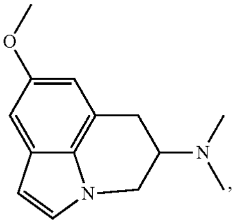
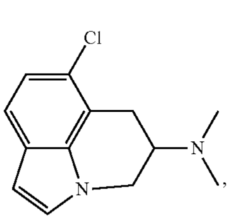
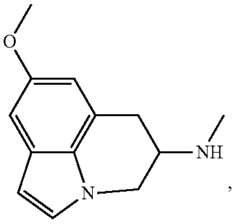
,
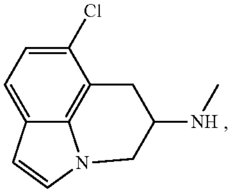
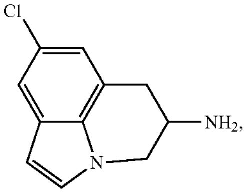
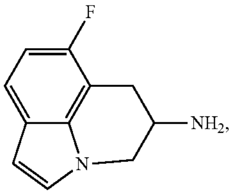
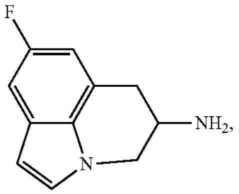
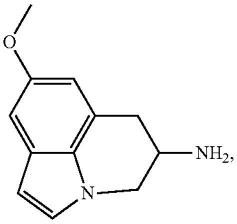
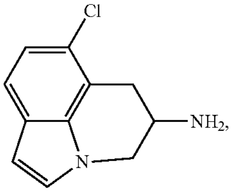
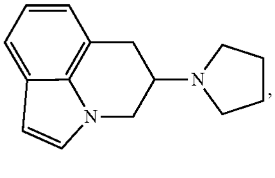
, or -continued
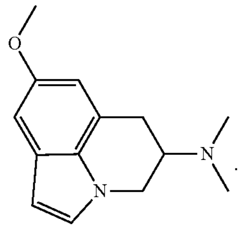
In some embodiments, the compound of Formula (Ib), or (Ic), or a pharmaceutically acceptable salt thereof, is the compound wherein a structure that is:
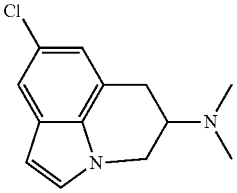
,
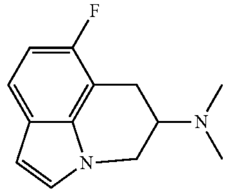
,
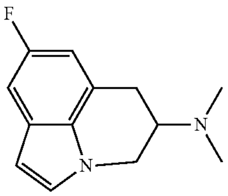
,
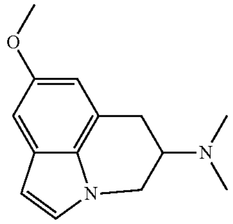
,
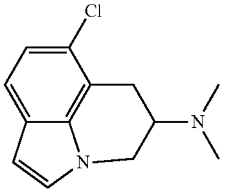
,
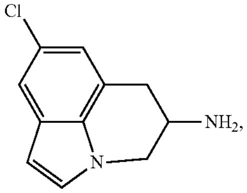
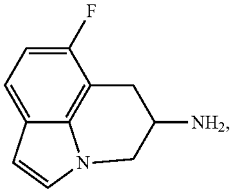
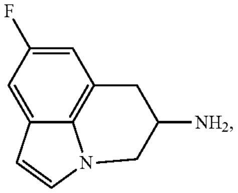
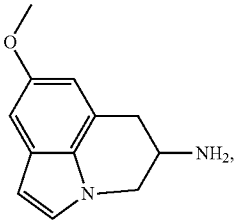
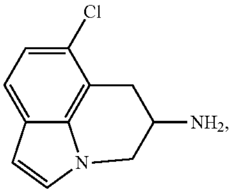
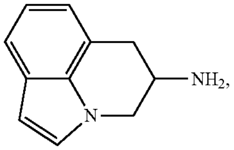
or
-continued
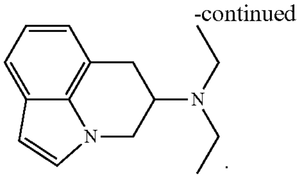
In some embodiments, the compound of Formula (Ib), or (Ic), or a pharmaceutically acceptable salt thereof, is the compound wherein a structure that is:
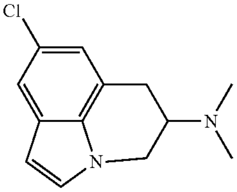
,
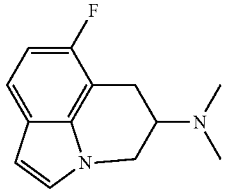
,
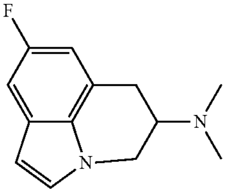
,
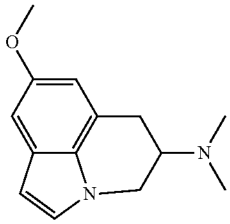
,
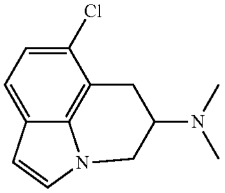
,
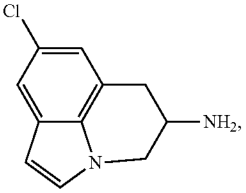
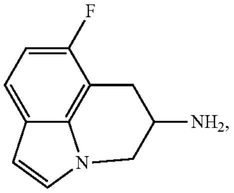
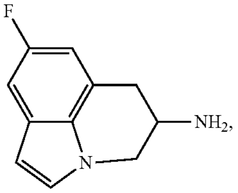
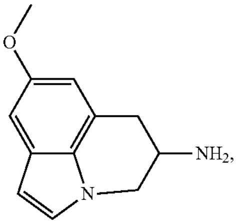
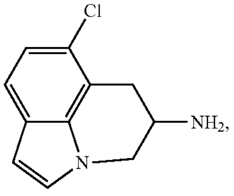
or
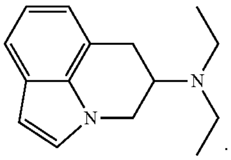

In some embodiments, the compound of Formula (Ib), (Ib-1), (Ib-2), (Ic), (Ic-1), or (Ic-2), or a pharmaceutically acceptable salt thereof, is the compound wherein a structure that is:
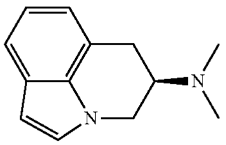
or
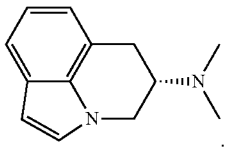
.
In some embodiments, provided herein is a compound having a structure that is:
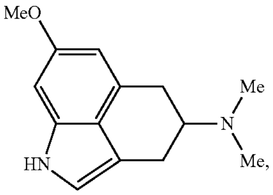
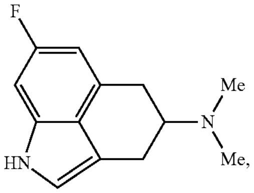
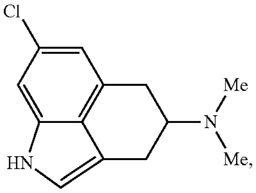
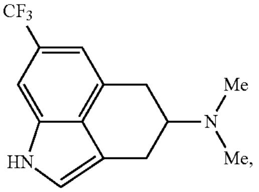
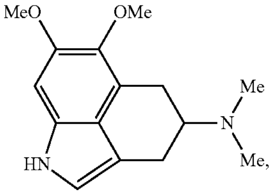
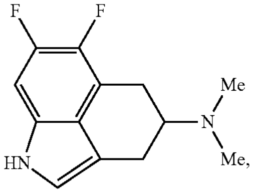
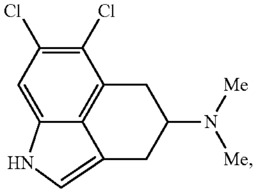
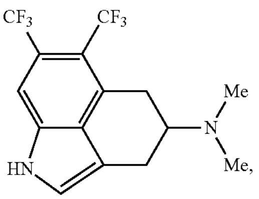
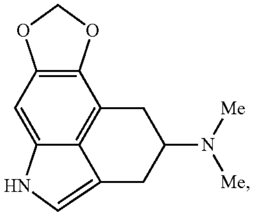
-continued
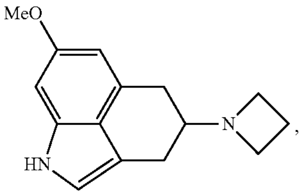
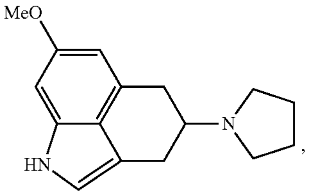
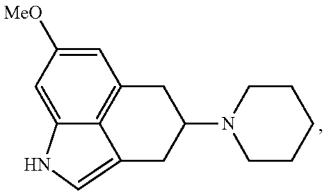
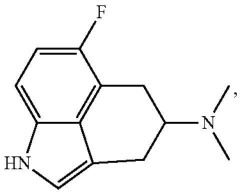
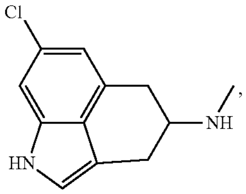
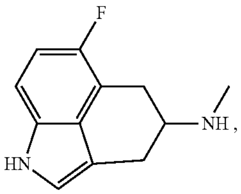
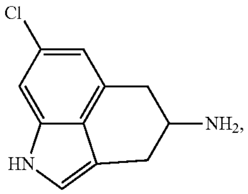
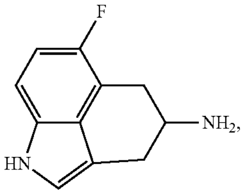
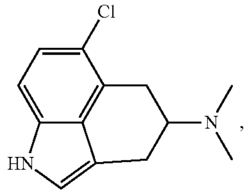
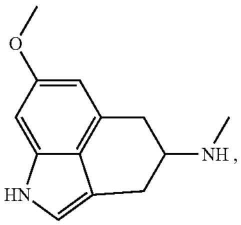
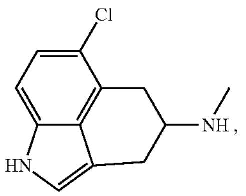
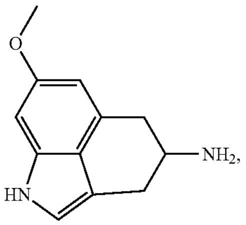
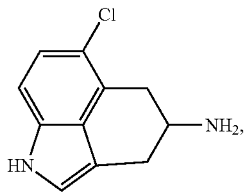

-continued
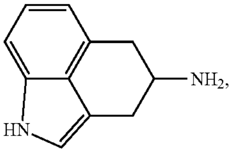 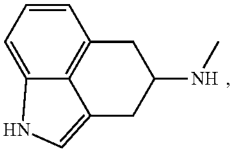
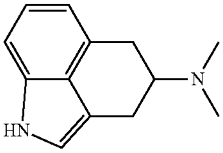 , 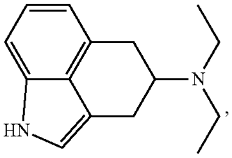 ,
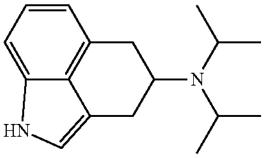 ,
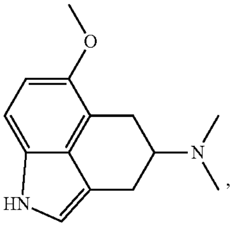 , 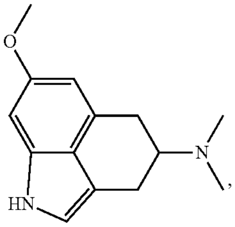 , or
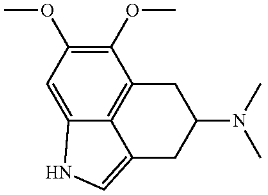 .
In some embodiments, the compound of Formula (Ia), or (Id), or a pharmaceutically acceptable salt thereof, is the compound having a structure that is:
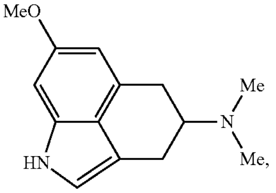
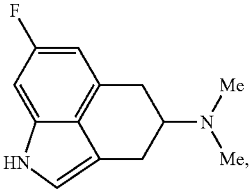 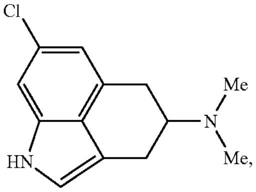
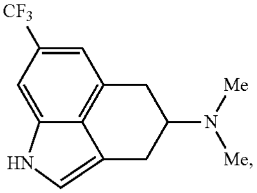
-continued
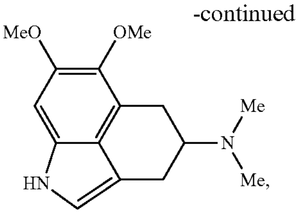
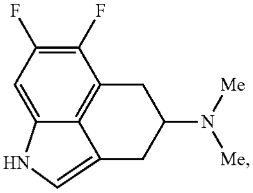 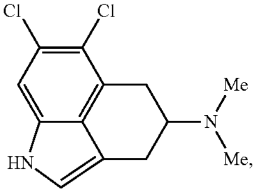
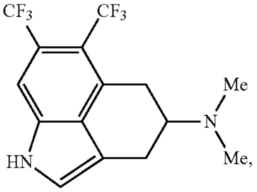 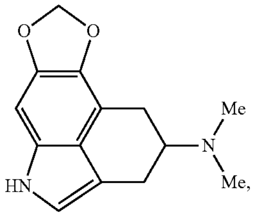
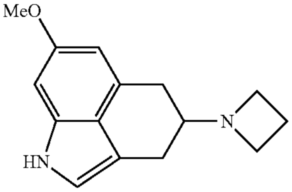 ,
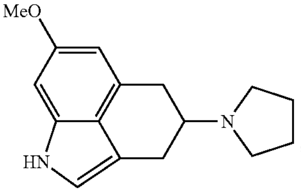 , or
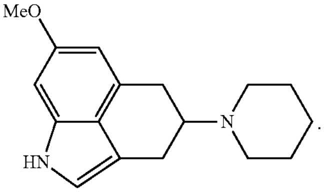 .
In some embodiments, the compound of Formula (Ia), or (Id), or a pharmaceutically acceptable salt thereof, is the compound having a structure that is:
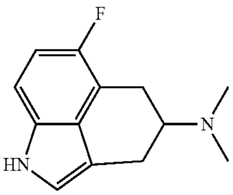 , 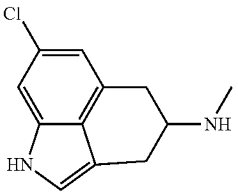 ,
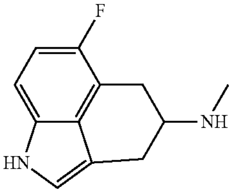 , 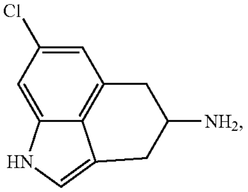

-continued
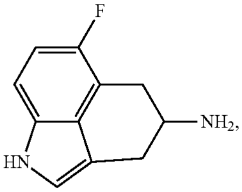
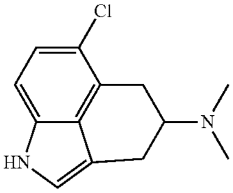
,
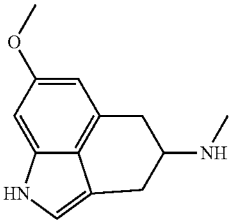
,
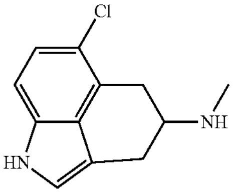
,
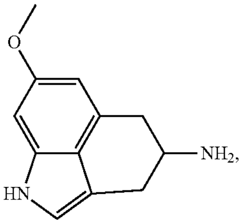
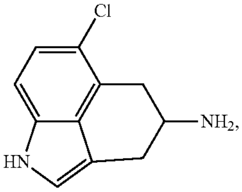
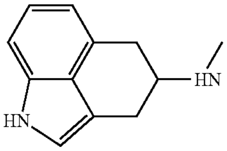
,
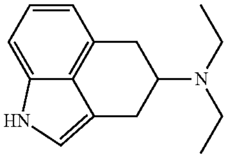
,
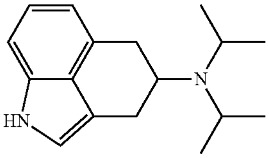
,
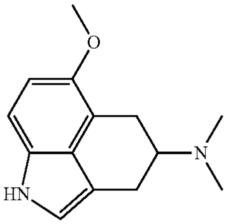
,
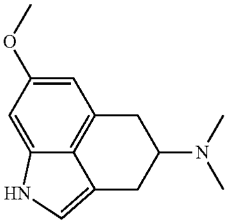
, or
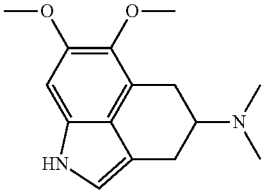
.
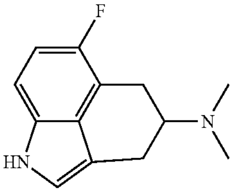
,
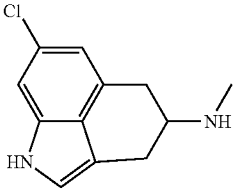
,
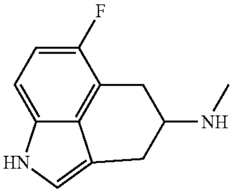
,
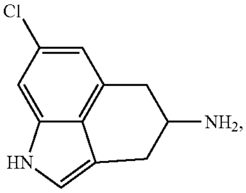
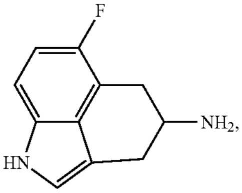
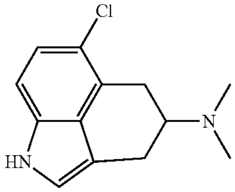
,
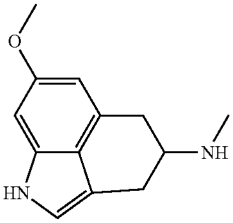
,
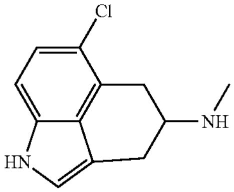
,
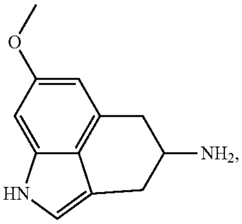
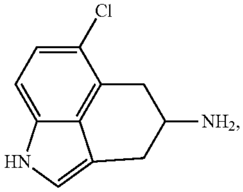
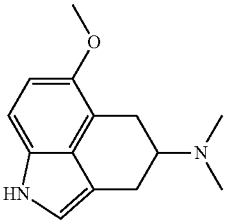
,
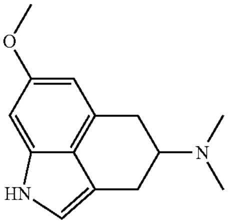
, or
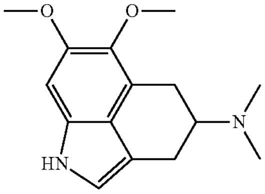
.
In some embodiments, the compound of Formula (Ia), or (Id), or a pharmaceutically acceptable salt thereof, is the compound having a structure that is:

In some embodiments, the compound of Formula (Ia), or (Id), or a pharmaceutically acceptable salt thereof, is the compound having a structure that is:

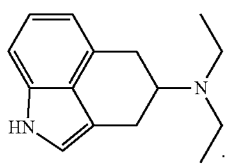 [SMILES: CCN(CC)C1Cc2cccc3[nH]cc(c23)C1]

In some embodiments, the compound of Formula (Ia), (Ia-1), (Ia-2), (Id), (Id-1), or (Id-2), or a pharmaceutically acceptable salt thereof, is the compound having a structure that is:

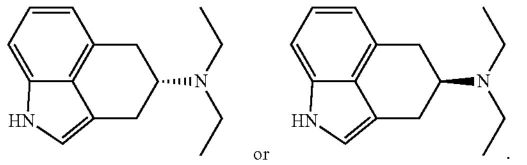 [SMILES: CCN(CC)[C@H]1Cc2cccc3[nH]cc(c23)C1 ; CCN(CC)[C@@H]1Cc2cccc3[nH]cc(c23)C1]

In some embodiments, $R^2$ is combined with $R^{3a}$ and the atoms to which they are attached to form a 5 to 8 membered heterocycloalkyl having 1 to 2 heteroatoms, each heteroatom independently selected from the group consisting of N, O, and S. In some embodiments, the compound of Formula (Ia), (Ia-1), (Ia-2), (Ib), (Ib-1), (Ib-2), or (Ie), or a pharmaceutically acceptable salt thereof, is the compound wherein $R^2$ is combined with $R^{3a}$ and the atoms to which they are attached to form a 5 to 8 membered heterocycloalkyl having 1 to 2 heteroatoms, each independently N, O, or S, wherein the heterocycloalkyl is substituted with $—C(O)N(R^{2a})(R^{2b})$. In some embodiments, the compound of Formula (Ia), (Ia-1), (Ia-2), (Ib), (Ib-1), (Ib-2), or (Ie), or a pharmaceutically acceptable salt thereof, is the compound wherein $R^2$ is combined with $R^{3a}$ and the atoms to which they are attached to form a 5 to 6 membered heterocycloalkyl, wherein the heterocycloalkyl is substituted with $—C(O)N(R^{2a})(R^{2b})$.

In some embodiments, the compound of Formula (Ia), (Ia-1), (Ia-2), (Ib), (Ib-1), (Ib-2), or (Ie), or a pharmaceutically acceptable salt thereof, is the compound wherein $R^2$ is combined with $R^{3a}$ and the atoms to which they are attached to form a 1,2,3,6-tetrahydropyridinyl substituted with $—C(O)N(R^{2a})(R^{2b})$, wherein $R^{2a}$ and $R^{2b}$ are each independently hydrogen or $C_1$-$C_6$ alkyl.

In some embodiments, provided herein is a compound having a structure of Formula (If'):

(If')

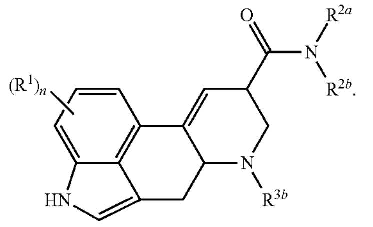

In some embodiments, the compound of Formula (Ia), (Ia-1), or (Ia-2), or a pharmaceutically acceptable salt thereof, is the compound having a structure of Formula (If):

(If)

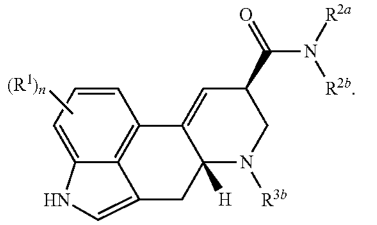

$R^{2a}$ and $R^{2b}$ can be any suitable functional group. In some embodiments, $R^{2a}$ and $R^{2b}$ are each independently hydrogen or $C_{1-6}$ alkyl. In some embodiments, the compound of Formula (Ia), (Ia-1), (Ia-2), or (If), or a pharmaceutically acceptable salt thereof, is the compound wherein $R^{2a}$ and $R^{2b}$ are each independently hydrogen or $C_{1-6}$ alkyl. In some embodiments, the compound of Formula (Ia), (Ia-1), (Ia-2), or (If), or a pharmaceutically acceptable salt thereof, is the compound wherein $R^{2a}$ and $R^{2b}$ are each independently $C_{1-6}$ alkyl. In some embodiments, the compound of Formula (Ia), (Ia-1), (Ia-2), or (If), or a pharmaceutically acceptable salt thereof, is the compound wherein $R^{2a}$ and $R^{2b}$ are each independently methyl, ethyl, n-propyl, isopropyl, n-butyl, sec-butyl, iso-butyl, or tert-butyl. In some embodiments, the compound of Formula (Ia), (Ia-1), (Ia-2), or (If), or a pharmaceutically acceptable salt thereof, is the compound wherein $R^{2a}$ and $R^{2b}$ are each ethyl.

In some embodiments, each $R^1$ is independently hydrogen, methyl, ethyl, n-propyl, isopropyl, n-butyl, sec-butyl, iso-butyl, tert-butyl, —OMe, —OEt, $—OCH_2CH_2CH_3$, $—OCH_2CH_2CH_2CH_3$, —F, —Cl, $—CF_3$, $—CCl_3$, $—CBr_3$ or $—CI_3$; alternatively, two $R^1$ groups on adjacent ring atoms are combined to form a 5 to 6 membered heterocycloalkyl having 2 heteroatoms, each independently O; $R^{2a}$ and $R^{2b}$ are each independently methyl, ethyl, n-propyl, isopropyl, n-butyl, sec-butyl, iso-butyl, or tert-butyl; $R^{3b}$ is hydrogen, methyl, ethyl, isopropyl, or $—CF_3$; and n is 1 or 2. In some embodiments, the compound of Formula (Ia), (Ia-1), (Ia-2), or (If), or a pharmaceutically acceptable salt thereof, is the compound wherein each $R^1$ is independently hydrogen, methyl, ethyl, n-propyl, isopropyl, n-butyl, sec-butyl, iso-butyl, tert-butyl, —OMe, —OEt, $—OCH_2CH_2CH_3$, $—OCH_2CH_2CH_2CH_3$, —F, —Cl, $—CF_3$, $—CCl_3$, $—CBr_3$ or $—CI_3$; alternatively, two $R^1$ groups on adjacent ring atoms are combined to form a 5 to 6 membered heterocycloalkyl having 2 heteroatoms, each independently O; $R^{2a}$ and $R^{2b}$ are each independently methyl, ethyl, n-propyl, isopropyl, n-butyl, sec-butyl, iso-butyl, or tert-butyl; $R^{3b}$ is hydrogen, methyl, ethyl, isopropyl, or $—CF_3$; and n is 1 or 2.

In some embodiments, the compound of Formula (Ia), (Ia-1), (Ia-2), or (If), or a pharmaceutically acceptable salt thereof, is the compound wherein each $R^1$ is independently hydrogen, methyl, ethyl, n-propyl, isopropyl, n-butyl, sec-butyl, iso-butyl, tert-butyl, —OMe, —OEt, —F, —Cl, or $—CF_3$; $R^{2a}$ and $R^{2b}$ are each independently methyl, ethyl, n-propyl, isopropyl, n-butyl, sec-butyl, iso-butyl, or tert-butyl; $R^{3b}$ is hydrogen, methyl, ethyl, isopropyl, or $—CF_3$; and n is 1 or 2. In some embodiments, two $R^1$ groups on adjacent ring atoms are combined to form a 5 to 6 membered heterocycloalkyl having 2 heteroatoms, each independently O; $R^{2a}$ and $R^{2b}$ are each independently methyl, ethyl, n-propyl, isopropyl, n-butyl, sec-butyl, iso-butyl, or tert-butyl; $R^{3b}$ is hydrogen, methyl, ethyl, isopropyl, or $—CF_3$; and n is 1 or 2.

In some embodiments, the compound of Formula (Ia), (Ia-1), (Ia-2), or (If), or a pharmaceutically acceptable salt thereof, is the compound wherein each $R^1$ is independently hydrogen, methyl, —OMe, —F, —Cl, or —$CF_3$; alternatively, two $R^1$ groups on adjacent ring atoms are combined to form a 5 membered heterocycloalkyl having 2 heteroatoms, each independently O; $R^{2a}$ and $R^{2b}$ are each ethyl; $R^{3b}$ is methyl; and n is 1 or 2.

In some embodiments, the compound of Formula (Ia), (Ia-1), (Ia-2), or (If), or a pharmaceutically acceptable salt thereof, is the compound having a structure of Formula (If-1):

(If-1)

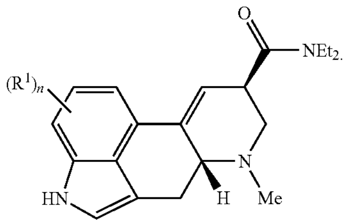

In some embodiments, provided herein is a compound having a structure that is:

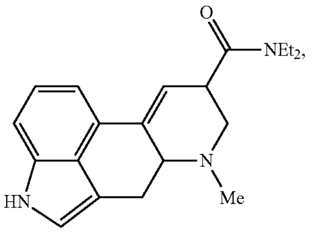

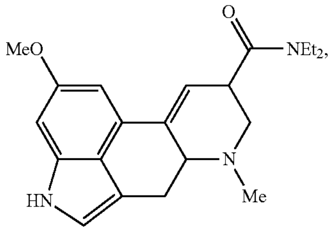

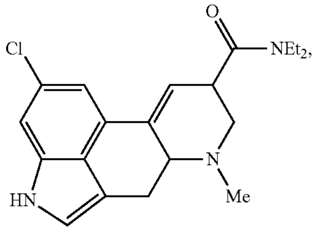

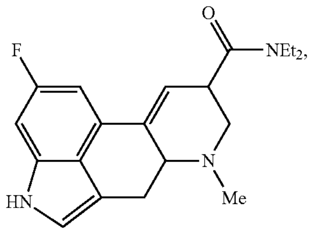

-continued

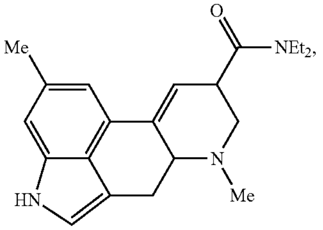

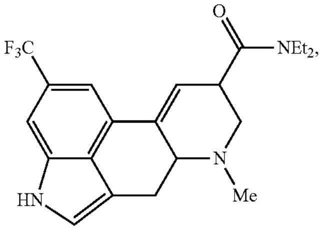

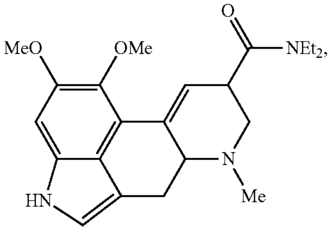

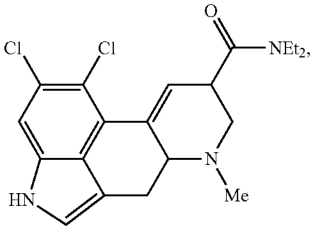

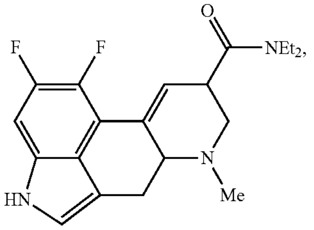

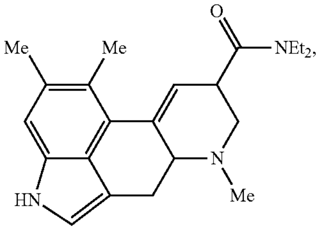

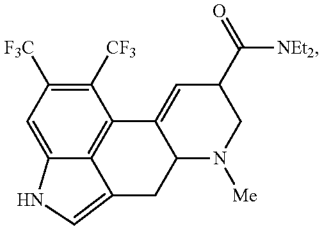

or

-continued
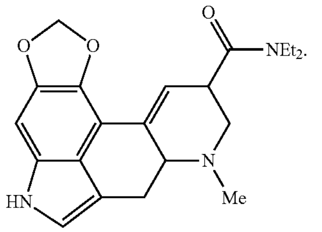
In some embodiments, the compound of Formula (Ia), (Ia-1), (Ia-2), (If), or (If-1), or a pharmaceutically acceptable salt thereof, is the compound having a structure that is:
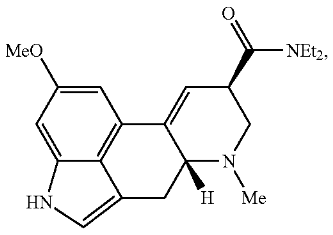
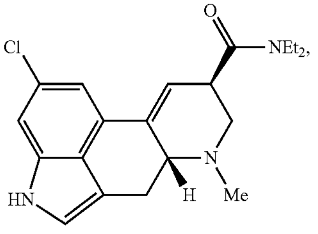
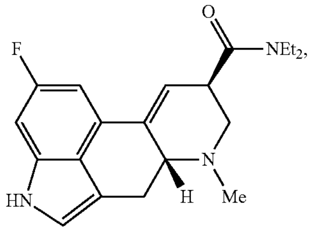
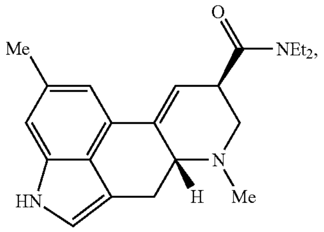
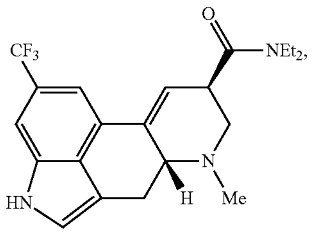
-continued
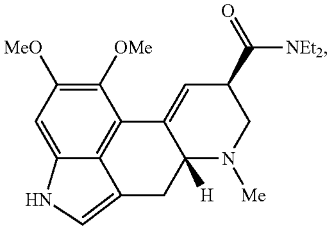
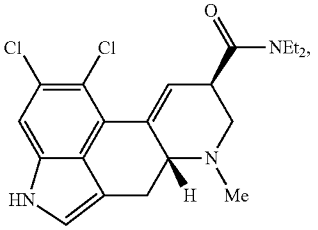
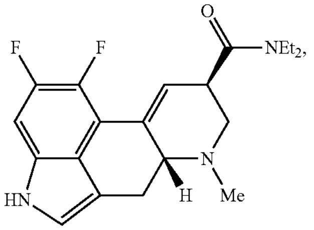
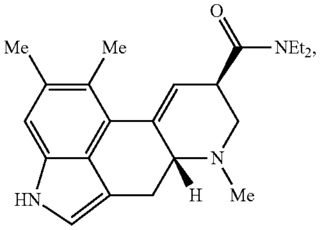
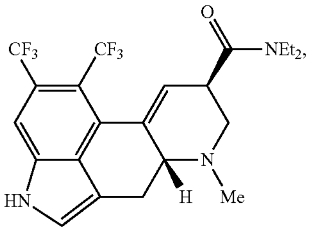
or
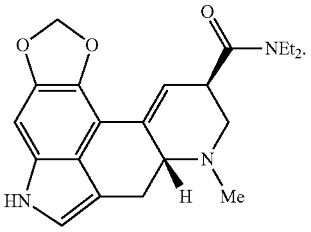
In some embodiments, provided herein is a compound, or a pharmaceutically acceptable salt thereof, having a structure of Formula (Ig) that is:

(Ig)

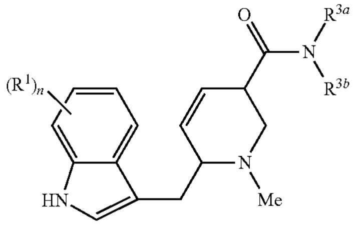

wherein: each $R^1$ is independently $C_{1-6}$ alkyl, $C_{2-6}$ alkenyl, $C_{2-6}$ alkynyl, $C_{1-6}$ alkoxy, $C_{1-6}$ alkoxyalkyl, halogen, $C_{1-6}$ haloalkyl, $C_{1-6}$ haloalkoxy, —$NO_2$, or —CN; alternatively, two $R^1$ groups on adjacent ring atoms are combined to form a 4 to 8 membered heterocycloalkyl having 1 to 2 heteroatoms, each independently N, O, or S; $R^{3a}$ and $R^{3b}$ are each independently hydrogen, $C_{1-6}$ alkyl, or $C_{1-6}$ haloalkyl; alternatively, $R^{3a}$ is combined with $R^{3b}$ and the atom to which they are attached to form a 3 to 8 membered heterocycloalkyl having 1 to 2 heteroatoms, each independently N, O, or S; and subscript n is 0 to 4.

In some embodiments, the compound of Formula (Ig) or a pharmaceutically acceptable salt thereof, is the compound wherein each $R^1$ is independently $C_{1-6}$ alkyl, $C_{1-6}$ alkoxy, halogen, $C_{1-6}$ haloalkyl, or $C_{1-6}$ haloalkoxy; $R^{3a}$ and $R^{3b}$ are each independently hydrogen or $C_{1-6}$ alkyl; and subscript n is 0 to 4. In some embodiments, the compound of Formula (Ig) or a pharmaceutically acceptable salt thereof, is the compound wherein $R^{3a}$ and $R^{3b}$ are each independently hydrogen or $C_{1-6}$ alkyl and n is 0.

In some embodiments, provided herein is a compound, or a pharmaceutically acceptable salt thereof, that is:

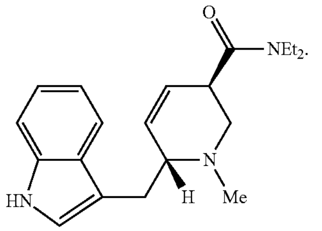

In some embodiments, provided herein is a compound, or a pharmaceutically acceptable salt thereof, having a structure of Formula (II):

(II)

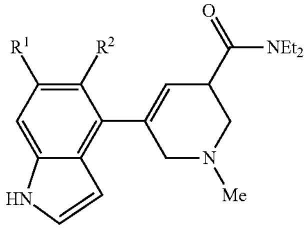

wherein: $R^1$ and $R^2$ are each independently hydrogen, $C_{1-6}$ alkyl, $C_{2-6}$ alkenyl, $C_{2-6}$ alkynyl, $C_{1-6}$ alkoxy, $C_{1-6}$ alkoxyalkyl, halogen, $C_{1-6}$ haloalkyl, $C_{1-6}$ haloalkoxy, —$NO_2$, or —CN; alternatively, $R^1$ and $R^2$ are combined to form a 4 to 8 membered heterocycloalkyl having 1 to 2 heteroatoms, each independently N, O, or S.

In some embodiments, the compound of Formula (II), or a pharmaceutically acceptable salt thereof, is the compound having a structure of Formula (IIa) or Formula (IIb):

(IIa)

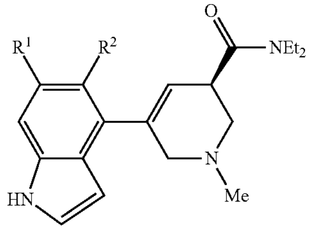

(IIb)

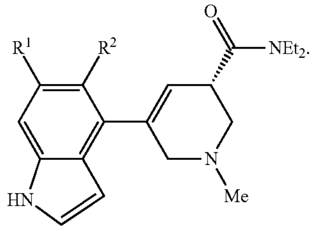

$R^1$ and $R^2$ can be any suitable functional group. In some embodiments, the compound of Formula (II), (IIa), or (IIb), or a pharmaceutically acceptable salt thereof, is the compound wherein $R^1$ and $R^2$ are independently hydrogen, $C_{1-6}$ alkyl, $C_{2-6}$ alkenyl, $C_{2-6}$ alkynyl, $C_{1-6}$ alkoxy, $C_{1-6}$ alkoxyalkyl, halogen, $C_{1-6}$ haloalkyl, $C_{1-6}$ haloalkoxy, —$NO_2$, or —CN; alternatively, $R^1$ and $R^2$ are combined to form a 4 to 8 membered heterocycloalkyl having 1 to 2 heteroatoms, each independently N, O, or S. In some embodiments, the compound of Formula (II), (IIa), or (IIb), or a pharmaceutically acceptable salt thereof, is the compound wherein $R^1$ and $R^2$ are each independently hydrogen, $C_{1-6}$ alkyl, $C_{1-6}$ alkoxy, or $R^1$ and $R^2$ are combined to form a 4 to 8 membered heterocycloalkyl having 1 to 2 heteroatoms, each independently N, O, or S. In some embodiments, the compound of Formula (II), (IIa), or (IIb), or a pharmaceutically acceptable salt thereof, is the compound wherein $R^1$ and $R^2$ are independently hydrogen, $C_{1-6}$ alkyl, or $C_{1-6}$ alkoxy; alternatively, $R^1$ and $R^2$ are combined to form a 4 to 6 membered heterocycloalkyl having 1 to 2 heteroatoms, each independently N, O, or S.

In some embodiments, the compound of Formula (II), (IIa), or (IIb), or a pharmaceutically acceptable salt thereof, is the compound wherein $R^1$ and $R^2$ are independently hydrogen, methyl, ethyl, n-propyl, isopropyl, n-butyl, sec-butyl, iso-butyl, tert-butyl, —OMe, —OEt, —$OCH_2CH_2CH_3$, —$OCH_2CH_2CH_2CH_3$; alternatively, $R^1$ and $R^2$ are combined to form a 4 to 6 membered heterocycloalkyl having 1 to 2 heteroatoms, each independently N, O, or S. In some embodiments, $R^1$ and $R^2$ are independently hydrogen or —$OCH_3$; alternatively, $R^1$ and $R^2$ are combined to form a 4 to 6 membered heterocycloalkyl having 1 to 2 heteroatoms, each independently N, O, or S. In some embodiments, the compound of Formula (II), (IIa), or (IIb), or a pharmaceutically acceptable salt thereof, is the compound wherein $R^1$ and $R^2$ are independently hydrogen or —$OCH_3$; alternatively, $R^1$ and $R^2$ are combined to form a 4 to 6 membered heterocycloalkyl having 1 to 2 heteroatoms, each independently O. In some embodiments, the compound of Formula (II), (IIa), or (IIb), or a pharmaceutically acceptable salt thereof, is the compound wherein $R^1$ and $R^2$ are each independently hydrogen, $C_{1-6}$ alkyl or $C_{1-6}$ alkoxy. In some embodiments, the compound of Formula (II), (IIa), or (IIb), or a pharmaceutically acceptable salt thereof, is the compound wherein $R^1$ and $R^2$ are each independently hydrogen or $C_{1-6}$ alkoxy. In some embodiments, the compound of Formula (II), (IIa), or (IIb), or a pharmaceutically acceptable salt thereof, is the compound wherein $R^1$ and $R^2$ are each hydrogen.

In some embodiments, the compound of Formula (II), or a pharmaceutically acceptable salt thereof, is the compound having a structure that is:

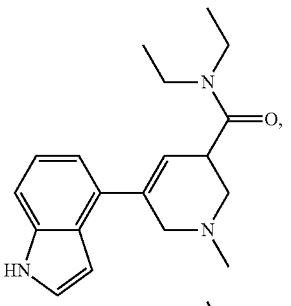

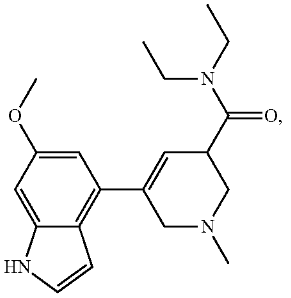

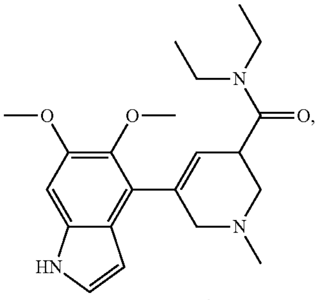
or

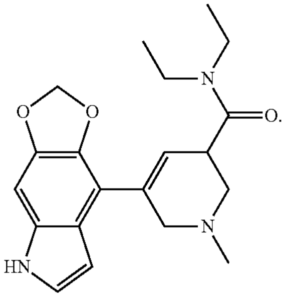

In some embodiments, the compound of Formula (II), or a pharmaceutically acceptable salt thereof, is the compound having a structure that is:

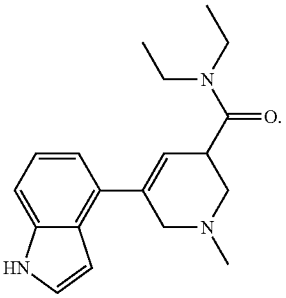 [SMILES: CCN(CC)C(=O)C1C=C(c2cccc3[nH]ccc23)CN(C)C1]

In some embodiments, the compound of Formula (II), (IIa), or (IIb), or a pharmaceutically acceptable salt thereof, is the compound having a structure that is:

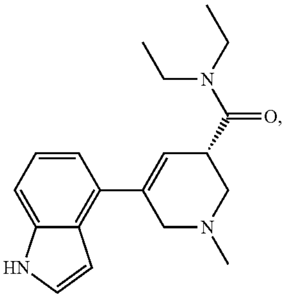
or

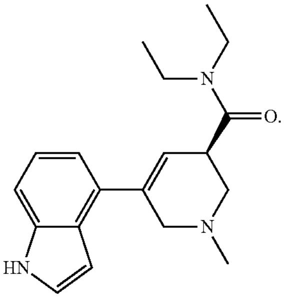

In some embodiments, provided herein is a compound, or a pharmaceutically acceptable salt thereof, having a structure of Formula (IIIa) or Formula (IIIb):

(IIIa)

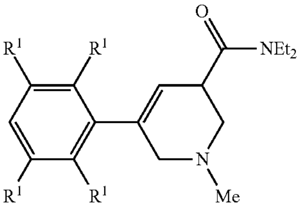

(IIIb)

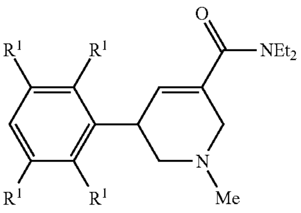

wherein: each $R^1$ is independently hydrogen, $C_{1-6}$ alkyl, $C_{2-6}$ alkenyl, $C_{2-6}$ alkynyl, $C_{1-6}$ alkoxy, $C_{1-6}$ alkoxyalkyl, halogen, $C_{1-6}$ haloalkyl, $C_{1-6}$ haloalkoxy, —$NO_2$, or —CN.

In some embodiments, provided herein is a compound, or a pharmaceutically acceptable salt thereof, having a structure of Formula (IIIa):

(IIIa)

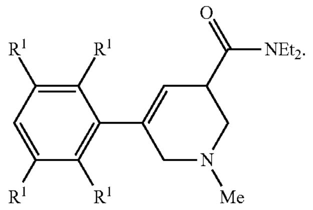

In some embodiments, provided herein is a compound, or a pharmaceutically acceptable salt thereof, having a structure of Formula (IIIb):

(IIIb)

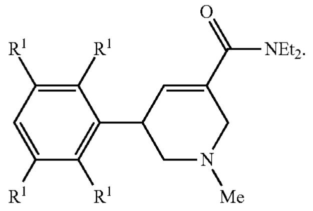

In some embodiments, the compound of Formula (IIIa), or a pharmaceutically acceptable salt thereof, is the compound having a structure of Formula (IIIa-1) or Formula (IIIa-2):

(IIIa-1)

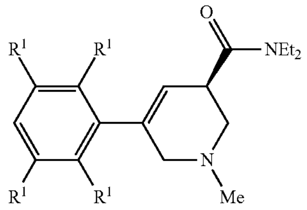

(IIIa-2)

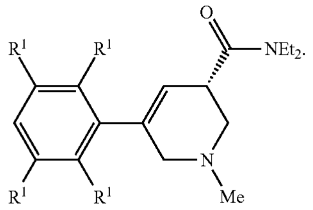

Each $R^1$ can be any suitable functional group. In some embodiments, the compound of Formula (IIIa), (IIIa-1), (IIIa-2), or (IIb), or a pharmaceutically acceptable salt thereof, is the compound wherein each $R^1$ is independently hydrogen, $C_{1-6}$ alkyl, $C_{2-6}$ alkenyl, $C_{2-6}$ alkynyl, $C_{1-6}$ alkoxy, $C_{1-6}$ alkoxyalkyl, halogen, $C_{1-6}$ haloalkyl, $C_{1-6}$ haloalkoxy, —$NO_2$, or —CN. In some embodiments, the compound of Formula (IIIa), (IIIa-1), (IIIa-2), or (IIb), or a pharmaceutically acceptable salt thereof, is the compound wherein each $R^1$ is independently hydrogen, $C_{1-6}$ alkyl, or $C_{1-6}$ alkoxy. In some embodiments, the compound of Formula (IIIa), (IIIa-1), (IIIa-2), or (IIIb), or a pharmaceutically acceptable salt thereof, is the compound wherein each $R^1$ is independently hydrogen, methyl, ethyl, n-propyl, isopropyl, n-butyl, sec-butyl, iso-butyl, tert-butyl, —OMe, —OEt, —$OCH_2CH_2CH_3$, or —$OCH_2CH_2CH_2CH_3$. In some embodiments, the compound of Formula (IIIa), (IIIa-1), (IIIa-2), or (IIIb), or a pharmaceutically acceptable salt thereof, is the compound wherein each $R^1$ is independently hydrogen or —$OCH_3$. In some embodiments, the compound of Formula (IIIa), (IIIa-1), (IIIa-2), or (IIb), or a pharmaceutically acceptable salt thereof, is the compound wherein each $R^1$ is hydrogen.

In some embodiments, the compound of Formula (IIIa), or a pharmaceutically acceptable salt thereof, is the compound having a structure that is:

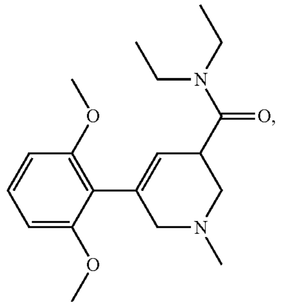

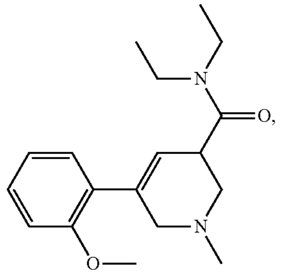

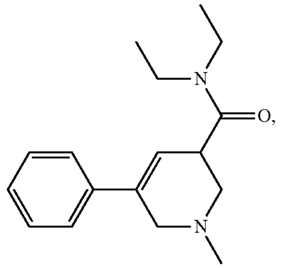

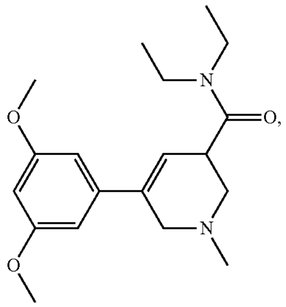

or

-continued
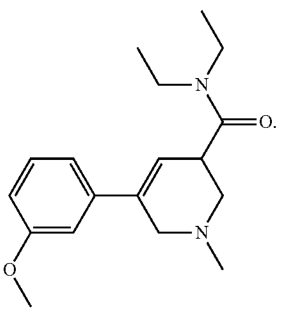
In some embodiments, the compound of Formula (IIIa), (IIIa-1), or (IIIa-2), or a pharmaceutically acceptable salt thereof, is the compound having a structure that is:
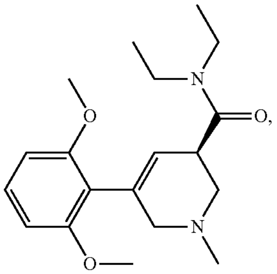
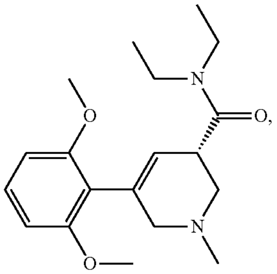
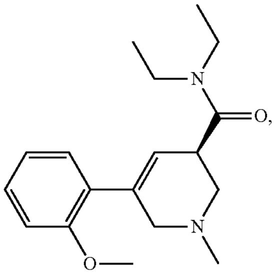
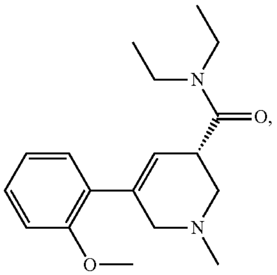
-continued
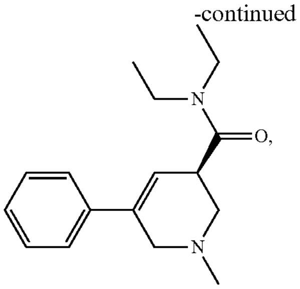
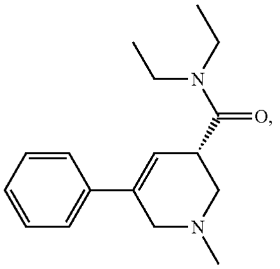
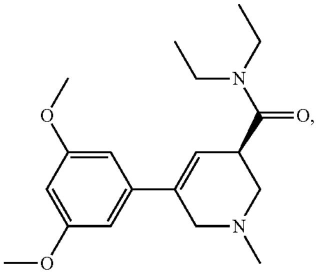
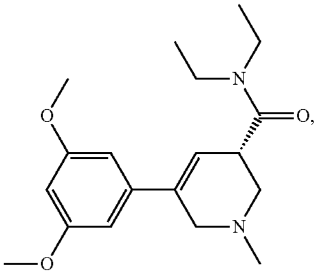
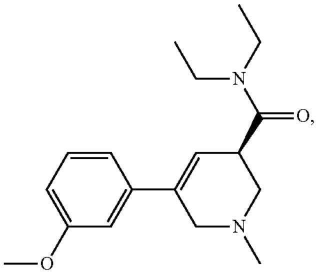
or
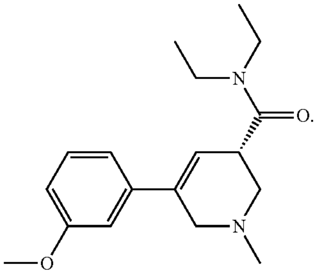
In some embodiments, the compound of Formula (IIIb), or a pharmaceutically acceptable salt thereof, is the compound having a structure that is:

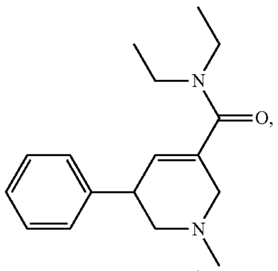

,

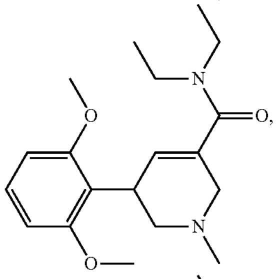

,

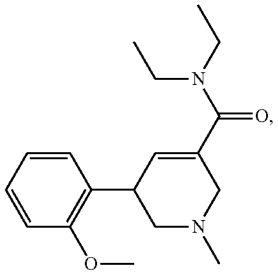

,

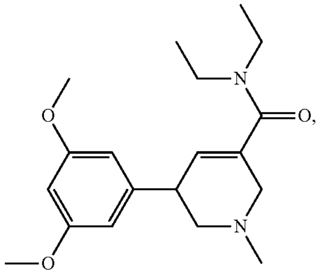

, or

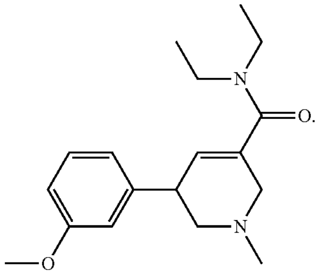

.

The compounds of the present invention can also be in the salt forms, such as acid or base salts of the compounds of the present invention. Illustrative examples of pharmaceutically acceptable salts are mineral acid (hydrochloric acid, hydrobromic acid, phosphoric acid, and the like) salts, organic acid (fumaric acid, acetic acid, propionic acid, glutamic acid, citric acid and the like) salts, quaternary ammonium (methyl iodide, ethyl iodide, and the like) salts. It is understood that the pharmaceutically acceptable salts are non-toxic. Additional information on suitable pharmaceutically acceptable salts can be found in Remington's Pharmaceutical Sciences, 17th ed., Mack Publishing Company, Easton, Pa., 1985, which is incorporated herein by reference.

The present invention also includes isotopically-labeled compounds of the present invention, wherein one or more atoms are replaced by one or more atoms having specific atomic mass or mass numbers. Examples of isotopes that can be incorporated into compounds of the invention include, but are not limited to, isotopes of hydrogen, carbon, nitrogen, oxygen, fluorine, sulfur, and chlorine (such as $^{2}H$, $^{3}H$, $^{13}C$, $^{14}C$, $^{15}N$, $^{18}O$, $^{17}O$, $^{18}F$, $^{35}S$ and $^{36}Cl$). Isotopically-labeled compounds of the present invention are useful in assays of the tissue distribution of the compounds and their prodrugs and metabolites; preferred isotopes for such assays include $^{3}H$ and $^{14}C$. In addition, in certain circumstances substitution with heavier isotopes, such as deuterium ($^{2}H$), can provide increased metabolic stability, which offers therapeutic advantages such as increased in vivo half-life or reduced dosage requirements. Isotopically-labeled compounds of this invention can generally be prepared according to the methods known by one of skill in the art by substituting an isotopically-labeled reagent for a non-isotopically labeled reagent. Compounds of the present invention can be isotopically labeled at positions adjacent to the basic amine, in aromatic rings, and the methyl groups of methoxy substituents.

The present invention includes all tautomers and stereoisomers of compounds of the present invention, either in admixture or in pure or substantially pure form. The compounds of the present invention can have asymmetric centers at the carbon atoms, and therefore the compounds of the present invention can exist in diastereomeric or enantiomeric forms or mixtures thereof. All conformational isomers (e.g., cis and trans isomers) and all optical isomers (e.g., enantiomers and diastereomers), racemic, diastereomeric and other mixtures of such isomers, as well as solvates, hydrates, isomorphs, polymorphs and tautomers are within the scope of the present invention. Compounds according to the present invention can be prepared using diastereomers, enantiomers or racemic mixtures as starting materials. Furthermore, diastereomer and enantiomer products can be separated by chromatography, fractional crystallization or other methods known to those of skill in the art.

5-HT

5-$HT_{2A}$ agonism has been correlated with the promotion of neural plasticity (Ly et al., 2018). 5-$HT_{2A}$ antagonists abrogate the neuritogenesis and spinogenesis effects of hallucinogenic compounds with 5-$HT_{2A}$ agonist activity, e.g., DMT, LSD, and DOI. Furthermore, DMT and other psychedelic compounds promote increased dendritic arbor complexity, dendritic spine density, and synaptogenesis through a 5-$HT_{2A}$-dependent process. Pretreating cortical cultures with a 5-$HT_{2A}$ antagonist blocked the ability of 5-MeO-DMT to increase dendritic growth. Importantly, the psychoplastogenic effects of compounds provided herein are also blocked under these conditions, implicating the 5-$HT_{2A}$ receptor in their mechanism of action. In addition, modulation of the 5-$HT_{2C}$ receptor appears to be important in neuroplasticity as well as various psychological conditions, such as, for example, anxiety, depression, and post-traumatic stress disorder (PTSD).

Furthermore, non-hallucinogenic compounds (e.g., lisuride and 6-MeO-DMT) compete off 5-HT when an $5HT_{2A}$ sensor assay is run in antagonist mode. Additionally, compounds, such as, for example, 6-F-DET, Ketanserin, BOL148, which are non-hallucinogenic in animals (e.g., humans), compete with 5HT binding to $5HT_{2A}$ in an antagonist mode sensor assay. In some embodiments, a compound provided herein prevents binding of 5-HT to $5HT_{2A}$. In some embodiments, the $5HT_{2A}$ sensor assay is in an antagonist mode. In some embodiments, a compound provided herein prevents binding of 5-HT to $5HT_{2A}$ and has non-hallucinogenic potential. In some embodiments, a compound provided herein prevents binding of 5-HT to $5HT_{2A}$ and is non-hallucinogenic. In some embodiments, a compound provided herein prevents binding of 5-HT to $5HT_{2A}$ in antagonist mode has non-hallucinogenic potential. In some embodiments, a compound provided herein prevents binding of 5-HT in antagonist mode is a non-hallucinogenic compound. In some embodiments, a compound provided herein inhibits the response of a sensor assay in antagonist mode has non-hallucinogenic potential. In some embodiments, a compound provided herein inhibits the response of a sensor assay in antagonist mode is a non-hallucinogenic compound.

In some embodiments, the effect of a compound provided herein on an agonist mode sensor assay suggests the compound is a non-hallucinogenic ligand of the $5-HT_{2A}$ receptor and/or the $5-HT_{2C}$ receptor. In some embodiments, the effect of a compound provided herein on an antagonist mode sensor assay suggests the compound is a non-hallucinogenic ligand of the $5-HT_{2A}$ receptor and/or the $5-HT_{2C}$ receptor. In some embodiments, effect of a compound provided herein on an agonist mode and an antagonist mode sensor assay together suggest the compound is a non-hallucinogenic ligand of the $5-HT_{2A}$ receptor and/or the $5-HT_{2C}$ receptor.

Described in some embodiments are non-hallucinogenic compounds that demonstrate similar therapeutic potential as hallucinogenic $5-HT_{2A}$ agonists. In some embodiments, the non-hallucinogenic compounds described herein provide better therapeutic potential than hallucinogenic $5-HT_{2A}$ agonists for neurological diseases. In some embodiments, the compounds of the present invention are modulators of the $5-HT_{2A}$ receptor and/or the $5-HT_{2C}$ receptor and promote neural plasticity (e.g., cortical structural plasticity).

In some embodiments, the compounds provided herein have activity at the $5-HT_{2A}$ receptor and/or the $5-HT_{2C}$ receptor. In some embodiments, the compounds provided herein elicit a biological response by activating the $5-HT_{2A}$ receptor and/or the $5-HT_{2C}$ receptor (e.g., allosteric modulation or modulation of a biological target that activates the $5-HT_{2A}$ receptor and/or the $5-HT_{2C}$ receptor). In some embodiments, the compounds provided herein are selective $5-HT_{2A}$ modulators and promote neural plasticity (e.g., cortical structural plasticity). In some embodiments, promotion of neural plasticity includes, for example, increased dendritic spine growth, increased synthesis of synaptic proteins, strengthened synaptic responses, increased dendritic arbor complexity, increased dendritic branch content, increased spinogenesis, increased neuritogenesis, or any combination thereof. In some embodiments, increased neural plasticity includes, for example, increased cortical structural plasticity in the anterior parts of the brain.

In some embodiments, a compound provided herein (e.g., a $5-HT_{2A}$ modulator and/or a $5-HT_{2C}$ modulator) is non-hallucinogenic. In some embodiments, a compound provided herein (e.g., a $5-HT_{2A}$ modulator and/or a $5-HT_{2C}$ modulator) is used to treat neurological diseases, which modulators do not elicit dissociative side-effects. In some embodiments, the hallucinogenic potential of the compounds described herein is assessed in vitro. In some embodiments, the hallucinogenic potential assessed in vitro of the compounds described herein is compared to the hallucinogenic potential assessed in vitro of hallucinogenic homologs. In some embodiments, the compounds provided herein elicit less hallucinogenic potential in vitro than the hallucinogenic homologs.

In some embodiments, a compound provided herein (e.g., a $5-HT_{2A}$ modulator and/or a $5-HT_{2C}$ modulator) is used to treat neurological diseases. In some embodiments, the neurological diseases comprise decreased neural plasticity, decreased cortical structural plasticity, decreased $5-HT_{2A}$ receptor content, increased $5-HT_{2C}$ receptor content, decreased dendritic arbor complexity, loss of dendritic spines, decreased dendritic branch content, decreased spinogenesis, decreased neuritogenesis, retraction of neurites, or any combination thereof.

In some embodiments, a compound provided herein (e.g., a $5-HT_{2A}$ modulator and/or a $5-HT_{2C}$ modulator) is used for increasing neuronal plasticity. In some embodiments, a compound provided herein (e.g., a $5-HT_{2A}$ modulator and/or a $5-HT_{2C}$ modulator) is used for treating a brain disorder. In some embodiments, a compound provided herein (e.g., a $5-HT_{2A}$ modulator and/or a $5-HT_{2C}$ modulator) is used for increasing at least one of translation, transcription, or secretion of neurotrophic factors.

In some embodiments, a compound provided herein, including pharmaceutically acceptable salts and solvates thereof, is a non-hallucinogenic psychoplastogen. In some embodiments, the non-hallucinogenic psychoplastogen promotes neuronal growth, improves neuronal structure, or a combination thereof.

IV. Pharmaceutical Compositions and Formulations

In some embodiments, provided herein is a pharmaceutical composition, comprising a therapeutically effective amount of a compound of the present invention, or a pharmaceutically acceptable salt thereof.

The compositions of the present invention can be prepared in a wide variety of oral, parenteral and topical dosage forms. Oral preparations include tablets, pills, powder, dragees, capsules, liquids, lozenges, cachets, gels, syrups, slurries, suspensions, etc., suitable for ingestion by the patient. The compositions of the present invention can also be administered by injection, that is, intravenously, intramuscularly, intracutaneously, subcutaneously, intraduodenally, or intraperitoneally. Also, the compositions described herein can be administered by inhalation, for example, intranasally. Additionally, the compositions of the present invention can be administered transdermally. The compositions of this invention can also be administered by intraocular, intravaginal, and intrarectal routes including suppositories, insufflation, powders and aerosol formulations (for examples of steroid inhalants, see Rohatagi, *J. Clin. Pharmacol.* 35:1187-1193, 1995; Tjwa, *Ann. Allergy Asthma Immunol.* 75:107-111, 1995). Accordingly, the present invention also provides pharmaceutical compositions including a pharmaceutically acceptable carrier or excipient and the compound of the present invention.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances, which may also act as diluents, flavoring agents, binders, preservatives, tablet disintegrating agents, or an encapsulating material. Details on techniques for formulation and administration are well described in the scientific and patent literature, see, e.g., the latest edition of Remington's Pharmaceutical Sciences, Maack Publishing Co, Easton PA ("Remington's").

In powders, the carrier is a finely divided solid, which is in a mixture with the finely divided active component. In tablets, the active component is mixed with the carrier having the necessary binding properties in suitable proportions and compacted in the shape and size desired. The powders and tablets preferably contain from 5% or 10% to 70% of the compound the present invention.

Suitable solid excipients include, but are not limited to, magnesium carbonate; magnesium stearate; talc; pectin; dextrin; starch; tragacanth; a low melting wax; cocoa butter; carbohydrates; sugars including, but not limited to, lactose, sucrose, mannitol, or sorbitol, starch from corn, wheat, rice, potato, or other plants; cellulose such as methyl cellulose, hydroxypropylmethyl-cellulose, or sodium carboxymethyl-cellulose; and gums including arabic and tragacanth; as well as proteins including, but not limited to, gelatin and collagen. If desired, disintegrating or solubilizing agents may be added, such as the cross-linked polyvinyl pyrrolidone, agar, alginic acid, or a salt thereof, such as sodium alginate.

Dragee cores are provided with suitable coatings such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound (i.e., dosage). Pharmaceutical preparations of the invention can also be used orally using, for example, push-fit capsules made of gelatin, as well as soft, sealed capsules made of gelatin and a coating such as glycerol or sorbitol. Push-fit capsules can contain the compound of the present invention mixed with a filler or binders such as lactose or starches, lubricants such as talc or magnesium stearate, and, optionally, stabilizers. In soft capsules, the compound of the present invention may be dissolved or suspended in suitable liquids, such as fatty oils, liquid paraffin, or liquid polyethylene glycol with or without stabilizers.

For preparing suppositories, a low melting wax, such as a mixture of fatty acid glycerides or cocoa butter, is first melted and the compound of the present invention is dispersed homogeneously therein, as by stirring. The molten homogeneous mixture is then poured into convenient sized molds, allowed to cool, and thereby to solidify.

Liquid form preparations include solutions, suspensions, and emulsions, for example, water or water/propylene glycol solutions. For parenteral injection, liquid preparations can be formulated in solution in aqueous polyethylene glycol solution.

Aqueous solutions suitable for oral use can be prepared by dissolving the compound of the present invention in water and adding suitable colorants, flavors, stabilizers, and thickening agents as desired. Aqueous suspensions suitable for oral use can be made by dispersing the finely divided active component in water with viscous material, such as natural or synthetic gums, resins, methylcellulose, sodium carboxymethylcellulose, hydroxypropylmethylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethylene oxycetanol), a condensation product of ethylene oxide with a partial ester derived from a fatty acid and a hexitol (e.g., polyoxyethylene sorbitol mono-oleate), or a condensation product of ethylene oxide with a partial ester derived from fatty acid and a hexitol anhydride (e.g., polyoxyethylene sorbitan mono-oleate). The aqueous suspension can also contain one or more preservatives such as ethyl or n-propyl p-hydroxybenzoate, one or more coloring agents, one or more flavoring agents and one or more sweetening agents, such as sucrose, aspartame or saccharin. Formulations can be adjusted for osmolarity.

Also included are solid form preparations, which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

Oil suspensions can be formulated by suspending the compound of the present invention in a vegetable oil, such as arachis oil, olive oil, sesame oil or coconut oil, or in a mineral oil such as liquid paraffin; or a mixture of these. The oil suspensions can contain a thickening agent, such as beeswax, hard paraffin or cetyl alcohol. Sweetening agents can be added to provide a palatable oral preparation, such as glycerol, sorbitol or sucrose. These formulations can be preserved by the addition of an antioxidant such as ascorbic acid. As an example of an injectable oil vehicle, see Minto, *J. Pharmacol. Exp. Ther.* 281:93-102, 1997. The pharmaceutical formulations of the invention can also be in the form of oil-in-water emulsions. The oily phase can be a vegetable oil or a mineral oil, described above, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylene sorbitan mono-oleate. The emulsion can also contain sweetening agents and flavoring agents, as in the formulation of syrups and elixirs. Such formulations can also contain a demulcent, a preservative, or a coloring agent.

The compositions of the present invention can also be delivered as microspheres for slow release in the body. For example, microspheres can be formulated for administration via intradermal injection of drug-containing microspheres, which slowly release subcutaneously (see Rao, *J. Biomater Sci. Polym*. Ed. 7:623-645, 1995; as biodegradable and injectable gel formulations (see, e.g., *Gao Pharm. Res.* 12:857-863, 1995); or, as microspheres for oral administration (see, e.g., Eyles, *J. Pharm. Pharmacol.* 49:669-674, 1997). Both transdermal and intradermal routes afford constant delivery for weeks or months.

In another embodiment, the compositions of the present invention can be formulated for parenteral administration, such as intravenous (IV) administration or administration into a body cavity or lumen of an organ. The formulations for administration will commonly comprise a solution of the compositions of the present invention dissolved in a pharmaceutically acceptable carrier. Among the acceptable vehicles and solvents that can be employed are water and Ringer's solution, an isotonic sodium chloride. In addition, sterile fixed oils can conventionally be employed as a solvent or suspending medium. For this purpose any bland fixed oil can be employed including synthetic mono- or diglycerides. In addition, fatty acids such as oleic acid can likewise be used in the preparation of injectables. These solutions are sterile and generally free of undesirable matter. These formulations may be sterilized by conventional, well known sterilization techniques. The formulations may contain pharmaceutically acceptable auxiliary substances as required to approximate physiological conditions such as pH adjusting and buffering agents, toxicity adjusting agents, e.g., sodium acetate, sodium chloride, potassium chloride, calcium chloride, sodium lactate and the like. The concentration of the compositions of the present invention in these formulations can vary widely, and will be selected primarily based on fluid volumes, viscosities, body weight, and the like, in accordance with the particular mode of administration selected and the patient's needs. For IV administration, the formulation can be a sterile injectable preparation, such as a sterile injectable aqueous or oleaginous suspension. This suspension can be formulated according to the known art using those suitable dispersing or wetting agents and suspending agents. The sterile injectable preparation can also be a sterile injectable solution or suspension in a nontoxic parenterally-acceptable diluent or solvent, such as a solution of 1,3-butanediol.

In another embodiment, the formulations of the compositions of the present invention can be delivered by the use of liposomes which fuse with the cellular membrane or are endocytosed, i.e., by employing ligands attached to the liposome, or attached directly to the oligonucleotide, that bind to surface membrane protein receptors of the cell resulting in endocytosis. By using liposomes, particularly where the liposome surface carries ligands specific for target cells, or are otherwise preferentially directed to a specific organ, one can focus the delivery of the compositions of the present invention into the target cells in vivo. (See, e.g., Al-Muhammed, *J. Microencapsul.* 13:293-306, 1996; Chonn, *Curr. Opin. Biotechnol.* 6:698-708, 1995*; Ostro, Am. J. Hosp. Pharm.* 46:1576-1587, 1989).

The compositions of the present invention can be delivered by any suitable means, including oral, parenteral and topical methods. Transdermal administration methods, by a topical route, can be formulated as applicator sticks, solutions, suspensions, emulsions, gels, creams, ointments, pastes, jellies, paints, powders, and aerosols.

The pharmaceutical preparation is preferably in unit dosage form. In such form the preparation is subdivided into unit doses containing appropriate quantities of the compounds of the present invention. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The compound of the present invention can be present in any suitable amount, and can depend on various factors including, but not limited to, weight and age of the subject, state of the disease, etc. Suitable dosage ranges for the compound of the present invention include from about 0.1 mg to about 10,000 mg, or about 1 mg to about 1000 mg, or about 10 mg to about 750 mg, or about 25 mg to about 500 mg, or about 50 mg to about 250 mg. Suitable dosages for the compound of the present invention include about 1 mg, 5, 10, 20, 30, 40, 50, 60, 70, 80, 90, 100, 200, 300, 400, 500, 600, 700, 800, 900 or 1000 mg.

The compounds of the present invention can be administered at any suitable frequency, interval and duration. For example, the compound of the present invention can be administered once an hour, or two, three or more times an hour, once a day, or two, three, or more times per day, or once every 2, 3, 4, 5, 6, or 7 days, so as to provide the preferred dosage level. When the compound of the present invention is administered more than once a day, representative intervals include 5, 10, 15, 20, 30, 45 and 60 minutes, as well as 1, 2, 4, 6, 8, 10, 12, 16, 20, and 24 hours. The compound of the present invention can be administered once, twice, or three or more times, for an hour, for 1 to 6 hours, for 1 to 12 hours, for 1 to 24 hours, for 6 to 12 hours, for 12 to 24 hours, for a single day, for 1 to 7 days, for a single week, for 1 to 4 weeks, for a month, for 1 to 12 months, for a year or more, or even indefinitely.

The composition can also contain other compatible therapeutic agents. The compounds described herein can be used in combination with one another, with other active agents known to be useful in modulating a glucocorticoid receptor, or with adjunctive agents that may not be effective alone, but may contribute to the efficacy of the active agent.

The compounds of the present invention can be co-administered with another active agent. Co-administration includes administering the compound of the present invention and active agent within 0.5, 1, 2, 4, 6, 8, 10, 12, 16, 20, or 24 hours of each other. Co-administration also includes administering the compound of the present invention and active agent simultaneously, approximately simultaneously (e.g., within about 1, 5, 10, 15, 20, or 30 minutes of each other), or sequentially in any order. Moreover, the compound of the present invention and the active agent can each be administered once a day, or two, three, or more times per day so as to provide the preferred dosage level per day.

In some embodiments, co-administration can be accomplished by co-formulation, i.e., preparing a single pharmaceutical composition including both the compound of the present invention and the active agent. In other embodiments, the compound of the present invention and the active agent can be formulated separately.

The compound of the present invention and the active agent can be present in the compositions of the present invention in any suitable weight ratio, such as from about 1:100 to about 100:1 (w/w), or about 1:50 to about 50:1, or about 1:25 to about 25:1, or about 1:10 to about 10:1, or about 1:5 to about 5:1 (w/w). The compound of the present invention and the other active agent can be present in any suitable weight ratio, such as about 1:100 (w/w), 1:50, 1:25, 1:10, 1:5, 1:4, 1:3, 1:2, 1:1, 2:1, 3:1, 4:1, 5:1, 10:1, 25:1, 50:1 or 100:1 (w/w). Other dosages and dosage ratios of the compound of the present invention and the active agent are suitable in the compositions and methods of the present invention.

V. Methods of Treatment

In some embodiments, provided herein is a method of treating a disease or disorder, such as, but not limited to a neurological disease or disorder, comprising administering to a subject in need thereof, a therapeutically effective amount of a compound of the present invention, or a pharmaceutically acceptable salt thereof, thereby treating the disease or disorder.

In some embodiments, provided herein is a method of treating a disease, comprising administering to a subject in need thereof, a therapeutically effective amount of a compound of the present invention, or a pharmaceutically acceptable salt thereof, thereby treating the disease.

Neurological Disorders

Neuronal plasticity, and changes thereof, have been attributed to many neurological diseases and disorders. For example, during development and in adulthood, changes in dendritic spine number and morphology (e.g., lengths, crossings, density) accompany synapse formation, maintenance and elimination; these changes are thought to establish and remodel connectivity within neuronal circuits. Furthermore, dendritic spine structural plasticity is coordinated with synaptic function and plasticity. For example, spine enlargement is coordinated with long-term potentiation in neuronal circuits, whereas long-term depression is associated with spine shrinkage.

In addition, dendritic spines undergo experience-dependent morphological changes in live animals, and even subtle changes in dendritic spines can affect synaptic function, synaptic plasticity, and patterns of connectivity in neuronal circuits. For example, disease-specific disruptions in dendritic spine shape, size, and/or number accompany neurological diseases and disorders, such as, for example, neurodegenerative (e.g., Alzheimer's disease or Parkinson's disease) and neuropsychiatric (e.g., depression or schizophrenia) diseases and disorders, suggesting that dendritic spines may serve as a common substrate in diseases that involve deficits in information processing.

Unless indicated otherwise, a neurological disease or disorder generally refers to a disease or disorder of the central nervous system (CNS) (e.g., brain, spine, and/or nerves) of an individual.

In some embodiments, provided herein is a method of treating a neurological disease or disorder with a compound provided herein (e.g., a compound of Formula (Ia), Formula (Ia-1), Formula (Ia-2), Formula (Ib), Formula (Ib-1), Formula (Ib-2), Formula (Ic), Formula (Ic-1), Formula (Ic-2), Formula (Id), Formula (Id-1), Formula (Id-2), Formula (Ie), Formula (If), Formula (If-1), Formula (If'), Formula (Ig), Formula (II), Formula (IIa), Formula (IIb), Formula (IIIa), Formula (IIIa-1), Formula (IIIa-2), Formula (IIIb), or a pharmaceutically acceptable salt or solvate thereof).

Provided in some instances herein is a compound useful for the treatment of a variety of brain disorders and other conditions. In some embodiments, the compound provided herein is a 5-$HT_{2A}$ modulator and promotes neural plasticity (e.g., cortical structural plasticity). In some embodiments, the 5-$HT_{2A}$ modulator (e.g., 5-$HT_{2A}$ agonists) is used to treat a brain disorder. In some embodiments, a compound provided herein is a 5-$HT_{2C}$ modulator and promotes neural plasticity (e.g., cortical structural plasticity). In some embodiments, the 5-$HT_{2C}$ modulator is used to treat a brain disorder. In some embodiments, the brain disorder comprises decreased neural plasticity, decreased cortical structural plasticity, decreased 5-$HT_{2A}$ receptor content, increased 5-$HT_{2C}$ receptor content, decreased dendritic arbor complexity, loss of dendritic spines, decreased dendritic branch content, decreased spinogenesis, decreased neuritogenesis, retraction of neurites, or any combination thereof.

In one aspect, a compound provided herein (e.g., a compound of Formula (Ia), Formula (Ia-1), Formula (Ia-2), Formula (Ib), Formula (Ib-1), Formula (Ib-2), Formula (Ic), Formula (Ic-1), Formula (Ic-2), Formula (Id), Formula (Id-1), Formula (Id-2), Formula (Ie), Formula (If), Formula (If-1), Formula (If), Formula (Ig), Formula (II), Formula (IIa), Formula (IIb), Formula (IIIa), Formula (IIIa-1), Formula (IIIa-2), Formula (IIIb), or a pharmaceutically acceptable salt or solvate thereof) improves dendritic spine number and dendritic spine morphology that is lost in a neurological disease or disorder.

In some embodiments, a compound of the present invention is used to treat neurological diseases. In some embodiments, the compounds have, for example, anti-addictive properties, antidepressant properties, anxiolytic properties, or a combination thereof. In some embodiments, the neurological disease is a neuropsychiatric disease. In some embodiments, the neuropsychiatric disease is a mood or anxiety disorder. In some embodiments, the neurological disease is a migraine, headaches (e.g., cluster headache), post-traumatic stress disorder (PTSD), anxiety, depression, neurodegenerative disorder, Alzheimer's disease, Parkinson's disease, psychological disorder, treatment resistant depression, suicidal ideation, major depressive disorder, bipolar disorder, schizophrenia, stroke, traumatic brain injury, and addiction (e.g., substance use disorder). In some embodiments, the neurological disease is a migraine or cluster headache. In some embodiments, the neurological disease is a neurodegenerative disorder, Alzheimer's disease, or Parkinson's disease. In some embodiments, the neurological disease is a psychological disorder, treatment resistant depression, suicidal ideation, major depressive disorder, bipolar disorder, schizophrenia, post-traumatic stress disorder (PTSD), addiction (e.g., substance use disorder), depression, or anxiety. In some embodiments, the neuropsychiatric disease is a psychological disorder, treatment resistant depression, suicidal ideation, major depressive disorder, bipolar disorder, schizophrenia, post-traumatic stress disorder (PTSD), addiction (e.g., substance use disorder), depression, or anxiety. In some embodiments, the neuropsychiatric disease or neurological disease is post-traumatic stress disorder (PTSD), addiction (e.g., substance use disorder), schizophrenia, depression, or anxiety. In some embodiments, the neuropsychiatric disease or neurological disease is addiction (e.g., substance use disorder). In some embodiments, the neuropsychiatric disease or neurological disease is depression. In some embodiments, the neuropsychiatric disease or neurological disease is anxiety. In some embodiments, the neuropsychiatric disease or neurological disease is post-traumatic stress disorder (PTSD). In some embodiments, the neurological disease is stroke or traumatic brain injury. In some embodiments, the neuropsychiatric disease or neurological disease is schizophrenia.

In some embodiments, the disease is a neuropsychiatric disease. In some embodiments, the diseases is a neurodegenerative disease.

In some embodiments, a compound of the present invention is used to treat brain disorders. In some embodiments, the compounds have, for example, anti-addictive properties, antidepressant properties, anxiolytic properties, or a combination thereof. In some embodiments, the brain disorder is a neuropsychiatric disease. In some embodiments, the neuropsychiatric disease is a mood or anxiety disorder. In some embodiments, brain disorders include, for example, migraine, cluster headache, post-traumatic stress disorder (PTSD), anxiety, depression, schizophrenia, and addiction (e.g., substance abuse disorder). In some embodiments, brain disorders include, for example, migraines, addiction (e.g., substance use disorder), depression, and anxiety.

In some embodiments, provided herein is a method for increasing neural plasticity, the method comprising contacting a neuronal cell with a compound of the present invention, or a pharmaceutically acceptable salt thereof, in an amount sufficient to increase neural plasticity of the neuronal cell, wherein the compound produces a maximum number of dendritic crossings with an increase of greater than 1.0 fold by a Sholl Analysis.

Neural plasticity refers to the ability of the brain to change structure and/or function throughout a subject's life. New neurons can be produced and integrated into the central nervous system throughout the subject's life. Increasing neural plasticity includes, but is not limited to, promoting neuronal growth, promoting neuritogenesis, promoting synaptogenesis, promoting dendritogenesis, increasing dendritic arbor complexity, increasing dendritic spine density, and increasing excitatory synapsis in the brain. In some embodiments, increasing neural plasticity comprises promoting neuronal growth, promoting neuritogenesis, promoting synaptogenesis, promoting dendritogenesis, increasing dendritic arbor complexity, and increasing dendritic spine density.

In some embodiments, increasing neural plasticity can treat neurodegenerative disorder, Alzheimer's, Parkinson's disease, psychological disorder, depression, addiction, anxiety, post-traumatic stress disorder, treatment resistant depression, suicidal ideation, major depressive disorder, bipolar disorder, schizophrenia, stroke, traumatic brain injury, or substance use disorder.

In some embodiments, a compound of the present invention is used to increase neural plasticity. In some embodiments, the compounds used to increase neural plasticity have, for example, anti-addictive properties, antidepressant properties, anxiolytic properties, or a combination thereof. In some embodiments, decreased neural plasticity is associated with a neuropsychiatric disease. In some embodiments, the neuropsychiatric disease is a mood or anxiety disorder. In some embodiments, the neuropsychiatric disease includes, for example, migraine, cluster headache, post-traumatic stress disorder (PTSD), schizophrenia, anxiety, depression, and addiction (e.g., substance abuse disorder). In some embodiments, brain disorders include, for example, migraines, addiction (e.g., substance use disorder), depression, and anxiety.

In some embodiments, the experiment or assay to determine increased neural plasticity of any compound of the present invention is a phenotypic assay, a dendritogenesis assay, a spinogenesis assay, a synaptogenesis assay, a Sholl analysis, a concentration-response experiment, a 5-$HT_{2A}$ agonist assay, a 5-$HT_{2A}$ antagonist assay, a 5-$HT_{2A}$ binding assay, or a 5-$HT_{2A}$ blocking experiment (e.g., ketanserin blocking experiments). In some embodiments, the experiment or assay to determine the hallucinogenic potential of any compounds of the present invention is a mouse head-twitch response (HTR) assay.

Compounds of the present invention may have activity as 5-$HT_{2A}$ modulators. In some embodiments, the compounds of the present invention have activity as 5-$HT_{2A}$ modulators. In some embodiments, the compounds of the present invention elicit a biological response by activating the 5-$HT_{2A}$ receptor (e.g., allosteric modulation or modulation of a biological target that activates the 5-$HT_{2A}$ receptor). 5-$HT_{2A}$ agonism has been correlated with the promotion of neural plasticity (Ly et al., 2018). In some embodiments, the $5HT_{2A}$ sensor assay is in an agonist mode or an antagonist mode. In some embodiments, the $5HT_{2A}$ sensor assay is in an agonist mode.

In some embodiments, the compounds described herein are selective 5-$HT_{2A}$ modulators. In some embodiments, the compounds described herein are 5-$HT_{2A}$ modulators and promote neural plasticity (e.g., cortical structural plasticity). In some embodiments, the compounds described herein are selective 5-$HT_{2A}$ modulators and promote neural plasticity (e.g., cortical structural plasticity). In some embodiments, promotion of neural plasticity includes, for example, increased dendritic spine growth, increased synthesis of synaptic proteins, strengthened synaptic responses, increased dendritic arbor complexity, increased dendritic branch content, increased spinogenesis, increased neuritogenesis, or any combination thereof. In some embodiments, increased neural plasticity includes, for example, increased cortical structural plasticity in the anterior parts of the brain.

In some embodiments, non-hallucinogenic 5-$HT_{2A}$ modulators (e.g., 5-$HT_{2A}$ agonists) are used for treating a disease. In some embodiments, non-hallucinogenic 5-$HT_{2A}$ modulators (e.g., 5-$HT_{2A}$ agonists) are used for increasing neural plasticity. In some embodiments, non-hallucinogenic 5-$HT_{2A}$ modulators (e.g., 5-$HT_{2A}$ agonists) are used for increasing neural plasticity and dendritic spine density.

In some embodiments, provided herein is a method for increasing neural plasticity and increasing dendritic spine density, the method comprising contacting a neuronal cell with a compound of the present invention, or a pharmaceutically acceptable salt thereof, in an amount sufficient to increase neural plasticity and increase dendritic spine density of the neuronal cell.

Dendritic spines are dynamic and can have significant changes in density, shape, and volume over time. The growth or loss of dendritic spines, which contribute to the dendritic spine density, can be important for reinforcing neural pathways for learning, memory, and general cognitive function. Increasing dendritic spine density can be useful for treatment of neurological diseases, such as, but not limited to, neurodegenerative diseases and neuropsychiatric diseases.

Increasing dendritic spine density can be measured by staining and immunocytochemical methods known by one of skill in the art. Staining methods include, but are not limited to Golgi staining, crystal violet staining, DAPI staining, and eosin staining. For example, Golgi staining can be used to measure dendritic spine density.

In some embodiments, a compound provided herein, or pharmaceutically acceptable salts thereof, is useful for promoting neuronal growth and/or improving neuronal structure.

In some embodiments, a compound provided herein, or pharmaceutically acceptable salts thereof, is a non-hallucinogenic psychoplastogens useful for treating one or more diseases or disorders associated with loss of synaptic connectivity and/or plasticity.

In some embodiments, an individual administered a compound provided herein does not have a hallucinogenic event (e.g., at any point after the compound has been administered to the individual).

In some embodiments, provided herein is a method for treating a disease or disorder in an individual in need thereof, wherein the disease or disorder is a neurological diseases and disorder.

Provided in some embodiments herein is a compound (e.g., or pharmaceutically acceptable salt or solvate thereof) useful for the modulation of a 5-hydroxytryptamine (5-HT) receptor. In some embodiments, the 5-HT receptor modulated by a compound provided herein is 5-hydroxytryptamine receptor 2A (5-$HT_{2A}$). In some embodiments, the 5-HT receptor modulated by a compound provided herein is 5-hydroxytryptamine receptor 2C (5-$HT_{2C}$).

In some embodiments, provided herein is a modulator of 5-hydroxytryptamine receptor 2A (5-$HT_{2A}$) that is useful for treating one or more diseases or disorders associated with 5-$HT_{2A}$ activity. In some embodiments, provided herein is a modulator of 5-hydroxytryptamine receptor 2C (5-$HT_{2C}$) that is useful for treating one or more diseases or disorders associated with 5-$HT_{2C}$ activity.

In some embodiments, a compound provided herein, or a pharmaceutically acceptable salt thereof, is used in the preparation of medicaments for the treatment of diseases or conditions in a mammal that would benefit from inhibition or reduction of 5-$HT_{2A}$ activity and/or 5-$HT_{2C}$ activity.

In some embodiments, a compound provided herein, or a pharmaceutically acceptable salt thereof, is used in the preparation of medicaments for the treatment of diseases or conditions in a mammal that would benefit from promoting neuronal growth and/or improving neuronal structure.

Methods for treating any of the diseases or conditions described herein in a mammal in need of such treatment, involves administration of pharmaceutical compositions that include at least one compound described herein or a pharmaceutically acceptable salt, active metabolite, prodrug, or pharmaceutically acceptable solvate thereof, in therapeutically effective amounts to said mammal.

In certain embodiments, the compositions containing the compound(s) described herein are administered for prophylactic and/or therapeutic treatments. In certain therapeutic applications, the compositions are administered to a mammal already suffering from a disease or condition, in an amount sufficient to cure or at least partially arrest at least one of the symptoms of the disease or condition. Amounts effective for this use depend on the severity and course of the disease or condition, previous therapy, the mammal's health status, weight, and response to the drugs, and the judgment of a healthcare practitioner. Therapeutically effective amounts are optionally determined by methods including, but not limited to, a dose escalation and/or dose ranging clinical trial.

In prophylactic applications, compositions containing the compounds described herein are administered to a mammal susceptible to or otherwise at risk of a particular disease, disorder or condition. Such an amount is defined to be a "prophylactically effective amount or dose." In this use, the precise amounts also depend on the mammal's state of health, weight, and the like. When used in mammals, effective amounts for this use will depend on the severity and course of the disease, disorder or condition, previous therapy, the mammal's health status and response to the drugs, and the judgment of a healthcare professional. In some embodiments, prophylactic treatments include administering to a mammal, who previously experienced at least one symptom of the disease being treated and is currently in remission, a pharmaceutical composition comprising a compound described herein, or a pharmaceutically acceptable salt thereof, in order to prevent a return of the symptoms of the disease or condition.

In some embodiments wherein the mammal's condition does not improve, upon the discretion of a healthcare professional the administration of the compounds are administered chronically, that is, for an extended period of time, including throughout the duration of the mammal's life in order to ameliorate or otherwise control or limit the symptoms of the mammal's disease or condition.

In some embodiments wherein a mammal's status does improve, the dose of drug being administered is temporarily reduced or temporarily suspended for a certain length of time (i.e., a "drug holiday"). In some embodiments, the length of the drug holiday is between 2 days and 1 year, including by way of example only, 2 days, 3 days, 4 days, 5 days, 6 days, 7 days, 10 days, 12 days, 15 days, 20 days, 28 days, or more than 28 days. The dose reduction during a drug holiday is, by way of example only, by 10%-100%, including by way of example only 10%, 15%, 20%, 25%, 30%, 35%, 40%, 45%, 50%, 55%, 60%, 65%, 70%, 75%, 80%, 85%, 90%, 95%, and 100%.

Once improvement of the patient's conditions has occurred, a maintenance dose is administered if necessary. Subsequently, in specific embodiments, the dosage or the frequency of administration, or both, is reduced, as a function of the symptoms, to a level at which the improved disease, disorder or condition is retained. In some embodiments, however, the mammal requires intermittent treatment on a long-term basis upon any recurrence of symptoms.

The amount of a given agent that corresponds to such an amount varies depending upon factors such as the particular compound, disease condition and its severity, the identity (e.g., weight, sex) of the subject or host in need of treatment, but nevertheless is determined according to the particular circumstances surrounding the case, including, e.g., the specific agent being administered, the route of administration, the condition being treated, and the subject or host being treated.

In general, however, doses employed for adult human treatment are typically in the range of 0.01 mg-5000 mg per day. In some embodiments, doses employed for adult human treatment are from about 1 mg to about 1000 mg per day. In some embodiments, the desired dose is conveniently presented in a single dose or in divided doses administered simultaneously or at appropriate intervals, for example as two, three, four or more sub-doses per day.

In some embodiments, the daily dosages appropriate for the compound described herein, or a pharmaceutically acceptable salt thereof, are from about 0.01 to about 50 mg/kg per body weight. In some embodiments, the daily dosage or the amount of active in the dosage form are lower or higher than the ranges indicated herein, based on a number of variables in regard to an individual treatment regime. In some embodiments, the daily and unit dosages are altered depending on a number of variables including, but not limited to, the activity of the compound used, the disease or condition to be treated, the mode of administration, the requirements of the individual subject, the severity of the disease or condition being treated, and the judgment of the practitioner.

Toxicity and therapeutic efficacy of such therapeutic regimens are determined by standard pharmaceutical procedures in cell cultures or experimental animals, including, but not limited to, the determination of the $LD_{50}$ and the $ED_{50}$. The dose ratio between the toxic and therapeutic effects is the therapeutic index and it is expressed as the ratio between $LD_{50}$ and $ED_{50}$. In some embodiments, the data obtained from cell culture assays and animal studies are used in formulating the therapeutically effective daily dosage range and/or the therapeutically effective unit dosage amount for use in mammals, including humans. In some embodiments, the daily dosage amount of the compounds described herein lies within a range of circulating concentrations that include the $ED_{50}$ with minimal toxicity. In some embodiments, the daily dosage range and/or the unit dosage amount varies within this range depending upon the dosage form employed and the route of administration utilized.

In any of the aforementioned aspects are further embodiments in which the effective amount of the compound described herein, or a pharmaceutically acceptable salt thereof, is: (a) systemically administered to the mammal; and/or (b) administered orally to the mammal; and/or (c) intravenously administered to the mammal; and/or (d) administered by injection to the mammal; and/or (e) administered topically to the mammal; and/or (f) administered non-systemically or locally to the mammal.

In any of the aforementioned aspects are further embodiments comprising single administrations of the effective amount of the compound, including further embodiments in which (i) the compound is administered once a day; or (ii) the compound is administered to the mammal multiple times over the span of one day.

In any of the aforementioned aspects are further embodiments comprising multiple administrations of the effective amount of the compound, including further embodiments in which (i) the compound is administered continuously or intermittently: as in a single dose; (ii) the time between multiple administrations is every 6 hours; (iii) the compound is administered to the mammal every 8 hours; (iv) the compound is administered to the mammal every 12 hours; (v) the compound is administered to the mammal every 24 hours. In further or alternative embodiments, the method comprises a drug holiday, wherein the administration of the compound is temporarily suspended or the dose of the compound being administered is temporarily reduced; at the end of the drug holiday, dosing of the compound is resumed. In one embodiment, the length of the drug holiday varies from 2 days to 1 year.

In some embodiments, the therapeutic effectiveness of one of the compounds described herein is enhanced by administration of an adjuvant (i.e., by itself the adjuvant has minimal therapeutic benefit, but in combination with another therapeutic agent, the overall therapeutic benefit to the patient is enhanced). Or, in some embodiments, the benefit experienced by a patient is increased by administering one of the compounds described herein with another agent (which also includes a therapeutic regimen) that also has therapeutic benefit.

In some embodiments, different therapeutically-effective dosages of the compounds disclosed herein will be utilized in formulating pharmaceutical composition and/or in treatment regimens when the compounds disclosed herein are administered in combination with one or more additional agent, such as an additional therapeutically effective drug, an adjuvant or the like. Therapeutically-effective dosages of drugs and other agents for use in combination treatment regimens is optionally determined by means similar to those set forth hereinabove for the actives themselves. Furthermore, the methods of prevention/treatment described herein encompasses the use of metronomic dosing, i.e., providing more frequent, lower doses in order to minimize toxic side effects. In some embodiments, a combination treatment regimen encompasses treatment regimens in which administration of a compound described herein, or a pharmaceutically acceptable salt thereof, is initiated prior to, during, or after treatment with a second agent described herein, and continues until any time during treatment with the second agent or after termination of treatment with the second agent. It also includes treatments in which a compound described herein, or a pharmaceutically acceptable salt thereof, and the second agent being used in combination are administered simultaneously or at different times and/or at decreasing or increasing intervals during the treatment period. Combination treatment further includes periodic treatments that start and stop at various times to assist with the clinical management of the patient.

It is understood that the dosage regimen to treat, prevent, or ameliorate the disease(s) for which relief is sought, is modified in accordance with a variety of factors (e.g. the disease or disorder from which the subject suffers; the age, weight, sex, diet, and medical condition of the subject). Thus, in some instances, the dosage regimen actually employed varies and, in some embodiments, deviates from the dosage regimens set forth herein.

VI. Examples

General Synthetic Scheme 1

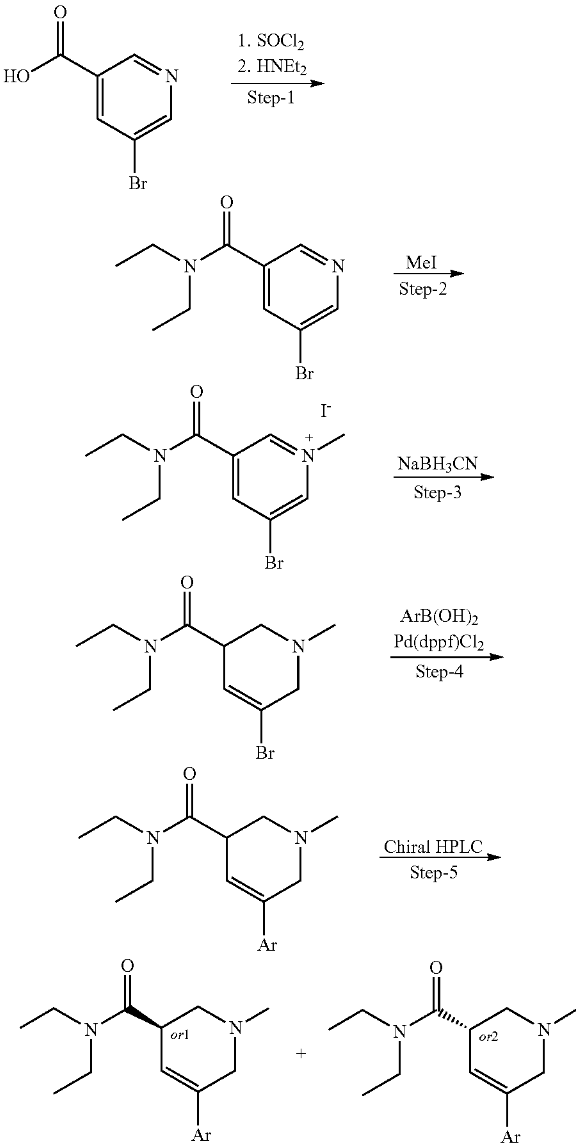

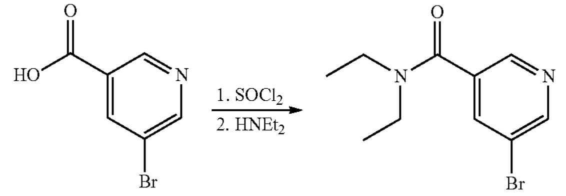

I-1 I-2

Step 1-1—Preparation of 5-bromo-N,N-diethylnicotinamide (I-2): To intermediate I-1 (15 g, 74.25 mmol, 1.0 eq) was added $SOCl_2$ (75 mL, 5 vol) at 0° C. and the reaction mixture was heated under reflux for 3 h. The crude reaction mixture was dried by evaporation in vacuo and dried further by azeotropic co-evaporation with toluene (2×50 mL). The residue was dissolved in dichloromethane (175 mL) and triethylamine (31.3 mL, 222.6 mmol, 3.0 eq) and diethylamine (15.5 mL, 148.4 mmol, 2.0 eq) were added at 0° C.

The reaction mixture was allowed to warm to room temperature and stirred for additional 16 h. The crude reaction mixture was washed with saturated aqueous solution of NaHCO3 and extracted with ethyl acetate. The combined organic layers were washed with aqueous solution of NaCl, the combined organic layers were dried over anhydrous $Na_2SO_4$, solids were removed by filtration and the filtrate was concentrated in vacuo to obtain crude reaction residue that was used in the next step without further purification. I-2 (16 g, 83%, pale brown syrup). $^1$H NMR ($CDCl_3$, 400 MHz): δ 8.71 (d, J=2.1 Hz, 1H), 8.55 (d, J=1.8 Hz, 1H), 7.87 (t, J=2.0 Hz, 1H), 3.61-3.23 (m, 4H), 1.28-1.13 (m, 6H).

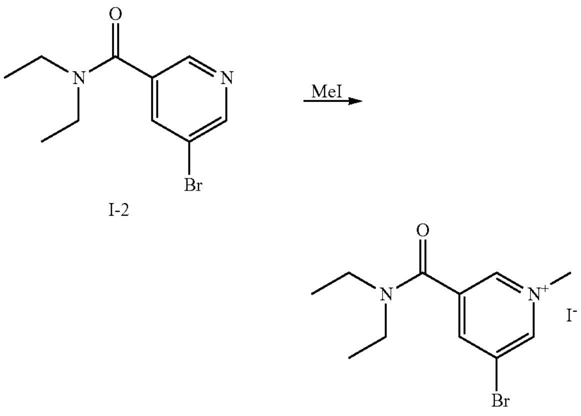

I-2

I-3

Step 1-2—Preparation of 3-bromo-5-(diethylcarbamoyl)-1-methylpyridin-1-ium (I-3): To a stirred solution of I-2 (17 g, 66.1 mmol, 1.0 eq) in acetonitrile (170 mL) was added MeI (8.23 mL, 132.2 mmol, 2.0 eq) at 0° C. and the reaction mixture was stirred for 10 minute and then stirred under reflux for additional 16 h. Volatiles were removed by evaporated in vacuo and the crude residue was triturated with diethyl ether twice to obtain I-3 (26 g, 100%, yellow solid). $^1$H NMR (DMSO-$d_6$, 400 MHz): δ 9.48 (s, 1H), 9.21 (s, 1H), 8.98 (t, J=1.4 Hz, 1H), 4.31 (s, 3H), 3.48 (q, J=7.1 Hz, 2H), 3.23 (q, J=7.0 Hz, 2H), 1.18 (t, J=7.1 Hz, 3H), 1.12-1.01 (m, 3H).

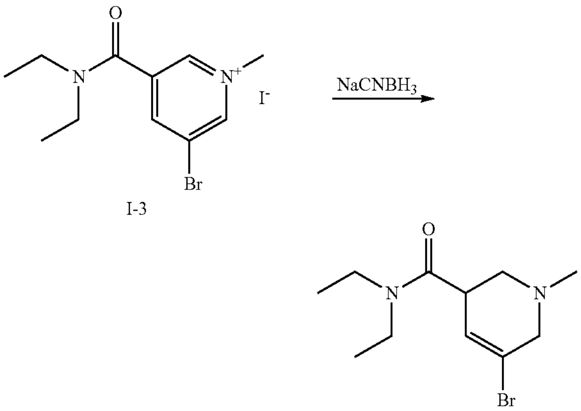

I-3

I-4

Step 1-3—Preparation of 5-bromo-N,N-diethyl-1-methyl-1,2,3,6-tetrahydropyridine-3-carboxamide (I-4): To a stirred solution of I-3 (15 g, 37.5 mmol, 1.0 eq) in MeOH (750 ml) were added portion-wise $NaCNBH_3$ (7.08 g, 112.7 mmol, 3.0 eq) and acetic acid (11.27 g, 187.9 mmol, 5.0 eq) at 0° C. The reaction mixture was allowed to warm to room temperature and stirred for 16 h. Volatiles were evaporated in vacuo pressure and a solution of NaOH (150 mL, 1.0M in water) was added. The crude reaction mixture extracted with ethyl acetate, the combined organic layers were washed with an aqueous solution of NaCl, the organic layer was dried over anhydrous $Na_2SO_4$, solids were removed by filtration and the filtrate was concentrated in vacuo to provide crude I-4. The crude I-4 was purified by silica gel chromatography (1% MeOH/$CH_2Cl_2$) to provide I-4 (4.9 g, 47%, pale-yellow syrup). $^1$H NMR ($CDCl_3$, 400 MHz): δ 6.01-5.96 (m, 1H), 3.75-3.51 (m, 1H), 3.40-3.31 (m, 5H), 3.15-3.03 (m, 1H), 2.88 (dd, J=11.6, 5.3 Hz, 1H), 2.64 (dd, J=11.5, 9.8 Hz, 1H), 2.40 (s, 3H), 1.23-1.18 (m, 3H), 1.11 (t, J=7.1 Hz, 3H).

Example 1: Preparation of N,N-diethyl-1-methyl-5-phenyl-1,2,3,6-tetrahydropyridine-3-carboxamide (I-5)

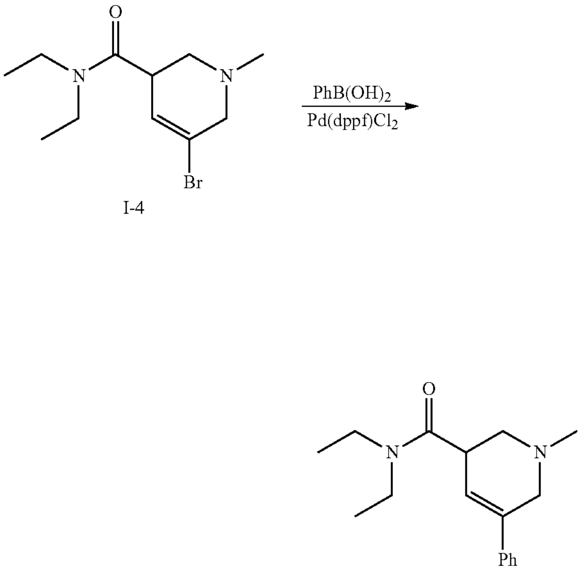

I-4

I-5

To a stirred solution of I-4 (1 g, 3.6 mmol, 1.0 eq) in a mixture of dioxane/water (10 mL, 2:1, 10 vol) were added phenylboronic acid (527 mg, 4.3 mmol, 1.2 eq), followed by $K_2CO_3$ (1.5 g, 10.9 mmol, 3.0 eq) at room temperature. The reaction mixture was degassed under $N_2$ atmosphere for 30 minutes and $Pd(dppf)Cl_2 \cdot CH_2Cl_2$ (296 mg, 0.3 mmol, 0.1 eq) was added under $N_2$ atmosphere at room temperature. The reaction mixture was stirred at 80° C. for 12 h, allowed to cool to room temperature, washed with water and extracted with ethyl acetate. The combined organic layers were washed with an aqueous solution of NaCl, the organic layer was dried over anhydrous $Na_2SO_4$, solids were removed by filtration and the filtrate was concentrated in vacuo. The crude reaction product was purified by silica gel chromatography (1% MeOH in $CH_2Cl_2$) to obtain I-5 (700 mg, 70%, pale-brown liquid). $^1$H NMR ($CDCl_3$, 400 MHz): δ 7.42-7.23 (m, 5H), 5.96 (br s, 1H), 3.84-3.75 (m, 1H), 3.65-3.55 (m, 1H), 3.55-3.36 (m, 4H), 3.20-3.10 (m, 1H), 3.02-2.91 (m, 1H), 2.73-2.60 (m, 1H), 2.51 (s, 3H), 1.32-1.19 (m, 3H), 1.18-1.06 (m, 3H).

Example 2: Compounds 1 and 2 Via Chiral Resolution of I-5

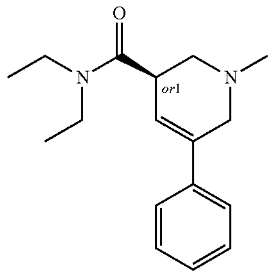

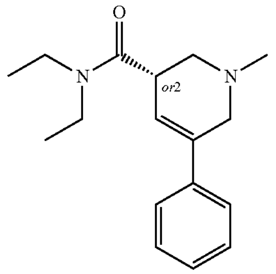

Racemic I-5 (200 mg) was separated into its enantiomers by using SFC chiral HPLC (Chiralpak IG 250×30 5 μm, 10%-50% gradient of 0.1% ammonia/$CH_3OH$ in $CO_2$, 80.0 mL/min). The first eluting enantiomer had a retention time of 4.81 minutes and the second eluting enantiomer had a retention time of 6.31 minutes.

Compound 1: 55.8 mg, yellow thick liquid. LC-MS: 99.8%, m/z=273.1 $[M+H]^+$; $^1H$ NMR ($CDCl_3$, 400 MHz): δ 7.42-7.23 (m, 5H), 5.96 (br s, 1H), 3.84-3.75 (m, 1H), 3.65-3.55 (m, 1H), 3.55-3.36 (m, 4H), 3.20-3.10 (m, 1H), 3.02-2.91 (m, 1H), 2.73-2.60 (m, 1H), 2.51 (s, 3H), 1.32-1.19 (m, 3H), 1.18-1.06 (m, 3H).

Compound 2: 51.6 mg, yellow thick liquid, LC-MS: 99.5%, m/z=273.4 $[M+H]^+$; $^1H$ NMR ($CDCl_3$, 400 MHz): δ 7.40-7.28 (m, 5H), 5.98-5.93 (m, 1H), 3.80 (br s, 1H), 3.65-3.56 (m, 1H), 3.50-3.39 (m, 4H), 3.21-3.12 (m, 1H), 2.96 (br dd, J=10.5, 5.1 Hz, 1H), 2.71-2.62 (m, 1H), 2.53-2.48 (m, 3H), 1.31-1.22 (m, 3H), 1.19-1.12 (m, 3H).

Example 3: Preparation of N,N-diethyl-1-methyl-5-phenyl-1,2,3,6-tetrahydropyridine-3-carboxamide (I-6)

I-6

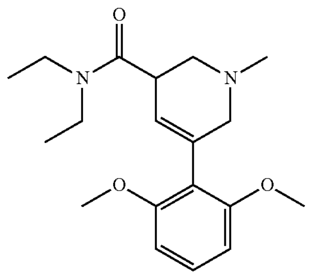

Intermediate I-6 was prepared as described for Intermediate I-5 but using (2,6-dimethoxyphenyl) boronic acid instead of phenylboronic acid. 200 mg, 66%, brown liquid. $^1H$ NMR ($CDCl_3$, 400 MHz): δ 7.23-7.15 (m, 1H), 6.58-6.51 (m, 2H), 5.59-5.52 (m, 1H), 3.95 (br s, 1H), 3.77 (br s, 6H), 3.54-3.32 (m, 5H), 3.24-3.05 (m, 2H), 3.04-2.92 (m, 1H), 2.60-2.51 (m, 3H), 1.26-1.17 (m, 3H), 1.10 (br s, 3H).

Example 4: Compounds 3 and 4 Via Chiral Resolution of I-6

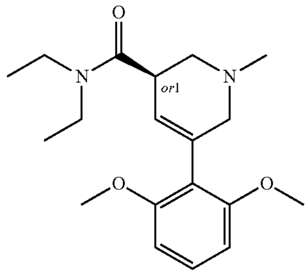

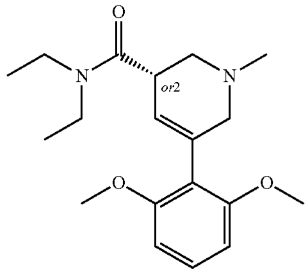

Racemic I-6 (200 mg) was separated into its enantiomers by using SFC chiral HPLC (Chiralpak IC 250×30 5μ, 20%-50% gradient of 0.1% ammonia/$CH_3OH$ in $CO_2$, 80.0 mL/min). The first eluting enantiomer had a retention time of 11.05 minutes and the second eluting enantiomer had a retention time of 13.27 minutes.

Compound 3: 35.5 mg, light brown gummy solid, LC-MS: 99.7%, m/z=333.1 $[M+H]^+$; $^1H$ NMR ($CDCl_3$, 400 MHz): δ 7.23-7.15 (m, 1H), 6.58-6.51 (m, 2H), 5.59-5.52 (m, 1H), 3.95 (br s, 1H), 3.77 (br s, 6H), 3.54-3.32 (m, 5H), 3.24-3.05 (m, 2H), 3.04-2.92 (m, 1H), 2.60-2.51 (m, 3H), 1.26-1.17 (m, 3H), 1.10 (br s, 3H).

Compound 4: 35.5 mg, brown gummy solid, LC-MS: 99.5%, m/z=333.5 $[M+H]^+$; $^1H$ NMR ($CDCl_3$, 400 MHz): δ 7.23-7.14 (m, 1H), 6.58-6.50 (m, 2H), 5.57-5.49 (m, 1H), 3.93-3.83 (m, 1H), 3.81-3.69 (m, 6H), 3.54-3.26 (m, 5H), 3.12-2.97 (m, 2H), 2.91-2.79 (m, 1H), 2.54-2.41 (m, 3H), 1.27-1.16 (m, 3H), 1.15-1.05 (m, 3H).

Example 5: Preparation of 5-(3,5-dimethoxyphenyl)-N,N-diethyl-1-methyl-1,2,3,6-tetrahydropyridine-3-carboxamide (I-7)

I-7

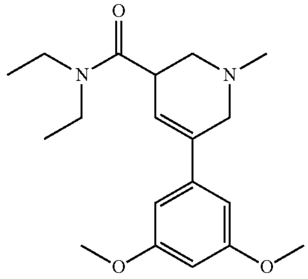

Intermediate I-7 was prepared as described for intermediate I-5 but using (3,5-dimethoxyphenyl) boronic acid instead of phenylboronic acid. 170 mg, 56%, brown liquid, $^{1}H$ NMR ($CDCl_3$, 400 MHz): δ 6.53-6.47 (m, 2H), 6.41-6.36 (m, 1H), 5.96-5.89 (m, 1H), 3.82-3.74 (m, 7H), 3.59-3.50 (m, 1H), 3.47-3.35 (m, 4H), 3.16-3.05 (m, 1H), 2.98-2.88 (m, 1H), 2.70-2.60 (m, 1H), 2.51-2.45 (m, 3H), 1.29-1.20 (m, 3H), 1.18-1.09 (m, 3H).

Example 6: Compounds 6 and 6 Via Chiral Resolution of I-7

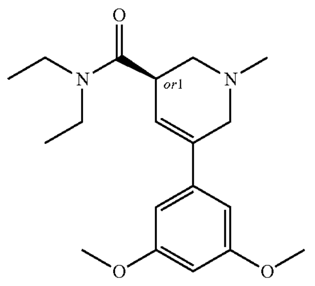

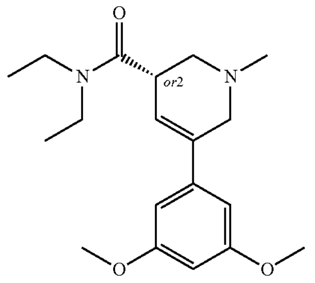

(R)-5-(3,5-dimethoxyphenyl)-N,N-diethyl-1-methyl-1,2,3,6-tetrahydropyridine-3-carboxamide and (S)-5-(3,5-dimethoxyphenyl)-N,N-diethyl-1-methyl-1,2,3,6-tetrahydropyridine-3-carboxamide Racemic I-7 (200 mg) was separated into its enantiomers by using SFC chiral HPLC (Chiralpak IG 250×30 5μ, 70%:30% gradient of 0.1% isopropyl amine/n-hexane and $CH_2Cl_2$ (50%):MeOH (50%), 25.0 mL/min). The first eluting enantiomer had a retention time of 4.31 minutes and the second eluting enantiomer had a retention time of 6.67 minutes.

Compound 5: 67 mg. brown solid, LC-MS: 98.5%, m/z=333.5 $[M+H]^+$; $^{1}H$ NMR ($CDCl_3$, 400 MHz): δ 6.53-6.47 (m, 2H), 6.41-6.36 (m, 1H), 5.96-5.89 (m, 1H), 3.82-3.74 (m, 7H), 3.59-3.50 (m, 1H), 3.47-3.35 (m, 4H), 3.16-3.05 (m, 1H), 2.98-2.88 (m, 1H), 2.70-2.60 (m, 1H), 2.51-2.45 (m, 3H), 1.29-1.20 (m, 3H), 1.18-1.09 (m, 3H).

Compound 6: 67 mg brown, solid, LC-MS: 98.3%, m/z=333.5 $[M+H]^+$; $^{1}H$ NMR ($CDCl_3$, 400 MHz): δ 6.53-6.47 (m, 2H), 6.41-6.36 (m, 1H), 5.96-5.91 (m, 1H), 3.82-3.73 (m, 7H), 3.58-3.50 (m, 1H), 3.46-3.35 (m, 4H), 3.16-3.05 (m, 1H), 2.99-2.86 (m, 1H), 2.69-2.60 (m, 1H), 2.48 (br s, 3H), 1.28-1.20 (m, 3H), 1.13 (br t, J=6.6 Hz, 3H).

Example 7: Preparation of N,N-diethyl-5-(2-methoxyphenyl)-1-methyl-1,2,3,6-tetrahydropyridine-3-carboxamide (I-8)

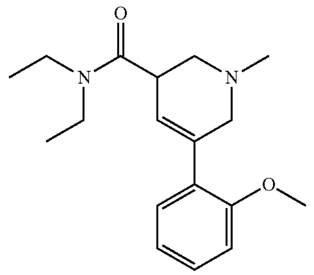

I-8

Intermediate I-8 was prepared as described for intermediate I-5 but using 2-methoxyphenyl boronic acid instead of phenylboronic acid. 170 mg, 62%, brown liquid, $^{1}H$ NMR ($CDCl_3$, 400 MHz): δ 7.24-7.15 (m, 2H), 6.95-6.82 (m, 2H), 5.72-5.66 (m, 1H), 4.00-3.90 (m, 1H), 3.86-3.73 (m, 4H), 3.53-3.29 (m, 5H), 3.21-3.09 (m, 1H), 3.05-2.92 (m, 1H), 2.66-2.57 (m, 3H), 1.28-1.18 (m, 3H), 1.16-1.08 (m, 3H).

Example 8: Compounds 7 and 8 Via Chiral Resolution of I-8

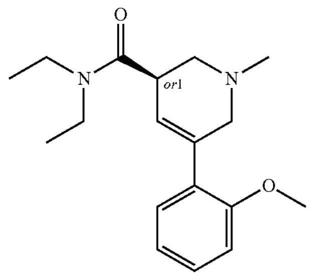

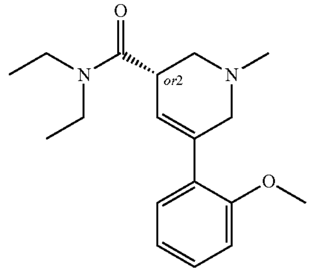

(R)—N,N-diethyl-5-(2-methoxyphenyl)-1-methyl-1,2,3,6-tetrahydropyridine-3-carboxamide and (S)—N,N-diethyl-5-(2-methoxyphenyl)-1-methyl-1,2,3,6-tetrahydropyridine-3-carboxamide Racemic I-8 (170 mg) was separated into its enantiomers by using SFC chiral HPLC (Chiralpak IG 250×30 5μ, 10%-50% gradient of 0.1% ammonia/$CH_3OH$ in $CO_2$, 80.0 mL/min). The first eluting enantiomer had a retention time of 10.30 minutes and the second eluting enantiomer had a retention time of 13.59 minutes.

Compound 7: 38 mg. brown solid; LC-MS: 99.4%, m/z=303.4 $[M+H]^+$; $^{1}H$ NMR ($CDCl_3$, 400 MHz): δ 7.24-

7.15 (m, 2H), 6.95-6.82 (m, 2H), 5.72-5.66 (m, 1H), 4.00-3.90 (m, 1H), 3.86-3.73 (m, 4H), 3.53-3.29 (m, 5H), 3.21-3.09 (m, 1H), 3.05-2.92 (m, 1H), 2.66-2.57 (m, 3H), 1.28-1.18 (m, 3H), 1.16-1.08 (m, 3H).

Compound 8: 41 mg; brown solid; LC-MS: 99.6%, m/z=303.1 $[M+H]^+$; $^1H$ NMR ($CDCl_3$, 400 MHz): δ 7.24-7.13 (m, 2H), 6.95-6.81 (m, 2H), 5.71-5.64 (m, 1H), 3.89 (br s, 1H), 3.84-3.77 (m, 3H), 3.72-3.63 (m, 1H), 3.51-3.31 (m, 4H), 3.26-3.15 (m, 1H), 3.11-3.01 (m, 1H), 2.91-2.80 (m, 1H), 2.53 (br s, 3H), 1.22 (br t, J=6.8 Hz, 3H), 1.12 (br t, J=6.8 Hz, 3H).

Example 9: Preparation of N,N-diethyl-5-(3-methoxyphenyl)-1-methyl-1,2,3,6-tetrahydropyridine-3-carboxamide (I-9)

I-9

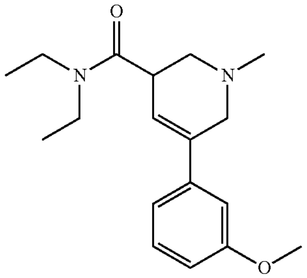

Intermediate I-9 was prepared as described for intermediate I-5 but using 3-methoxyphenyl boronic acid instead of phenylboronic acid. 180 mg, 66%, brown liquid, $^1H$ NMR ($CDCl_3$, 400 MHz): δ 7.25-7.15 (m, 2H), 6.93-6.82 (m, 2H), 5.96 (br s, 1H), 3.99-3.91 (m, 1H), 3.81 (br s, 4H), 3.50-3.31 (m, 6H), 3.19 (br s, 1H), 2.91 (br d, J=9.3 Hz, 1H), 2.67 (br s, 2H), 1.25 (br t, J=6.6 Hz, 3H), 1.14 (br t, J=6.6 Hz, 3H).

Example 10: Compounds 9 and 10 Via Chiral Resolution of I-9

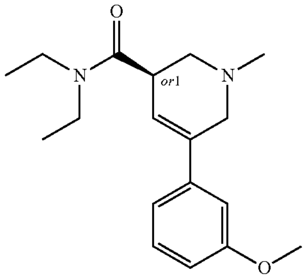

-continued

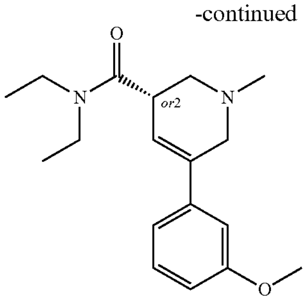

(R)—N,N-diethyl-5-(3-methoxyphenyl)-1-methyl-1,2,3,6-tetrahydropyridine-3-carboxamide and (S)—N,N-diethyl-5-(3-methoxyphenyl)-1-methyl-1,2,3,6-tetrahydropyridine-3-carboxamide Racemic I-9 (180 mg) was separated into its enantiomers by using SFC chiral HPLC (Chiralpak IG 250×30 5μ, 75%:25% gradient of 0.1% isopropyl amine/n-hexane and $CH_2Cl_2$ (50%):MeOH (50%), 25.0 mL/min). The first eluting enantiomer had a retention time of 5.90 minutes and the second eluting enantiomer had a retention time of 8.77 minutes.

Compound 9: 111 mg, brown solid, LC-MS: 99.6%, m/z=303.4 $[M+H]^+$; $^1H$ NMR ($CDCl_3$, 400 MHz): δ 7.25-7.15 (m, 2H), 6.93-6.82 (m, 2H), 5.96 (br s, 1H), 3.99-3.91 (m, 1H), 3.81 (br s, 4H), 3.50-3.31 (m, 6H), 3.19 (br s, 1H), 2.91 (br d, J=9.3 Hz, 1H), 2.67 (br s, 2H), 1.25 (br t, J=6.6 Hz, 3H), 1.14 (br t, J=6.6 Hz, 3H).

Compound 10: 36 mg brown solid; LC-MS: 99.7%, m/z=303.1 $[M+H]^+$; $^1H$ NMR ($CDCl_3$, 400 MHz): δ 7.25-7.16 (m, 2H), 6.99-6.87 (m, 2H), 5.97-5.92 (m, 1H), 3.84-3.74 (m, 4H), 3.57 (br d, J=15.7 Hz, 1H), 3.48-3.35 (m, 4H), 3.13 (br d, J=15.7 Hz, 1H), 3.00-2.90 (m, 1H), 2.65 (br t, J=10.5 Hz, 1H), 2.49 (br s, 3H), 1.28-1.21 (m, 3H), 1.14 (br t, J=6.6 Hz, 31H).

Example 11: Preparation of N,N-diethyl-5-(1H-indol-4-yl)-1-methyl-1,2,3,6-tetrahydropyridine-3-carboxamide (I-10)

I-10

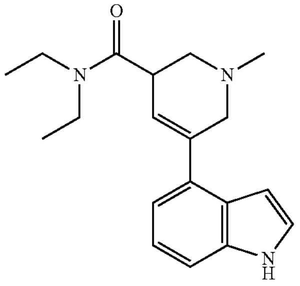

Intermediate I-10 was prepared as described for intermediate I-5 but using (1H-indol-4-yl)boronic acid instead of phenylboronic acid. 150 mg, 53%, colourless syrup, $^1H$ NMR (DMSO-$d_6$, 400 MHz): δ 11.16-11.05 (m, 1H), 7.43-7.17 (m, 2H), 7.03 (br s, 1H), 6.89 (br s, 1H), 6.60 (br s, 1H), 5.89 (br s, 1H), 3.87-3.70 (m, 1H), 3.62-3.33 (m, 4H), 3.24-2.86 (m, 3H), 2.45-2.26 (m, 4H), 1.16 (br s, 3H), 1.02 (br s, 3H).

Example 12: Compounds 11 and 12 Via Chiral Resolution of I-10

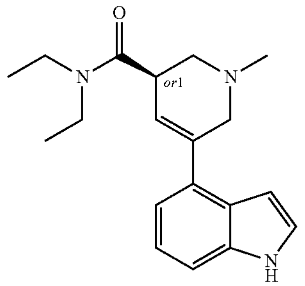

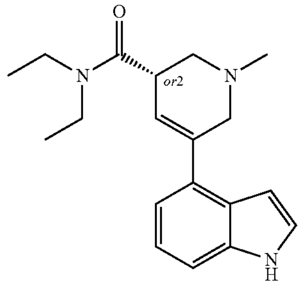

(R)—N,N-diethyl-5-(1H-indol-4-yl)-1-methyl-1,2,3,6-tetrahydropyridine-3-carboxamide and (S)—N,N-diethyl-5-(1H-indol-4-yl)-1-methyl-1,2,3,6-tetrahydropyridine-3-carboxamide Racemic I-10 (150 mg) was separated into its enantiomers by using SFC chiral HPLC (Chiralpak IC 250×30 5μ, 15%-50% gradient of 0.1% ammonia/$CH_3OH$ in $CO_2$, 80.0 mL/min). The first eluting enantiomer had a retention time of 13.43 minutes and the second eluting enantiomer had a retention time of 15.02 minutes.

Compound 11: 43 mg off-white solid, LC-MS: 99.5%, m/z=312.4 $[M+H]^+$; $^1H$ NMR (DMSO-$d_6$, 400 MHz): δ 11.16-11.05 (m, 1H), 7.43-7.17 (m, 2H), 7.03 (br s, 1H), 6.89 (br s, 1H), 6.60 (br s, 1H), 5.89 (br s, 1H), 3.87-3.70 (m, 1H), 3.62-3.33 (m, 4H), 3.24-2.86 (m, 3H), 2.45-2.26 (m, 4H), 1.16 (br s, 3H), 1.02 (br s, 3H).

Compound 12: 44 mg light brown solid, LC-MS: 98.4%, m/z=312.4 $[M+H]^+$; $^1H$ NMR (DMSO-$d_6$, 400 MHz): δ 11.17-11.05 (m, 1H), 7.36-7.25 (m, 2H), 7.03 (br t, J=6.6 Hz, 1H), 6.92-6.84 (m, 1H), 6.60 (br s, 1H), 5.94-5.82 (m, 1H), 3.78 (br s, 1H), 3.56-3.33 (m, 4H), 3.08-2.81 (m, 3H), 2.41-2.29 (m, 4H), 1.21-1.11 (m, 3H), 1.06-0.95 (m, 3H).

General Synthetic Scheme 2

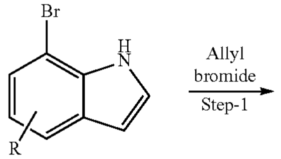

-continued

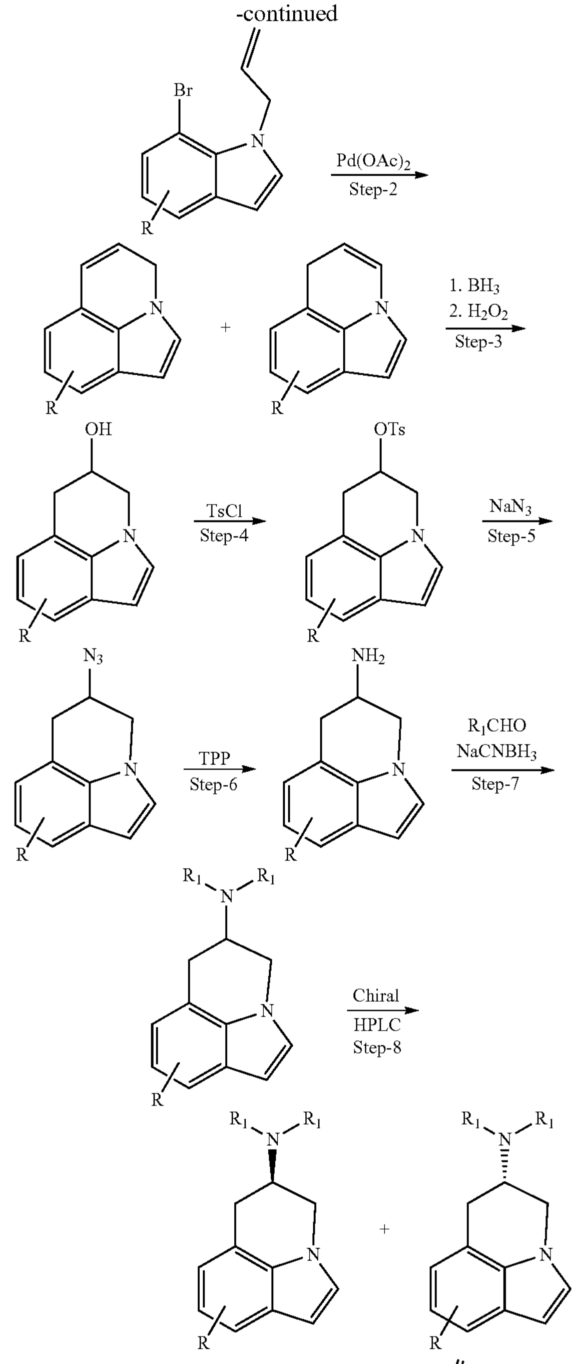

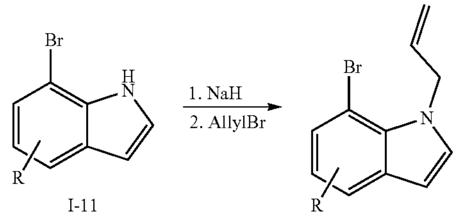

I-11

I-12

Step 2-1—Preparation of 1-allyl-7-bromo-1H-indole (I-12): To a solution of I-11 (8 g, 41.0 mmol, 1.0 eq) in DMF (80 mL) was added NaH (60% in mineral oil, 3.28 g, 82.0 mmol, 2.0 eq) at 0° C. The reaction mixture was stirred for 20 min and neat allyl bromide (7.44 g, 61.5 mmol, 1.5 eq)

was added. The reaction mixture was allowed to slowly warm to room temperature and stirred for additional 3 hours. The reaction was quenched carefully with ice cold water and extracted with ethyl acetate. The combined organic layers were washed with ice cold water and aqueous solution of NaCl. The combined organic layers were dried over anhydrous Na2SO4, solids were removed by filtration and the filtrate was concentrated in vacuo. The crude reaction residue was purified by silica gel chromatography in neat hexanes to provide I-12 (6 g, 61.9%, brown liquid). $^1$H NMR ($CDCl_3$, 400 MHz): δ 7.61-7.53 (m, 1H), 7.37 (br d, J=7.3 Hz, 1H), 7.10 (br d, J=2.9 Hz, 1H), 6.95 (br t, J=7.8 Hz, 1H), 6.54 (br d, J=2.9 Hz, 1H), 6.17-6.04 (m, 1H), 5.25-5.14 (m, 3H), 4.93-4.84 (m, 1H).

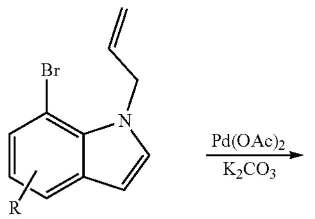

I-12

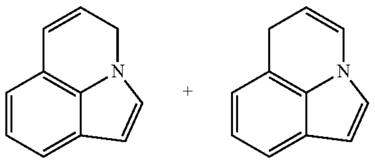

I-13

Step 2-2—Preparation of a mixture of 4H-pyrrolo[3,2,1-ij]quinoline and 6H-pyrrolo[3,2,1-ij]quinoline (I-13): To a stirred solution of I-12 (6 g, 25.4 mmole, 1.0 eq) in DMF (60 mL) was added $K_2CO_3$ (7.01 g, 50.8 mmol, 2.0 eq) at room temperature and the reaction was degassed under $N_2$ atmosphere for 20 minutes. To this mixture was added TBAI (4.69 g, 12.7 mmol, 0.5 eq) followed by $Pd(OAc)_2$ (570 mg, 2.54 mmol, 0.1 eq) and the reaction was stirred at 80° C. for 3 hours. The reaction mixture was diluted with water (60 mL) and filtered through a pad of Celite and the Celite pad was washed with ethyl acetate (3×50 mL). The combined organic layers were dried over anhydrous $Na_2SO_4$, solids were removed by filtration and the filtrate was concentrated in vacuo. The crude reaction residue was purified by silica gel chromatography (2 to 5% gradient of ethyl acetate in hexanes) to provide I-13 (3.1 g, 79%) as a mixture of regio-isomers.

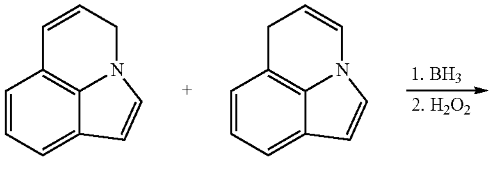

I-13

-continued

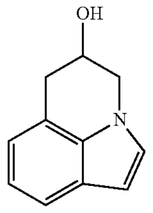

I-14

Preparation of 5,6-dihydro-4H-pyrrolo[3,2,1-ij]quinolin-5-ol (I-14): To a solution of I-13 (3.1 g, 20.1 mmol, 1.0 eq) in THF (31 mL) was added a solution of $BH_3$ (1M in THF, 40.2 mL, 40.2 mmol, 2.0 eq) at 0° C. and the reaction mixture was stirred under reflux for 2 hours. The reaction mixture was allowed to cool to room temperature, quenched with aqueous NaOH (3M in water, 46.5 mL) and a solution of $H_2O_2$ (30% in water, 31 mL) was added. The reaction mixture was stirred for additional 5 hours at the same temperature. The reaction mixture was quenched with ice cold aqueous solution of NaCl and extracted with ethyl acetate. The combined organic layers were dried over anhydrous $Na_2SO_4$, and concentrated in vacuo. The crude reaction residue was purified by silica gel chromatography (5% ethyl acetate in hexanes) to provide I-14 (1.8 g, 40% over two steps, brown liquid). $^1$H NMR ($CDCl_3$, 400 MHz): δ 7.54-7.43 (m, 1H), 7.13-7.03 (m, 2H), 7.01-6.90 (m, 1H), 6.50 (br d, J=2.9 Hz, 1H), 4.58 (br s, 1H), 4.31-4.22 (m, 1H), 4.20-4.10 (m, 1H), 3.33-3.21 (m, 1H), 3.09 (br dd, J=15.9, 4.6 Hz, 1H).

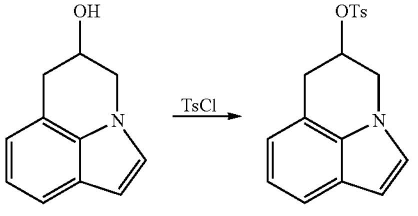

I-14 I-15

Preparation of 5,6-dihydro-4H-pyrrolo[3,2,1-ij]quinolin-5-yl 4-methylbenzenesulfonate (I-15): To a solution of I-14 (1.3 g, 7.5 mmol, 1.0 eq) in dichloromethane (13 mL) was added triethylamine (2.64 mL, 18.7 mmol, 2.5 eq) at 0° C. and the reaction mixture was stirred for 10 minutes. To the reaction mixture was added TsCl (2.86 g, 15.0 mmol, 2.0 eq) followed by DMAP (91 mg, 0.7 mmol, 0.1 eq), the reaction mixture was allowed to slowly warm to room temperature and stirred for additional 6 hours. The reaction mixture was quenched with ice cold water and extracted with ethyl acetate. The combined organic layers were washed with an aqueous solution of NaCl, the combined organic layers were dried over anhydrous $Na_2SO_4$, solids were removed by filtration and the filtrate was concentrated. The crude reaction residue was purified by silica gel chromatography (5% ethyl acetate in hexanes) to provide I-15 (1.3 g, 53%). $^1$H NMR ($CDCl_3$, 400 MHz): δ 7.76 (d, J=8.3 Hz, 2H), 7.39-7.31 (m, 3H), 7.13-7.03 (m, 2H), 7.01-6.90 (m, 1H), 6.50 (br d, J=2.9 Hz, 1H), 5.22 (quin, J=4.9 Hz, 1H), 4.31-4.22 (m, 1H), 4.20-4.10 (m, 1H), 3.33-3.21 (m, 1H), 3.09 (br dd, J=15.9, 4.6 Hz, 1H), 2.46 (s, 3H).

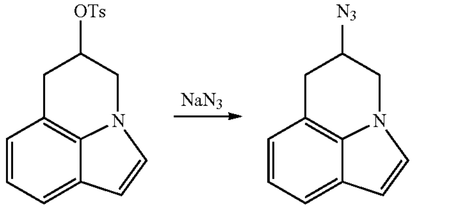

I-15 I-16

Preparation of 5-azido-5,6-dihydro-4H-pyrrolo[3,2,1-ij]quinoline (I-16): To a solution of I-15 (1.3 g, 3.9 mmole, 1.0 eq) in DMF (13 mL) was added $NaN_3$ (387 mg, 5.9 mmol, 1.5 eq) at 0° C., the reaction mixture was allowed to slowly warm to room temperature and stirred at 65° C. for additional 2 hours. The reaction mixture was allowed to coo to room temperature, quenched with ice cold water and extracted with diethyl ether. The combined organic layers were washed with ice cold water followed by an aqueous solution of NaCl. The organic layers were dried over anhydrous $Na_2SO_4$ and concentrated in vacuo. The crude reaction residue I-16 (800 mg) was used in the next step without further purification.

Example 13: Preparation of 5,6-dihydro-4H-pyrrolo[3,2,1-ij]quinolin-5-amine (13)

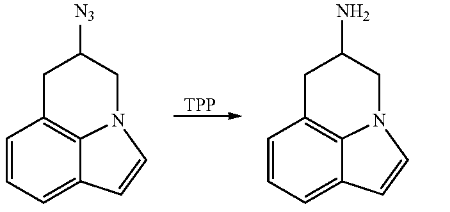

I-16 13

To a solution of crude I-16 (800 mg, 4.0 mmol, 1.0 eq) in a mixture of THF (16 mL) and $H_2O$ (8 mL) was added TPP (1.58 g, 6.06 mmol, 1.5 eq) at 0° C., the reaction mixture was allowed to slowly warm to room temperature and stirred at 80° C. for additional 2 hours. The reaction mixture was allowed to cool to room temperature, quenched with ice cold water and extracted with ethyl acetate. The combined organic layers were washed with an aqueous solution of NaCl, the organic layer was dried over anhydrous $Na_2SO_4$ and concentrated in vacuo. The crude reaction residue was purified by silica gel chromatography (5% MeOH in $CH_2Cl_2$) to obtain Compound 13 (350 mg, 51% over two steps, brown liquid). LC-MS: 93.1%, m/z=172.9 $[M+H]^+$; $^1H$ NMR ($CDCl_3$, 400 MHz): δ 7.47 (br d, J=7.3 Hz, 1H), 7.12-7.01 (m, 2H), 7.00-6.91 (m, 1H), 6.52-6.45 (m, 1H), 4.33-4.23 (m, 1H), 3.97-3.88 (m, 1H), 3.74-3.65 (m, 1H), 3.28-3.18 (m, 1H), 2.93-2.84 (m, 1H).

Example 14: Preparation of N,N-dimethyl-5,6-dihydro-4H-pyrrolo[3,2,1-ij]quinolin-5-amine (I-17)

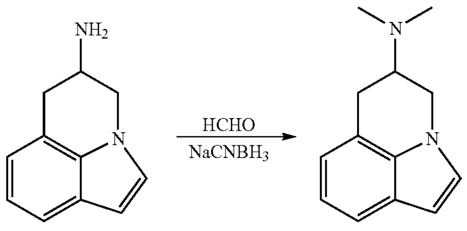

13 I-17

To a solution of Compound 13 (120 mg, 0.69 mmol, 1.0 eq) in a mixture of MeOH (0.6 mL) and THF (0.6 mL) was added a solution of formaldehyde (37% in water, 0.17 mL, 2.09 mmol, 3.0 eq.) at room temperature and the reaction mixture was stirred for 30 minutes. The reaction mixture was cooled to 0° C. and $NaCNBH_3$ (87 mg, 1.39 mmol, 2.0 eq) was added portion-wise. The resulting reaction mixture was allowed to slowly warm to room temperature and stirred for additional 16 hours. Volatiles were removed in vacuo, the crude reaction residue was washed with water and extracted with ethyl acetate. The combined organic layers were washed with an aqueous solution of NaCl, the organic layer was dried over anhydrous $Na_2SO_4$ and concentrated in vacuo. The crude reaction residue was purified by silica gel chromatography (1% MeOH in $CH_2Cl_2$) to obtain I-17 (100 mg, 72%).

Example 15: Compounds 14 and 15 Via Chiral Resolution of I-17

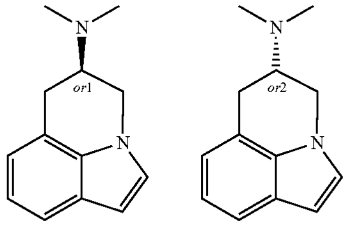

(R)—N,N-dimethyl-5,6-dihydro-4H-pyrrolo[3,2,1-ij]quinolin-5-amine and (S)—N,N-dimethyl-5,6-dihydro-4H-pyrrolo[3,2,1-ij]quinolin-5-amine Racemic I-17 (100 mg) was separated into its enantiomers by using SFC chiral HPLC (Phenomenex Cellulose-4 250×30 5μ, isocratic 20% isopropyl amine in 0.1% TFA/n-hexane, 28.0 mL/min). The first eluting enantiomer had a retention time of 17.30 minutes and the second eluting enantiomer had a retention time of 20.63 minutes.

Compound 14: 23 mg, brown liquid, LC-MS: 97.8%, m/z=201.0 $[M+H]^+$; $^1H$ NMR ($CDCl_3$, 400 MHz): δ 7.48-7.44 (m, 1H), 7.13-6.99 (m, 2H), 6.99-6.89 (m, 1H), 6.47 (d, J=2.9 Hz, 1H), 4.46-4.29 (m, 1H), 4.05 (dd, J=11.2, 9.8 Hz, 1H), 3.27-3.13 (m, 2H), 3.13-2.98 (m, 1H), 2.50-2.48 (m, 6H).

Compound 15: 14 mg, brown liquid, LC-MS: 84.3%, m/z=200.9 $[M+H]^+$; $^1H$ NMR ($CDCl_3$, 400 MHz): δ 7.47-

7.43 (m, 1H), 7.10-7.06 (m, 1H), 7.06-7.01 (m, 1H), 6.97-6.93 (m, 1H), 6.49-6.45 (m, 1H), 4.41-4.35 (m, 1H), 4.08-3.99 (m, 1H), 3.24-3.14 (m, 3H), 2.50-2.48 (m, 6H).

Example 16: Preparation of N,N-diethyl-5,6-dihydro-4H-pyrrolo[3,2,1-]quinolin-5-amine (16)

16

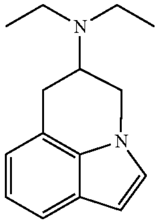

Compound 16 was prepared as described for intermediate I-17 but using acetaldehyde instead of formaldehyde. 70 mg, off-white solid, LC-MS: 98.8%, m/z=229.4 $[M+H]^+$; $^1H$ NMR ($CDCl_3$, 400 MHz): δ 7.43 (br d, J=7.8 Hz, 1H), 7.10-6.97 (m, 2H), 6.95-6.88 (m, 1H), 6.49-6.41 (m, 1H), 4.31-4.22 (m, 1H), 4.06-3.93 (m, 1H), 3.58-3.46 (m, 1H), 3.13-3.02 (m, 2H), 2.77-2.66 (m, 4H), 1.19-1.04 (m, 6H).

Example 17: Preparation of 8-fluoro-5,6-dihydro-4H-pyrrolo[3,2,1-ij]quinolin-5-amine (17)

17

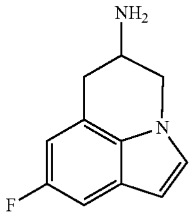

Compound 17 was prepared as described for Compound 13 but using 5-fluoro-1H-indole instead of 1H-indole. 50 mg, LC-MS: 97.6%, m/z=191.1 $[M+H]^+$; $^1H$ NMR (DMSO-$d_6$, 400 MHz): δ 7.36 (d, J=2.9 Hz, 1H), 7.07 (dd, J=10.5, 2.3 Hz, 1H), 6.73 (td, J=9.8, 1.1 Hz, 1H), 6.35 (d, J=3.0 Hz, 1H), 4.23 (ddd, J=11.8, 4.2, 0.9 Hz, 1H), 3.74 (dd, J=11.9, 8.3 Hz, 1H), 3.39 (td, J=8.6, 4.3 Hz, 1H), 3.06 (dd, J=15.9, 4.2 Hz, 1H), 2.74 (dd, J=15.9, 8.9 Hz, 1H), 1.86 (br s, 2H).

Example 18: Preparation of 8-fluoro-N,N-dimethyl-5,6-dihydro-4H-pyrrolo[3,2,1-ij]quinolin-5-amine (18)

18

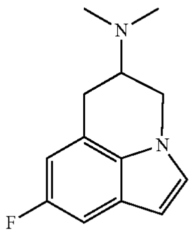

Compound 18 was prepared as described for intermediate I-17 but using Compound 17 instead of Compound 13. 15 mg, 26%, colourless gum, LC-MS: 99.0%, m/z=219.1 $[M+H]^+$; $^1H$ NMR (DMSO-$d_6$, 400 MHz): δ 7.36 (d, J=2.9 Hz, 1H), 7.07 (dd, J=10.5, 2.2 Hz, 1H), 6.75 (dd, J=9.9, 2.1 Hz, 1H), 6.34 (d, J=2.9 Hz, 1H), 4.37-4.29 (m, 1H), 4.11-3.98 (m, 1H), 3.12-2.95 (m, 3H), 2.32 (s, 6H).

Example 19: Preparation of 7-fluoro-5,6-dihydro-4H-pyrrolo[3,2,1-ij]quinolin-5-amine (19)

19

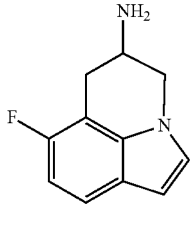

Compound 19 was prepared as described for intermediate Compound 13 but using 6-fluoro-1H-indole instead of 1H-indole. 200 mg, colour-less gum, LC-MS: 99.01%, m/z=191.1 $[M+H]^+$; $^1H$ NMR (DMSO-$d_6$, 400 MHz): δ 7.34-7.26 (m, 2H), 6.79 (dd, J=10.3, 8.6 Hz, 1H), 6.36 (d, J=3.0 Hz, 1H), 4.25-4.16 (m, 1H), 3.73 (dd, J=11.9, 8.1 Hz, 1H), 3.39 (tt, J=8.5, 4.3 Hz, 1H), 3.09 (dd, J=16.0, 4.3 Hz, 1H), 2.70-2.62 (m, 1H), 2.01-1.77 (m, 2H).

Example 20: Preparation of 7-fluoro-N,N-dimethyl-5,6-dihydro-4H-pyrrolo[3,2,1-ij]quinolin-5-amine (20)

20

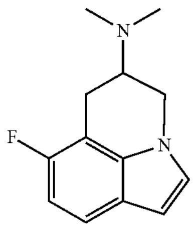

Compound 20 was prepared as described for intermediate I-17 but using Compound 19 instead of Compound 13. 20 mg, LC-MS: 97.2%, m/z=218.1 $[M+H]^+$; $^1H$ NMR (DMSO-$d_6$, 400 MHz): δ 7.37-7.34 (m, 1H), 7.07 (dd, J=10.5, 2.2 Hz, 1H), 6.75 (dd, J=9.9, 2.1 Hz, 1H), 6.34 (d, J=2.9 Hz, 1H), 4.37-4.29 (m, 1H), 4.07 (s, 1H), 3.12-2.92 (m, 3H), 2.32 (s, 6H).

Example 21: Preparation of 8-chloro-5,6-dihydro-4H-pyrrolo[3,2,1-ij]quinolin-5-amine (21)

21

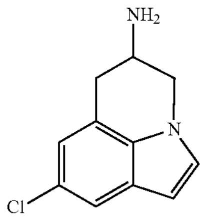

Compound 21 was prepared as described for Compound 13 but using 5-chloro-1H-indole instead of 1H-indole. 20 mg; colour-less liquid, LC-MS: 95.88%, m/z=207.1 $[M+H]^+$; $^1H$ NMR ($CDCl_3$, 400 MHz): δ 7.45-7.40 (m, 1H), 7.08 (d, J=3.1 Hz, 1H), 6.93 (s, 1H), 6.40 (d, J=3.0 Hz, 1H), 4.25 (dd, J=11.9, 3.3 Hz, 1H), 3.89 (dd, J=11.9, 6.9 Hz, 1H), 3.67 (br t, J=3.8 Hz, 1H), 3.18 (dd, J=15.9, 3.9 Hz, 1H), 2.84 (dd, J=15.9, 7.4 Hz, 1H).

Example 22: Preparation of 8-chloro-N,N-dimethyl-5,6-dihydro-4H-pyrrolo[3,2,1-ij]quinolin-5-amine (22)

22

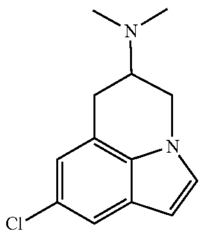

Compound 22 was prepared as described for intermediate I-17 but using Compound 21 instead of Compound 13. 7 mg, colour-less gum, LC-MS: 90.2%, m/z=235.1 $[M+H]^+$; $^1H$ NMR (DMSO-$d_6$, 400 MHz): δ 7.38-7.35 (m, 2H), 6.91-6.88 (m, 1H), 6.36-6.33 (m, 1H), 4.36-4.30 (m, 1H), 4.08-4.01 (m, 1H), 3.12-2.97 (m, 3H), 2.31 (s, 6H).

Example 23: Preparation of 7-chloro-5,6-dihydro-4H-pyrrolo[3,2,1-ij]quinolin-5-amine (23)

23

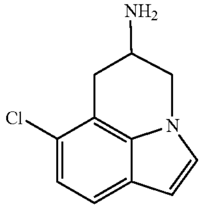

Compound 23 was prepared as described for Compound 13 but using 6-chloro-1H-indole instead of 1H-indole. 50 mg; pale-yellow semi-solid, LC-MS: 98.78%, m/z=207.0 $[M+H]^+$; $^1H$ NMR (DMSO-$d_6$, 400 MHz): δ 7.34 (dd, J=5.7, 2.7 Hz, 2H), 6.96 (d, J=8.4 Hz, 1H), 6.38 (d, J=3.0 Hz, 1H), 4.25-4.20 (m, 1H), 3.74 (s, 1H), 3.45-3.38 (m, 1H), 3.16-3.09 (m, 1H), 2.71-2.64 (m, 1H), 2.04-1.91 (m, 2H).

Example 24: Preparation of 7-chloro-N,N-dimethyl-5,6-dihydro-4H-pyrrolo[3,2,1-ij]quinolin-5-amine (24)

24

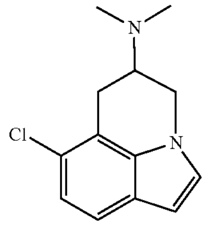

Compound 24 was prepared as described for intermediate I-17 but using Compound 23 instead of Compound 13. 20 mg, LC-MS: 97.8%, m/z=234.01 $[M+H]^+$; $^1H$ NMR (DMSO-$d_6$, 400 MHz): δ 7.42-7.27 (m, 2H), 6.97 (d, J=8.4 Hz, 1H), 6.38 (d, J=2.9 Hz, 1H), 4.42-4.22 (m, 1H), 4.11-3.96 (m, 1H), 3.14-3.03 (m, 2H), 2.98-2.90 (m, 1H), 2.33 (s, 6H).

Example 25: Preparation of 8-methoxy-5,6-dihydro-4H-pyrrolo[3,2,1-ij]quinolin-5-amine (25)

25

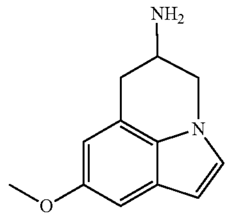

Compound 25 was prepared as described for Compound 13 but using 5-methoxy-1H-indole instead of 1H-indole. 20 mg, pale-pink solid, LC-MS: 97.44%, m/z=203.1 $[M+H]^+$; $^1H$ NMR (DMSO-$d_6$, 400 MHz): δ 7.22 (d, J=2.9 Hz, 1H), 6.82 (d, J=2.0 Hz, 1H), 6.52 (s, 1H), 6.25 (d, J=2.8 Hz, 1H), 4.22-4.17 (m, 1H), 3.71 (s, 4H), 3.39-3.36 (m, 1H), 3.03-2.97 (m, 1H), 2.73-2.65 (m, 2H), 1.90 (s, 1H).

Example 26: Preparation of 8-methoxy-N,N-dimethyl-5,6-dihydro-4H-pyrrolo[3,2,1-ij]quinolin-5-amine (26)

26

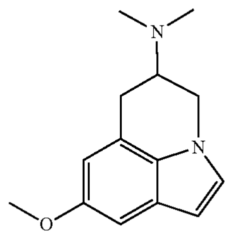

Compound 26 was prepared as described for intermediate I-17 but using Compound 25 instead of Compound 13. 20 mg, colour-less gum, LC-MS: 98.3%, m/z=231.1 $[M+H]^+$; $^1H$ NMR (DMSO-$d_6$, 400 MHz): δ 7.24-7.20 (m, 1H), 6.83-6.80 (m, 1H), 6.55 (s, 1H), 6.26-6.24 (m, 1H), 4.33-4.27 (m, 1H), 4.01-3.95 (m, 1H), 3.71 (s, 3H), 3.05-2.90 (m, 3H), 2.32 (s, 6H).

General Synthetic Scheme 3

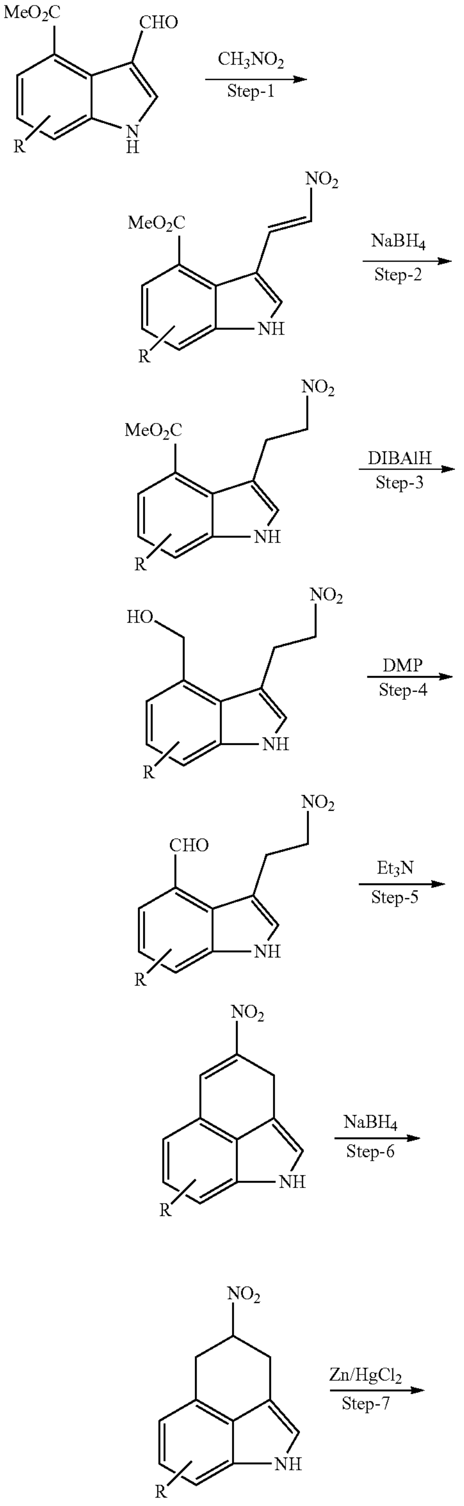

-continued

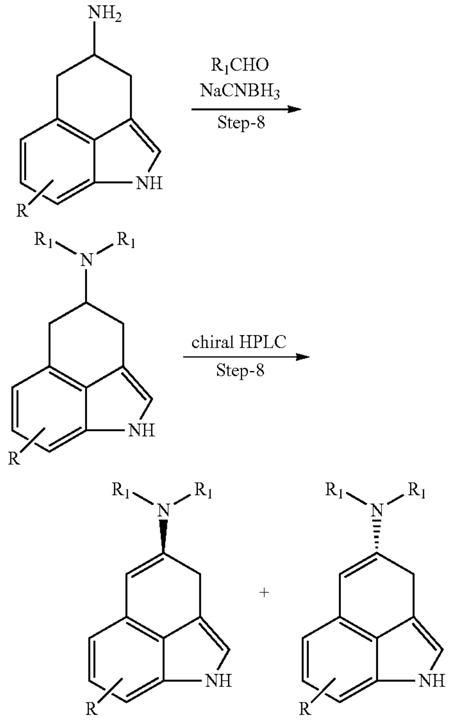

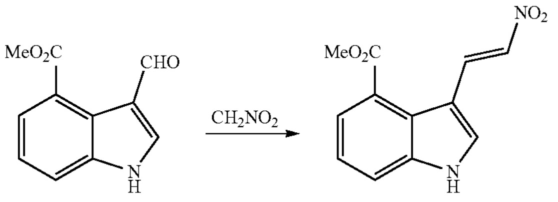

I-18 I-19

Preparation of methyl (E)-3-(2-nitrovinyl)-1H-indole-4-carboxylate (I-19): To a stirred solution of I-18 (1.7 g, 8.37 mmol, 1.0 eq) in nitromethane (25.5 ml, 15 vol) was added $NH_4OAc$ (644 mg, 8.37 mmol, 1.0 eq) at room temperature and the resulting mixture was stirred at 90° C. for 5 hours. Volatiles were evaporated under reduced pressure, crystals were collected by filtration, washed with a mixture of $MeOH/H_2O$ (1:1) to obtain I-19 (1.6 g, 77%, yellow solid, $^1H$ NMR (DMSO-$d_6$, 400 MHz): δ 12.5 (br s, 1H), 9.21 (d, J=15.2 Hz, 1H), 8.56 (s, 1H), 8.01 (d, J=15.2 Hz, 1H), 7.88-7.77 (m, 1H), 7.34 (t, J=7.2 Hz, 1H), 3.95 (s, 3H).

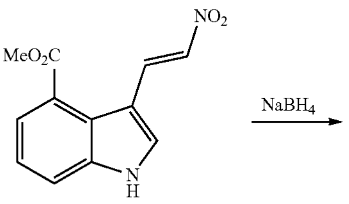

I-19

-continued

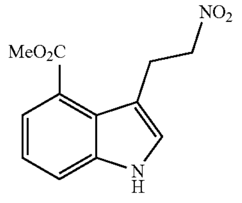

I-20

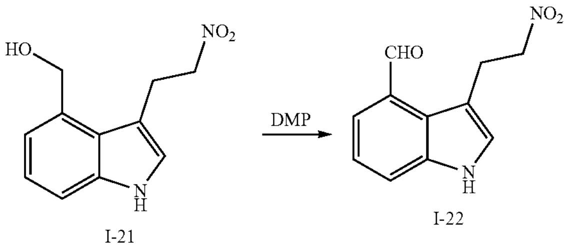

I-21 I-22

Preparation of methyl 3-(2-nitroethyl)-1H-indole-4-carboxylate (I-20): To a solution of I-19 (1.6 g, 6.5 mmol, 1.0 eq) in methanol (32 ml) was added portion-wise $NaBH_4$ (1.96 g, 52.03 mmol, 8.0 eq) at 0° C., the reaction mixture was allowed to warm to room temperature and stirred for 30 minutes. The reaction was quenched by adding water (16 ml), pH was adjusted to 5 by adding 0.6% HCl (~25-30 ml) and the reaction mixture was extracted with dichloromethane. The combined organic layers were washed with an aqueous solution of NaCl, the organic layer was dried over anhydrous $Na_2SO_4$, solids were removed by filtration and the filtrate was concentrated in vacuo. The crude reaction residue was purified by silica gel chromatography (10% ethyl acetate in hexane) to obtain I-20 (1.2 g, 75%, yellow solid, $^1H$ NMR (DMSO-$d_6$, 400 MHz): δ 11.43 (br s, 1H), 7.61 (br dd, J=9.2, 9.0 Hz, 1H), 7.40-7.36 (m, 1H), 7.17 (t, J=7.8 Hz, 1H), 4.74 (t, J=7.0 Hz, 2H), 3.88 (s, 3H), 3.49 (t, J=6.9 Hz, 2H).

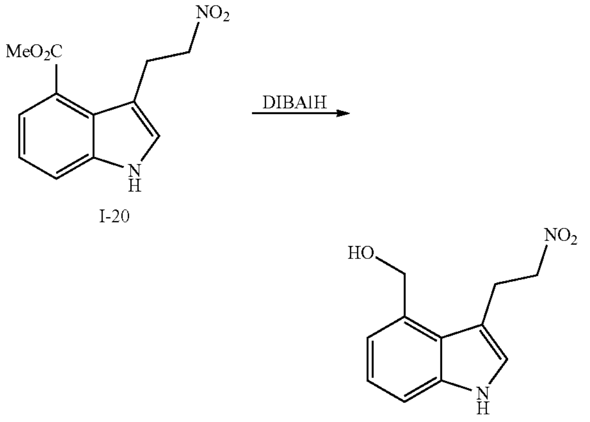

I-20

I-21

Preparation of (3-(2-nitroethyl)-1H-indol-4-yl)methanol (I-21): To a solution of I-20 (1.2 g, 4.83 mmol, 1.0 eq) in THF (12 ml) was added DIBAL (9.67 ml, 9.67 mmol, 2.0 eq) at −40° C., the reaction mixture was allowed to warm to room temperature and stirred for 1 hour. To the reaction mixture was added a mixture of MeOH:$H_2O$ (2:1, 12 ml) and the reaction mixture was heated under reflux for additional 1 hour. The reaction mixture was allowed to cool to room temperature and volatiles were evaporated under reduced pressure. The crude reaction residue was purified by silica gel chromatography (10% ethyl acetate in hexane) to obtain I-21 (850 mg, 80%, yellow solid, $^1H$ NMR (DMSO-$d_6$, 400 MHz): δ 11.00-10.95 (m, 1H), 7.29-7.25 (m, 1H), 7.14-7.12 (m, 1H), 7.04-6.99 (m, 1H), 6.97-6.93 (m, 1H), 5.13-5.09 (m, 1H), 4.89-4.84 (m, 2H), 4.82-4.78 (m, 2H), 3.57-3.51 (m, 2H).

Preparation of 3-(2-nitroethyl)-1H-indole-4-carbaldehyde (I-22): To a solution of I-21 (850 mg, 3.8 mmol, 1.0 eq) in dichloromethane (8.5 ml) was added DMP (3.27 g, 7.7 mmol, 2.0 eq) at 0° C., the reaction mixture was allowed to warm to room temperature and stirred for 3 hours. The reaction mixture was quenched with saturated aqueous $NH_4Cl$ solution and extracted with dichloromethane. The combined organic layer were washed with an aqueous solution of NaCl, the combined organic layers were dried over anhydrous Na2$SO_4$, solids were removed by filtration and the filtrate was concentrated in vacuo to obtain I-22 (550 mg, 65%, yellow solid, $^1H$ NMR (DMSO-$d_6$, 400 MHz): δ 11.60-11.54 (m, 1H), 10.16-10.13 (m, 1H), 7.76-7.68 (m, 2H), 7.45-7.43 (m, 1H), 7.34-7.29 (m, 1H), 4.77-4.73 (m, 2H), 3.67-3.62 (m, 2H).

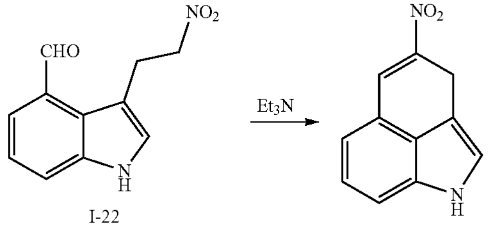

I-22 I-23

Preparation of 4-nitro-1,3-dihydrobenzo[cd]indole (I-23): A solution of I-22 (550 mg, 2.52 mmol, 1.0 eq) in a mixture of $Et_3N$:MeOH (1:4, 11 ml) was heated under reflux for 1 hour. Volatiles were evaporated under reduced pressure, water (11 ml) was added to the residue and pH was adjusted to 4 by adding 0.6% HCl (~7-10 ml) and the reaction mixture was extracted with dichloromethane. The combined organic layers were washed with an aqueous solution of NaCl, the organic layer was dried over anhydrous $Na_2SO_4$, solids were removed by filtration and the filtrate was concentrated in vacuo. The crude reaction residue was purified by silica gel chromatography (10% ethyl acetate in hexanes) to obtain I-23 (300 mg, 60%, red solid, $^1H$ NMR (DMSO-$d_6$, 400 MHz): δ 11.13 (br s, 1H), 8.19-8.17 (m, 1H), 7.36-7.32 (m, 1H), 7.22-7.18 (m, 1H), 7.14-7.03 (m, 2H), 4.28 (s, 2H).

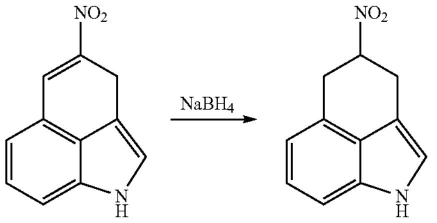

I-23 I-24

Preparation of 4-nitro-1,3,4,5-tetrahydrobenzo[cd]indole (I-24): To a solution of I-23 (300 mg, 1.5 mmol, 1.0 eq) in MeOH (6 ml) was added portion-wise $NaBH_4$ (453 mg, 12.0 mmol, 8.0 eq) at 0° C., the reaction mixture was allowed to warm to room temperature and stirred for 30 minutes. The reaction was quenched by adding water (3 ml), pH was adjusted to 5 by adding 0.6% HCl (~7 ml) and the reaction mixture was extracted with dichloromethane. The combined organic layers were washed with an aqueous solution of NaCl, the organic layer was dried over anhydrous $Na_2SO_4$, solids were removed by filtration and the filtrate was concentrated in vacuo. The crude reaction residue was purified by silica gel chromatography (10% ethyl acetate in hexanes) to obtain I-24 (150 mg, 50%, red solid, $^1$H NMR (DMSO-$d_6$, 400 MHz): δ 10.78 (br s, 1H), 7.17-7.14 (m, 1H), 7.14-6.99 (m, 2H), 6.80 (d, J=7.0 Hz, 1H), 5.30-5.23 (m, 1H), 3.60-3.41 (m, 4H).

Example 27: Preparation of 1,3,4,5-tetrahydrobenzo[cd]indol-4-amine (27)

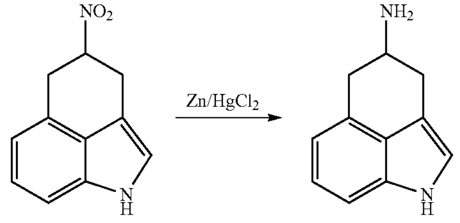

I-24    27

A solution of HCl (6% in water, 3.0 mL) was added to a mixture of Zn powder (2.42 g, 37.1 mmol, 50 eq) and $HgCl_2$ (221 mg, 0.81 mmol, 1.1 eq) and the reaction mixture was stirred for 5 min. Liquid was removed by decantation and to the solid residue was added a solution of I-24 (150 mg, 0.74 mmol, 1.0 eq) in methanol (1.5 ml) and HCl (6% in water, 1.5 ml). The reaction mixture was heated under reflux for 3 hours. Solids were removed by filtration and a solution of NaOH (8% in water, ~5 ml) was added to make the solution alkaline. The crude reaction mixture was extracted with dichloromethane, the combined organic layers were washed with an aqueous solution of NaCl, the organic layer was dried over anhydrous $Na_2SO_4$, solids were removed by filtration and the filtrate was concentrated in vacuo. The crude reaction residue was purified by silica gel chromatography (10% ethyl acetate in hexanes) to obtain Compound 27 (60 mg, 48%, pale-brown semi-solid, LC-MS: 91.7%, m/z=173.0 $[M+H]^+$; $^1$H NMR (DMSO-$d_6$, 400 MHz): δ 10.58-10.49 (m, 1H), 7.07 (br d, J=7.3 Hz, 1H), 7.01-6.81 (m, 2H), 6.66 (br d, J=6.4 Hz, 1H), 3.24-3.13 (m, 2H), 2.95 (br d, J=13.2 Hz, 2H), 2.72-2.58 (m, 1H).

Example 28: Preparation of N,N-dimethyl-1,3,4,5-tetrahydrobenzo[cd]indol-4-amine

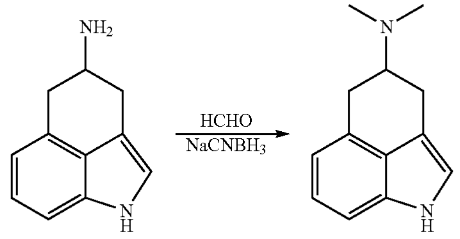

27    28

To a stirred solution of crude Compound 27 (350 mg, 2.03 mmol, 1.0 eq) in a mixture of MeOH:THF (1:1, 3.5 ml) was added a solution of formaldehyde (37% in water, 0.49 ml, 6.10 mmol, 3.0 eq) at room temperature and the reaction mixture stirred for 30 minutes. The reaction mixture was allowed to cool to 0° C. and $NaCNBH_3$ (255 mg, 4.06 mmol, 2.0 eq) was added portion-wise. The resulting reaction mixture was allowed to slowly warm to room temperature and stirred for 16 hours. Volatiles were evaporated under reduced pressure and the crude reaction residue was washed with water and extracted with ethyl acetate. The combined organic layers were washed with an aqueous solution of NaCl, the organic layer was dried over anhydrous $Na_2SO_4$, solids were removed filtration and the filtrate was concentrated in vacuo. The crude reaction residue was purified by silica gel chromatography (2% MeOH in $CH_2Cl_2$) to obtain Compound 28 (16 mg, 4%, pale-brown semi-solid, LC-MS: 98.1%, m/z=201.2 $[M+H]^+$; $^1$H NMR (DMSO-$d_6$, 400 MHz): δ 10.54 (br s, 1H), 7.07 (d, J=8.2 Hz, 1H), 6.98-6.92 (m, 2H), 6.69 (d, J=7.0 Hz, 1H), 3.05-2.91 (m, 2H), 2.91-2.82 (m, 2H), 2.75 (s, 1H), 2.35 (s, 6H).

Example 29: Preparation of N,N-diethyl-1,3,4,5-tetrahydrobenzo[cd]indol-4-amine (29)

29

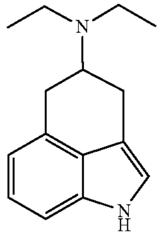

Compound 29 was prepared as described for Compound 28 but using acetaldehyde instead of formaldehyde. 110 mg, pale pink semi solid, LC-MS: 88.7%, m/z=229.1 $[M+H]^+$; $^1$H NMR (DMSO-$d_6$, 400 MHz): δ 10.53 (br s, 1H), 7.10-7.04 (m, 1H), 6.98-6.91 (m, 2H), 6.68 (br d, J=6.8 Hz, 1H), 3.19-3.01 (m, 2H), 2.96-2.83 (m, 3H), 2.71-2.59 (m, 4H), 1.02 (br t, J=6.6 Hz, 6H).

Example 30: Compounds 30 and 31 Via Chiral Resolution of Compound 29

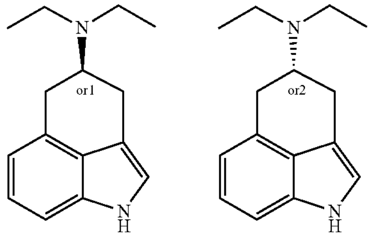 [SMILES: CCN(CC)[C@@H]1Cc2cccc3[nH]cc(c23)C1 ; CCN(CC)[C@H]1Cc2cccc3[nH]cc(c23)C1]

(R)—N,N-diethyl-1,3,4,5-tetrahydrobenzo[cd]indol-4-amine and (S)—N,N-diethyl-1,3,4,5-tetrahydrobenzo[cd]indol-4-amine Racemic Compound 29 (80 mg) was separated into its enantiomers by using SFC chiral HPLC (Chiralpak IG 250×30 5μ, 90%:10% gradient of 0.1% DEA in N-Hexane and $CH_2Cl_2$ (50%):MeOH (50%), 35.0 mL/min). The first eluting enantiomer had a retention time of 5.57 minutes and the second eluting enantiomer had a retention time of 7.54 minutes.

Compound 30: 15 mg, brown semi solid LC-MS: 99.08%, m/z=229.1 $[M+H]^+$; $^1H$ NMR (DMSO-$d_6$, 400 MHz): δ 10.53 (br s, 1H), 7.09-7.04 (m, 1H), 6.97-6.90 (m, 2H), 6.68 (d, J=7.0 Hz, 1H), 3.19-3.08 (m, 1H), 2.97-2.79 (m, 3H), 2.78-2.68 (m, 1H), 2.66-2.58 (m, 4H), 1.02 (t, J=7.1 Hz, 6H).

Compound 31: 15 mg, brown semi solid, LC-MS: 98.4%, m/z=229.1 $[M+H]^+$; $^1H$ NMR (DMSO-$d_6$, 400 MHz): δ 10.55-10.50 (m, 1H), 7.08-7.05 (m, 1H), 6.96-6.90 (m, 2H), 6.67 (d, J=7.0 Hz, 1H), 3.17-3.08 (m, 1H), 2.93-2.83 (m, 3H), 2.77-2.71 (m, 1H), 2.67-2.60 (m, 4H), 1.04-0.99 (m, 6H).

Example 31: Serotonin Assays

Serotonin 5-HT2A In Vitro Radioligand Binding Competition Assay. The 5-HT2A radioligand binding competition assay was performed at Epics Therapeutics S.A. (Belgium, FAST-0505B) using conventional methods. Briefly, competition binding is performed in duplicate in the wells of a 96 well plate (Master Block, Greiner, 786201) containing binding buffer (optimized for each receptor), membrane extracts (amount of protein/well optimized for each receptor), radiotracer [$^3$H]-DOI (final concentration optimized for each receptor) and test compound. Nonspecific binding is determined by co-incubation with 200-fold excess of cold competitor. The samples are incubated in a final volume of 0.1 ml at a temperature and for a duration optimized for each receptor and then filtered over filter plates. Filters are washed six times with 0.5 ml of ice-cold washing buffer (optimized for each receptor) and 50 μl of Microscint 20 (Packard) are added in each well. The plates are incubated 15 min on an orbital shaker and then counted with a TopCount™ for 1 min/well.

Serotonin 5-HT2A In Vitro Cellular IPOne Agonism Assay. The 5-HT2A IPOne HTRF assay was performed at Epics Therapeutics S.A. (Belgium, FAST-0505I) using conventional methods. Briefly, CHO-K1 cells expressing human recombinant 5-HT2A receptor grown to mid-log phase in culture media without antibiotics were detached with PBS-EDTA, centrifuged, and resuspended in medium without antibiotics buffer. 20,000 cells are distributed in a 96 well plate and incubated overnight at 37° C. with 5% $CO_2$. For agonist testing, the medium is removed and 20 μl of assay buffer plus 20 μl of test compound or reference agonist are added in each well. The plate is incubated for 60 min. at 37° C. with 5% $CO_2$.

After addition of the lysis buffer containing IP1-d2 and anti-IP1 cryptate detection reagents, plates are incubated 1-hour at room temperature, and fluorescence ratios are measured according to the manufacturer specification, with the HTRF kit.

Serotonin 5-HT2C In Vitro Radioligand Binding Competition Assay. The 5-HT2C edited (accession number AAF35842.1) radioligand binding competition assay was performed at Epics Therapeutics S.A. (Belgium, FAST-0507B) using conventional methods. Briefly, competition binding is performed in duplicate in the wells of a 96 well plate (Master Block, Greiner, 786201) containing binding buffer (optimized for each receptor), membrane extracts (amount of protein/well optimized for each receptor), radiotracer [$^3$H]-DOI (final concentration optimized for each receptor) and test compound. Nonspecific binding is determined by co-incubation with 200-fold excess of cold competitor. The samples are incubated in a final volume of 0.1 ml at a temperature and for a duration optimized for each receptor and then filtered over filter plates. Filters are washed six times with 0.5 ml of ice-cold washing buffer (optimized for each receptor) and 50 μl of Microscint 20 (Packard) are added in each well. The plates are incubated 15 min on an orbital shaker and then counted with a TopCount™ for 1 min/well.

Serotonin 5-HT2C In Vitro Cellular IPOne Agonism Assay. The 5-HT2C IPOne HTRF assay was performed at Epics Therapeutics S.A. (Belgium, FAST-0507I) using conventional methods. Briefly, CHO-K1 cells expressing human recombinant 5-HT2C edited receptor (accession number AAF35842.1) grown to mid-log phase in culture media without antibiotics were detached with PBS-EDTA, centrifuged, and resuspended in medium without antibiotics buffer. 20,000 cells are distributed in a 96 well plate and incubated overnight at 37° C. with 5% $CO_2$.

For agonist testing, the medium is removed and 20 μl of assay buffer plus 20 μl of test compound or reference agonist are added in each well. The plate is incubated for 60 min. at 37° C. with 5% $CO_2$.

After addition of the lysis buffer containing IP1-d2 and anti-IP1 cryptate detection reagents, plates are incubated 1-hour at room temperature, and fluorescence ratios are measured according to the manufacturer specification, with the HTRF kit.

The compounds provided herein were tested in the Serotonin 5-HT2A and 5-HT2C in vitro radioligand binding and cellular IPOne agonism assays. The binding and agonism functional potencies of the compounds (as indicated by their $IC_{50}$s or $EC_{50}$s) are shown in Table 1.

TABLE 1

In vitro 5-HT2A and 5-HT2C Radioligand Binding and Cellular IPOne Agonism Activity

| Compound Number | 5-HT2A Radioligand Binding Activity | 5-HT2A IPOne Agonism Activity | 5-HT2C Radioligand Binding Activity | 5-HT2C IPOne Agonism Activity |
|---|---|---|---|---|
| 1 | B | B | C | B |
| 2 | D | C | D | D |
| 3 | D | C | E | E |
| 4 | D | C | E | D |
| 5 | C | B | C | C |
| 6 | D | C | D | D |
| 7 | B | B | C | C |
| 8 | C | C | D | D |
| 9 | B | B | B | B |
| 10 | C | C | C | C |
| 11 | B | A | C | B |
| 12 | C | B | D | C |
| 13 | D | E | C | C |
| 14 | C | E | B | C |
| 15 | C | E | C | C |
| 16 | C | C | C | C |
| 17 | D | E | C | C |
| 19 | E | E | C | C |
| 21 | D | D | C | C |
| 23 | D | D | C | C |
| 25 | E | E | D | D |
| 27 | D | D | C | C |

Legend for Table 1:
A: IC50 or EC50 is <0.010 μM
B: IC50 or EC50 is 0.010 μM-0.100 μM
C: IC50 or EC50 is 0.101 μM-1 μM
D: IC50 or EC50 is 1.001 μM-10 μM
E: IC50 or EC50 is >10 μM

Example 32: Neurite Assays

Neurite Outgrowth in Primary Neuronal Cultures Assay. Changes in the pattern of neurite outgrowth have been implicated in psychiatric and neurodegenerative disorders as well as traumatic injuries. The discovery of new compounds that can positively affect neuritogenesis are important for developing new therapeutics for neurological diseases. Measurement of neurite outgrowth of rat cortical neurons using an automated image-based assay was used to determine the neuroplastic effects of the compounds of the present invention. The neurite outgrowth assay was performed at Neurofit SAS (France) as described below.

Pregnant Wistar rats (Janvier; France) were used for the study. They were delivered 6 days before their use. Upon arrival at Neurofit animal facility, they were housed one per cage and maintained in a room with controlled temperature (21-22° C.) and a reversed light-dark cycle (12 h/12 h; lights on: 17:30-05:30; lights off: 05:30-17:30) with food and water available ad libitum.

Female Wistar rats of 17 days gestation were killed by cervical dislocation and the fetuses were removed from the uterus. Their brains were placed in ice-cold medium of Leibovitz (L15, Gibco, Fisher bioblock, France). Cortices were dissected and meninges were carefully removed. The cortical neurons were dissociated by trypsinization for 30 min at 37° C. (trypsin-EDTA, Gibco) in presence of 0.1 mg/ml DNAse I (Roche, France). The reaction was stopped by addition of Dulbecco's Modified Eagle Medium (DMEM; Gibco) with 10% of fetal bovine serum (FBS; Gibco). The suspension was triturated with a 10-ml pipette and using a needle syringe 21 G and centrifuged at 350×g for 10 min at room temperature. The pellet of dissociated cells was resuspended in a medium consisting of Neurobasal (Gibco) supplemented with 2% B27 supplement (Gibco), 0.5 mM L-Glutamine (Gibco), an antibiotic-antimicotic mixture. Viable cells were counted in a Neubauer cytometer using the trypan blue exclusion test (Sigma). Cells were seeded at a density of 10000 cells per well in 96-well plate (Costar) precoated with poly-L-lysine. Test compound at different concentrations were added to the cultures. Donepezil (positive control) was tested at 250 nM.

After 72 h (3 days) of plating, cultures were fixed with paraformaldehyde in PBS (4%, Sigma) for 30 min at 4° C. Then, cells were successively permeabilized with 0.1% Triton X100 for 30 min, saturated with PBS containing 3% of BSA and were incubated 1 h with anti-beta III tubulin antibody (Sigma) at 1/10000 in PBS containing 0.5% of BSA. Cells were washed three times with PBS containing 0.5% of BSA, and they were incubated 1 h with goat anti-mouse antibody coupled with AF488 (Invitrogen A11001) diluted at 1/1000 in PBS containing 0.5% of BSA. Finally, nuclei were staining with DAPI 1 mg/ml at 1/1000 in PBS containing 0.5% of BSA. After rinsing with PBS, the plate was filmed and neurite networks were examined and analyzed using High-Content Screening (CellInsight, Thermo Scientific). The average number of neurites per neuron and the average total length of neurites per neuron were the main parameters analyzed. Analysis of data was performed using analysis of variance (ANOVA). The Fisher's Protected Least Significant Difference test was used for multiple comparisons. A p value <0.05 was considered significant. The software used is StatView 5.0 from SAS Institut.

In some embodiments, a compound of the present invention increases the pattern of neurite outgrowth. In some embodiments, a compound of the present invention increases neurite average length compared to a control. In some embodiments, a compound of the present invention increases neurite branch points compared to a control. In some embodiments, a compound of the present invention significantly increases the number of new neurites and/or the average neurite length compared to a control.

The plastogenic potential of the compounds is shown in Table 2.

TABLE 2

In vitro 5-HT2A and 5-HT2C Radioligand Binding and Cellular IPOne Agonism Activity

| Compound Number | Increase in Neurite Number | Increase in Neurite Length |
|---|---|---|
| 3 | B | B |
| 4 | A | A |
| 5 | A | A |
| 6 | A | A |
| 7 | B | B |
| 8 | A | A |
| 9 | A | A |
| 10 | A | A |
| 11 | A | A |
| 12 | A | A |
| 13 | A | A |
| 14 | A | A |
| 15 | B | B |
| 16 | A | A |
| 27 | A | A |

Legend for Table 2:
A: Statistically significant mean increase as a percent of DMSO control at 10 μM or less
B: No statistically significant mean increase as a percent of DMSO control at 10 μM or less Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference. Where a conflict exists between the instant application and a reference provided herein, the instant application shall dominate.

What is claimed is:

1. A compound, or a pharmaceutically acceptable salt thereof, that is:

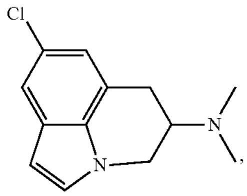,
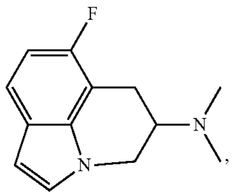,
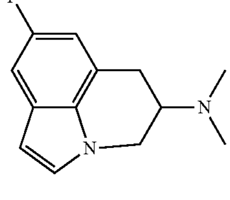,
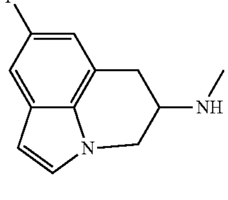,

-continued

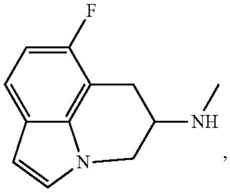,
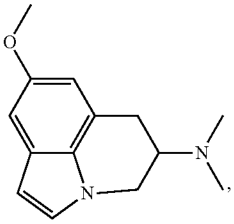,
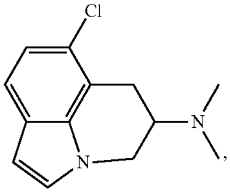,
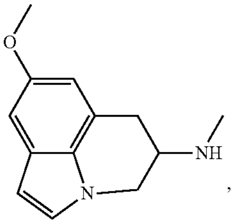,
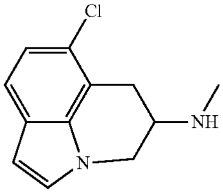,
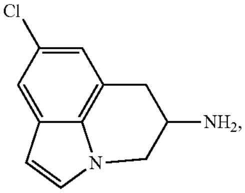,
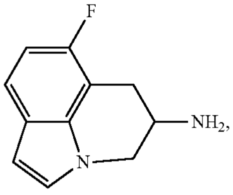,
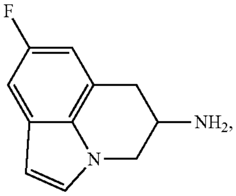,
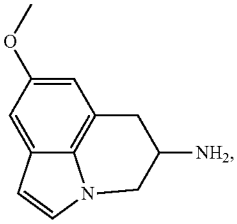,
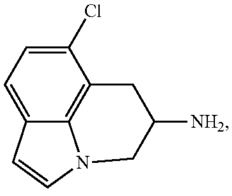,
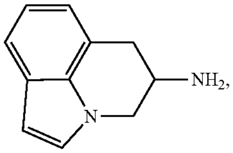,
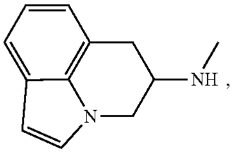,
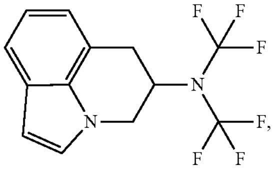,
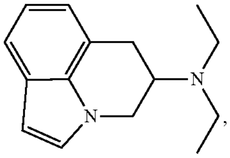,
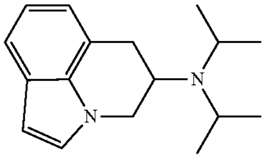,
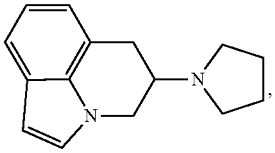, or -continued

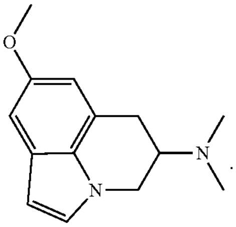.

2. The compound of claim 1, or a pharmaceutically acceptable salt thereof, that is:

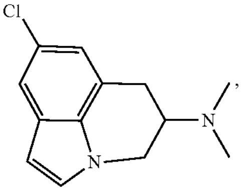,
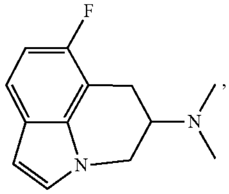,
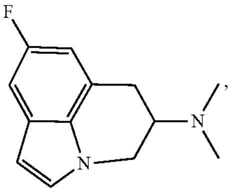,
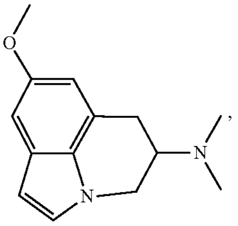,
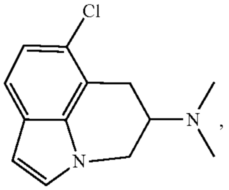,
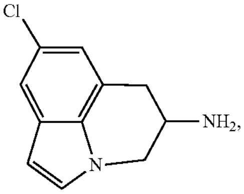,
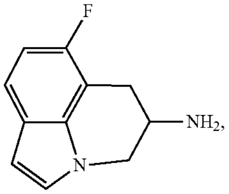,
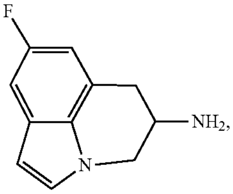,
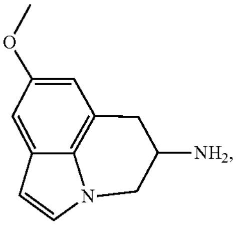,
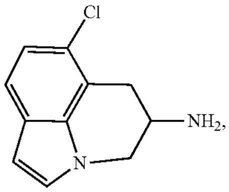,
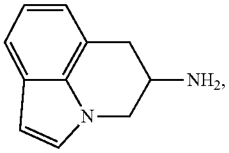, or
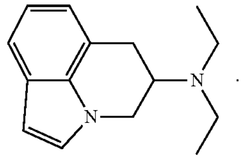.

3. A pharmaceutical composition, comprising a therapeutically effective amount of a compound of claim 1, or a pharmaceutically acceptable salt thereof.

4. A method for increasing neural plasticity, the method comprising contacting a neuronal cell with a compound of claim 1, or a pharmaceutically acceptable salt thereof, in an amount sufficient to increase neural plasticity of the neuronal cell, wherein the compound produces a maximum number of dendritic crossings with an increase of greater than 1.0 fold by a Sholl Analysis.

5. A method for increasing neural plasticity and increasing dendritic spine density, the method comprising contacting a neuronal cell with a compound of claim 1, or a pharmaceutically acceptable salt thereof, in an amount sufficient to increase neural plasticity and increase dendritic spine density of the neuronal cell.

* * * * *